United States Patent
Zlotnick et al.

(10) Patent No.: US 10,220,034 B2
(45) Date of Patent: Mar. 5, 2019

(54) HEPATITIS B VIRAL ASSEMBLY EFFECTORS

(71) Applicant: Indiana University Research and Technology Corp., Indianapolis, IN (US)

(72) Inventors: Adam Zlotnick, Bloomington, IN (US); Lichun Li, Bloomington, IN (US); William W. Turner, Jr., Bloomington, IN (US); Samson Francis, Bloomington, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 15/030,378

(22) PCT Filed: Oct. 16, 2014

(86) PCT No.: PCT/US2014/060869
§ 371 (c)(1),
(2) Date: Apr. 19, 2016

(87) PCT Pub. No.: WO2015/057945
PCT Pub. Date: Apr. 23, 2015

(65) Prior Publication Data
US 2016/0271130 A1 Sep. 22, 2016

Related U.S. Application Data

(60) Provisional application No. 61/892,591, filed on Oct. 18, 2013.

(51) Int. Cl.
*A61K 31/506* (2006.01)
*C07D 239/47* (2006.01)
*C07D 239/48* (2006.01)

(52) U.S. Cl.
CPC .......... *A61K 31/506* (2013.01); *C07D 239/47* (2013.01); *C07D 239/48* (2013.01)

(58) Field of Classification Search
None
See application file for complete search history.

(56) References Cited

U.S. PATENT DOCUMENTS

| | | |
|---|---|---|
| 7,482,351 B2 | 1/2009 | Singh et al. |
| 7,816,351 B2 | 10/2010 | Han et al. |
| 2006/0293343 A1 | 12/2006 | Naganuma et al. |
| 2011/0288082 A1 | 11/2011 | Deshaies et al. |
| 2012/0329780 A1 | 12/2012 | Thormann et al. |

FOREIGN PATENT DOCUMENTS

| | | | |
|---|---|---|---|
| CN | 101268081 A | | 9/2008 |
| WO | WO2010118367 A2 | | 10/2010 |
| WO | WO 2013/019967 | * | 2/2013 |
| WO | WO 2013/019967 A1 | | 2/2013 |
| WO | WO 2014/060112 A1 | | 4/2014 |

OTHER PUBLICATIONS

Martyn et al. Antiplasmodial activity of piperazine sulfonamides. Bioorganic & Medicinal Chemistry Letters, 20, 2010, 218-221.*
RN 946314-38-1. Electronic Resource. Sep. 7, 2007.*
International Search Report and Written Opinion issued by the ISA/US, Commission for Patents, dated Jan. 21, 2015, for International Application No. PCT/US2014/060869; 7 pages.
International Preliminary Report on Patentability issued by the International Bureau of WIPO, dated Apr. 19, 2016, for International Application No. PCT/US2014/060869; 5 pages.
Examination Report issued by the Patent Office of the People's Republic of China (English translation), dated Jan. 24, 2018, for related Chinese Application No. 201480068103.X; 6 pages.

* cited by examiner

*Primary Examiner* — Anna Pagonakis
(74) *Attorney, Agent, or Firm* — Faegre Baker Daniels LLP

(57) ABSTRACT

Novel assembly effector compounds having a therapeutic effect against hepatitis B viral (HBV) infection are disclosed. Assembly effector molecules described herein can lead to defective viral assembly and also may affect other viral activities associated with chronic HBV infection. Also disclosed is a process to synthesize disclosed compounds, method of treatment of HBV by administration of disclosed compounds, and use of these compounds in the manufacture of medicaments against HBV.

18 Claims, No Drawings

HEPATITIS B VIRAL ASSEMBLY EFFECTORS

RELATED APPLICATIONS

This application is a U.S. National Phase Patent Application based on International Application Serial No. PCT/US2014/060869 filed Oct. 16, 2014, which claims the benefits of U.S. provisional patent applications Nos. 61/892,591, filed Oct. 18, 2013, the disclosures of which are hereby incorporated by reference in their entity.

STATEMENT OF GOVERNMENT SUPPORT

This invention was made with government support under AI067417 awarded by the National Institutes of Health. The government has certain rights in the invention.

BACKGROUND

Hepatitis B (HBV) causes viral hepatitis that can further lead to chronic liver disease and increase the risk of liver cirrhosis and liver cancer (hepatocellular carcinoma). Worldwide, more than 2 billion people have been infected with HBV around 360 million people are chronically infected and every year HBV infection causes more than one million deaths. HBV can be spread by body fluids: from mother to child, by sex, and via blood products. Children born to HBV-positive mothers may also be infected, unless vaccinated at birth.

At present, chronic HBV is primarily treated with nucleosides/nucleotides (e.g. entecavir) that suppress the virus while the patient remains on treatment but do not eliminate the infection, even after many years of treatment. Once a patient starts taking nucleotide analogs most must continue taking them or risk the possibility of a life threatening immune response to viral rebound. Further, antiviral nucleoside therapy may lead to the emergence of antiviral drug resistance.

The only FDA approved alternative to antiviral nucleoside/nucleotide analogs is treatment with interferon α or pegylated interferon α. Unfortunately, the adverse event incidence and profile of interferon-α can result in poor tolerability, and many patients are unable to complete therapy. Moreover, only a small percentage of patients are considered appropriate for interferon therapy, as only a small subset of patients who present with low viral loads and transaminitis greater than 2× the upper limit of normal are likely to have a sustained clinical response to a year-long course of interferon therapy. As a result, interferon-based therapies are used in only a small percentage of all diagnosed patients who elect for treatment.

Thus, current HBV treatments can range from palliative to benign neglect. Nucleoside analogs suppress virus production, treating the symptom, but leave the infection intact. Interferon α has severe side effects and less tolerability among patients and is successful as a finite treatment strategy in only a small minority of patients. There is a clear on-going need for more effective treatments for HBV infections.

SUMMARY

The present disclosure is directed in part to 2,4-diaminopyrimidine compounds having activity against hepatitis B virus, for example, by affecting assembly of viral capsid proteins. For example, disclosed compounds may be considered CpAMs—core protein allosteric modifiers—which can lead to defective viral capsid assembly. Without being bound by any theory, such CpAMs may affect steps "upstream" of capsid assembly by altering the concentrations of Cp (core protein) available as dimers as compared to capsid or other multimeric forms. Disclosed compounds or CpAMs may noticeably affect functions upstream of viral assembly, such as interfering with cccDNA transcription, RNA stability and/or protein-protein interactions.

In one aspect, the present invention provides a pharmaceutical composition comprising: (i) a compound of Formula 1 having the structure:

Formula 1

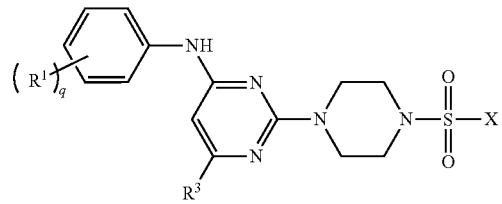

or a pharmaceutically acceptable salt or stereoisomer thereof, wherein:

X is selected from the group consisting of

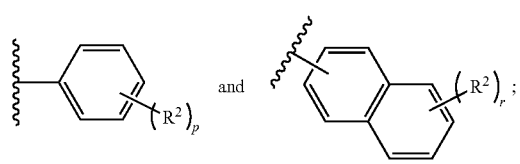

q is 0, 1, 2, 3 or 4;
p is 0, 1, 2, 3, or 4;
r is 0, 1, 2, 3, or 4
$R^1$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R");
w is 0, 1 or 2;
R' is independently for each occurrence selected from the group consisting of —H and —$C_1$-$C_6$alkyl;
R" is independently for each occurrence selected from the group consisting of —H and —$C_1$-$C_6$alkyl; or R' and R" are taken together with the nitrogen atom to which they are attached to form a 4-7 membered heterocyclic ring;
$R^2$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R"); and
$R^3$ is selected from the group consisting of —H and —$C_1$-$C_6$alkyl;

wherein $C_1$-$C_6$alkyl or $C_1$-$C_6$alkoxy may be independently for each occurrence optionally substituted with one, two, or three halogens; and (ii) a pharmaceutically acceptable excipient.

In another aspect, the present disclosure provides a method of treating, ameliorating, preventing, or substantially delaying a hepatitis B viral infection in an the method comprising administering to the individual a pharmaceutical composition disclosed herein.

In another aspect, the present disclosure relates to use of a compound of Formula 1, Formula 1-A, or Formula 1-B in the manufacture of a medicament for the treatment of a hepatitis B viral infection.

DETAILED DESCRIPTION

Definitions

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

As intended herein, the terms "a" and "an" include singular as well as plural references unless the context clearly dictates otherwise. For example, the term "an assembly effector" can include one or more such effectors.

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-6 or 3-4 carbon atoms, referred to herein for example as $C_2$-$C_6$ alkenyl, and $C_3$-$C_4$ alkenyl, respectively. Exemplary alkenyl groups include, but are not limited to, vinyl, allyl, butenyl, pentenyl, etc.

The term "alkoxy" as used herein refers to a straight or branched alkyl group attached to an oxygen (alkyl-O—). Exemplary alkoxy groups include, but are not limited to, groups with an alkyl group of 1-6 or 2-6 carbon atoms, referred to herein as $C_1$-$C_6$ alkoxy, and $C_2$-$C_6$ alkoxy, respectively. Exemplary alkoxy groups include, but are not limited to methoxy, ethoxy, isopropoxy, etc.

The term "alkyl" as used herein refers to a saturated straight or branched hydrocarbon, such as a straight or branched group of 1-6, 1-4, or 1-3 carbon atoms, referred to herein as $C_1$-$C_6$ alkyl, $C_1$-$C_4$ alkyl, and $C_1$-$C_3$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 3-methyl-2-butyl, 2,2-dimethyl-1-propyl, 2-methyl-1-pentyl, 3-methyl-1-penyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, etc.

The term "alkynyl" as used herein refers to an unsaturated straight or branched hydrocarbon having at least one carbon-carbon triple bond, such as a straight or branched group of 2-6, or 3-6 carbon atoms, referred to herein as $C_2$-$C_6$ alkynyl and $C_3$-$C_6$ alkynyl, respectively. Exemplary alkynyl groups include, but are not limited to, ethynyl, propynyl, butyl pentynyl, hexynyl, methylpropynyl, etc.

The term "cycloalkoxy" as used herein refers to a cycloalkyl group attached to an oxygen (cycloalkyl-O—).

The term "cycloalkyl" as used herein refers to a monocyclic saturated or partially unsaturated hydrocarbon group of, for example 3-6, or 4-6 carbons, referred to herein, e.g., as $C_3$-$C_6$ cycloalkyl or $C_4$-$C_6$ cycloalkyl. Exemplary cycloalkyl groups include, but are not limited to, cyclohexane, cyclohexene, cyclopentane, cyclobutane or, cyclopropane.

The terms "halo" or "halogen" as used herein refer to F, Cl, Br, or I.

The terms "hydroxy" and "hydroxyl" as used herein refers to the radical —OH.

"Pharmaceutically or pharmacologically acceptable" include molecular entities and compositions that do not produce an adverse, allergic or other untoward reaction when administered to an animal, or a human, as appropriate. For human administration, preparations should meet sterility, pyrogenicity, general safety, and purity standards as required by FDA Office of Biologics standards.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include any animal, including mammals, preferably mice, rats, other rodents, rabbits, dogs, cats, swine, cattle, sheep, horses, or primates, and most preferably humans. The compounds of the invention can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in which treatment of hepatitis B is desired. "Modulation" includes antagonism (e.g., inhibition), agonism, partial antagonism and/or partial agonism.

In the present disclosure, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfate, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts. Compounds included in the present compositions that include a basic or acidic moiety may also form pharmaceutically acceptable salts with various amino acids. The compounds of the disclosure may contain both acidic and basic groups; for example, one amino and one carboxylic acid group. In such a case, the compound can exist as an acid addition salt, a zwitterion or a base salt.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

The compounds of the disclosure may contain one or more chiral centers and/or double bonds and, therefore, exist as geometric isomers, enantiomers or diastereomers. The enantiomer and diastereomers may be designated by the symbols "(+)," "(−)." "R" or "S," depending on the configuration of substituents around, the stereogenic carbon atom, but the skilled artisan will recognize that a structure may denote a chiral center implicitly. Geometric isomers, resulting from the arrangement of substituents around a carbon-carbon double bond or arrangement of substituents around a cycloalkyl or heterocyclic ring, can also exist in the compounds of the present invention. The symbol ===== denotes a bond that may be a single, double or triple bond as described herein. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers. Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The term "stereoisomers" when used herein consist of all geometric isomers, enantiomers or diastereomers. The present invention encompasses various stereoisomers of these compounds and mixtures thereof.

Individual enantiomers and diastereomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diasteriomers by recrystallization or chromatography and liberation of the optically pure product from the auxiliary, (2) salt formation employing an optically active resolving agent, (3) direct separation of the mixture of optical enantiomers on chiral liquid chromatographic columns or (4) kinetic resolution rising stereoselective chemical or enzymatic reagents. Racemic mixtures can also be resolved into their component enantiomers by well known methods, such as chiral-phase gas chromatography or crystallizing the compound in a chiral solvent. Stereoselective syntheses, a chemical or enzymatic reaction in which a single reactant forms an unequal mixture of stereoisomers during the creation of a new stereocenter or during the transformation of a pre-existing one, are well known in the art. Stereoselective syntheses encompass both enantio- and diastereoselective transformations. For examples, see Carreira and Kvaerno, *Classics in Stereoselective Synthesis*, Wiley-VCH: Weinheim, 2009.

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically-labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. For example, a compound of the invention may have one or more H atom replaced with deuterium.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms (such as by esterase, amidase, phosphatase, oxidative and/or reductive metabolism) in various locations (such as in the intestinal lumen or upon transit of the intestine, blood or liver). Prodrugs are well known in the art (for example, see Rautio, Kumpulainen, et al, Nature Reviews Drug Discovery 2008, 7, 255). For example, if a compound of the invention or a pharmaceutically acceptable salt, hydrate or solvate of the compound contains a carboxylic acid functional group, a prodrug can comprise an ester formed by the replacement of the hydrogen atom of the acid group, for example with a group such as $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the invention contains an alcohol functional group, a prodrug can be formed by the replacement of the hydrogen atom of the alcohol group with a group such as, for example, $(C_1-C_6)$alkanoyloxymethyl, 1-$((C_{1-6})$alkanoyloxy)ethyl, 1-methyl-1-$((C_1-C_6)$alkanoyloxy)ethyl $(C_1-C_6)$alkoxycarbonyloxymethyl, N-$(C_1-C_6)$ alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, wherein each α-aminoacyl group is independently selected from the naturally occurring L-amino acids; or $P(O)(OH)_2$, —$P(O)(O(C_1-C_6)alkyl)_2$, or glycosyl (the radical resulting from the removal of a hydroxyl group of the hemiacetal form of a carbohydrate).

If a compound of the invention incorporates an amine functional group, a prodrug can be thrilled, for example, by creation of an amide or carbamate, an N-acyloxyakyl derivative, an (oxodioxolenyl)methyl derivative, an N-Mannich base, imine or enamine. In addition, a secondary amine can be metabolically cleaved to generate a bioactive primary amine, or a tertiary amine can metabolically cleaved to generate a bioactive primary or secondary amine. For examples, see Simplicio, et al., *Molecules* 2008, 13, 519 and references therein.

The present invention is based in part on the discovery of that certain classes of compounds such as those described herein may activate assembly of the viral capsid independent of the normal nucleating signals, e.g. act as core protein allosteric modulators having an effect against HBV. For example, disclosed compounds may activate assembly of the viral capsid independent of the normal nucleating signals.

Hepatitis B virus, for example, consists of an envelope, a nucleocapsid core, viral DNA, and reverse transcriptase (RT). Infection starts when the virus enters the host. The viral core enclosing the viral DNA and the RT are then transferred to cytoplasm of the host and to the host's nucleus, a process in which the circular and partially double stranded viral DNA is released from the viral core.

Inside the nucleus, the viral DNA is converted into a covalently-closed circular DNA (cccDNA), which codes for a pregenomic RNA (pg RNA) and other mRNAs. The pregenomic RNA, exported to the cytoplasm, codes for core protein and the reverse transcriptase. Encapsidation of the pregenomic RNA and the reverse transcriptase by core protein results in the formation of immature HBV cores which maturate as the pregenomic RNA is reverse transcribed to the circular and partially double stranded DNA, completing the cycle.

Central to HBV infection is the assembly of the viral core. The capsid itself is a complex of 120 copies of core protein homodimers that spontaneously self-assemble. In the presence of assembly effectors (AE) capsid assembly begins with an CpAM•Cp (Assembly effector•Core protein) complex instead of waiting for the biological RT•pgRNA nucleating complex; the resulting capsid is thus defective. CpAMs can leverage consumption of a few molecules needed for nucleation to consume for example up to 117 Cp dimers. To nucleate assembly, in some embodiments, CpAMs may have one or both of activities such as substantially interacting; with or e.g., binding to Cp dimers, activating assembly, and/or substantially binding or interacting with capsids at e.g., a higher affinity as compared to binding to the Cp dimer.

Core proteins also have roles upstream of capsid assembly and are associated with nuclear cccDNA and affect their stability and transcription; they are involved in export of the pregenomic RNA from the nucleus.

For example, the compounds provided herein may affect virus assembly by interacting with core protein dimers as well as capsids, and/or may affect core protein activity upstream of capsid assembly. Defective assembly can immediately suppress virus production. Suppressed Cp activity upstream of assembly can also interfere with activities of the virus required for stability of the infection itself. For example, provided compounds may successfully treat HBV with a finite course of therapy (as opposed to the potentially life-long therapy necessary with current antiviral nucleosides/nucleotides), e.g. such finite therapy would result from a loss of new viral proteins and mRNA resulting from epigenetic modification of the viral cccDNA, as well as a reduction in new infectious virions. In other words, disclosed compounds may activate viral capsid assembly independent of the normal nucleating signals leading to defective assembly capsid assembly begins with an AE•Cp complex instead of waiting for the biological RT•pgRNA nucleating complex; the resulting capsid or aberrant complex, e.g., cannot support production of a new virion. In some embodiments, disclosed compounds may leverage consumption of a few molecules needed for nucleation to consume up to 120 Cp dimers. Without being bound by theory, disclosed compounds may, for example, alter the concentration of Cp (core protein), likely required for activities upstream of capsid assembly. Suppressing Cp activity upstream of assembly interferes with the Cp interactions with the viral reservoir (cccDNA). This may lead to clearance of the infection by reduction of viral proteins and cccDNA activity.

The disclosure provides, in an embodiment, compounds of Formula 1 below, and a pharmaceutical composition comprising: (i) a compound of Formula 1 having the structure:

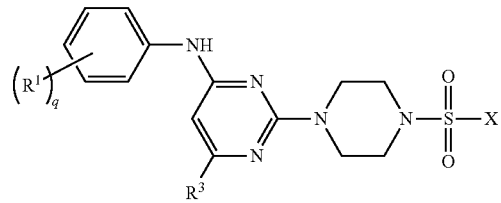

Formula 1 or a pharmaceutically acceptable salt, stereoisomer or prodrug thereof, wherein:

X is selected from the group consisting of

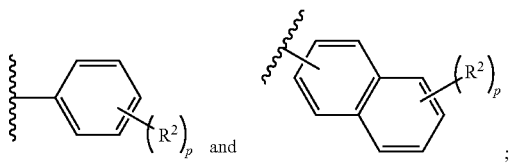

q is 0, 1, 2, 3 or 4;
p is 0, 1, 2, 3, or 4;
q is 0, 1, 2, 3, or 4;
$R^1$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R'');
w is 0, 1 or 2;
R' is independently for each occurrence selected from the group consisting of —H and —$C_1$-$C_6$alkyl;
R'' is independently for each occurrence selected from the group consisting of —H and —$C_1$-$C_6$alkyl; or R' and R'' are taken together with the nitrogen atom to which they are attached to form a 4-7 membered heterocyclic ring;
$R^2$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R''); and
$R^3$ is selected from the group consisting of —H and —$C_1$-$C_6$alkyl;
wherein $C_1$-$C_6$alkyl or $C_1$-$C_6$alkoxy may be independently for each occurrence optionally substituted with one, two, or three halogens; and
(ii) a pharmaceutically acceptable excipient.
In certain embodiments, p is 1 or 2.
In certain embodiments, the compound of Formula 1 is represented by Formula 1-A:

Formula 1-A

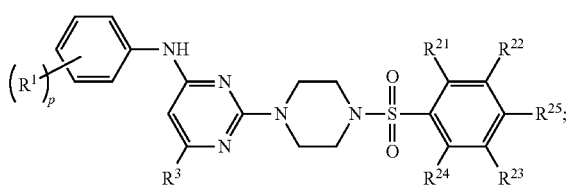

a pharmaceutically acceptable salt or stereoisomer thereof, wherein:
$R^1$ is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R'');

$R^{21}$ is independently for each occurrence selected from the group consisting of —H and halogen;
$R^{22}$ is independently for each occurrence selected from the group consisting of —H, —$C_1$-$C_6$alkyl, —$C_1$-$C_6$-alkoxy, —$C_1$-$C_6$alkyl-O—$C_1$-$C_6$alkyl, halogen, cyano, —OH, —C(O)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R'');
$R^{23}$ is independently for each occurrence selected from the group consisting of —H, —$C_1$-$C_6$alkyl, —$C_1$-$C_6$-alkoxy, —$C_1$-$C_6$alkyl-O—$C_1$-$C_6$alkyl, halogen, cyano, —OH, —C(O)H, —$CO_2$R', —C(O)N(R')(''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R''); and
$R^{24}$ is independently for each occurrence selected from the group consisting of —H and halogen;
$R^{25}$ is independently for each occurrence selected from the group consisting of —H, —$C_1$-$C_6$alkyl, —$C_1$-$C_6$alkoxy-O—$C_1$-$C_6$alkyl, halogen, cyano, —OH, —C(O)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R'');
w is 0, 1 or 2;
q is 0, 1, 2, 3 or 4;
R' is independently for each occurrence selected from the group consisting of —H and —$C_1$-$C_6$alkyl;
R'' is independently for each occurrence selected from the group consisting of —H and —$C_1$-$C_6$alkyl; or R' and R'' are taken together with the nitrogen atom to which they are attached to form a 4-7 membered heterocyclic ring;
$R^3$ is selected from the group consisting of —H and —$C_1$-$C_6$alkyl;
wherein $C_1$-$C_6$alkyl or $C_1$-$C_6$alkoxy may be independently for each occurrence optionally substituted with one, two, or three halogens;
wherein $C_1$-$C_6$alkyl or $C_1$-$C_6$alkoxy may be independently for each occurrence optionally substituted with one, two or three halogens.
In certain embodiments, $R^{21}$ and/or $R^{24}$ is —H.
In certain embodiments, $R^{22}$ is selected from the group consisting of H, —$C_1$-$C_6$alkyl, —$C_1$-$C_6$alkoxy, —$C_1$-$C_6$alkyl-O-$C_1$-$C_6$alkyl, halogen, cyano, —OH, —(C)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R'').
In certain embodiments, $R^{22}$ is independently for each occurrence selected from the group consisting of —H, —$C_1$-$C_6$alkyl, —$C_1$-$C_6$alkoxy, and halogen.
In certain embodiments, $R^{23}$ is selected from the group consisting of H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R''), —C(O)$C_1$-$C_6$alkyl, —N(R')(R''), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R'').
In certain embodiments, $R^{23}$ is independently for each occurrence selected from the group consisting of —H, —$C_1$-$C_6$alkyl, —$C_1$-$C_6$alkoxy, and halogen.
In certain embodiments, $R^{25}$ is selected from the group consisting of —H, —$C_1$-$C_6$alkyl, —$C_1$-$C_6$alkoxy, halogen, cyano, —$CO_2$R', —N(R')C(O)$C_1$-$C_6$alkyl, —C(O)N(R')(R''), —C(O)$C_1$-$C_6$alkyl, and —N(R')(R'').

In certain embodiments, $R^1$ is selected independently for each occurrence from the group consisting of —H, —CH$_1$-C$_6$alkyl, —C$_1$-C$_6$alkoxy, halogen, cyano, and —OH.

In certain embodiments, q is 1 or 2.

In certain embodiments, the compound of Formula 1 is represented by Formula 1-B:

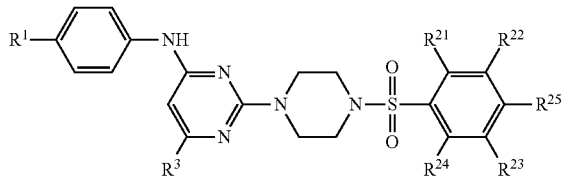

Formula 1-B or a pharmaceutically acceptable salt or stereoisomer thereof, wherein $R^1$ is selected from the group consisting of —H, —CH$_3$, —CH$_2$CH$_3$, —CF$_3$, —F, —Cl, —Br, cyano, —OCH$_3$ and —OCF$_3$;

$R^{23}$ is selected from the group consisting of —H, —CH$_3$, —F, or —OCH$_3$; and $R^{25}$ is selected from the group consisting of —H, —CH$_3$, —CH$_2$CH$_3$, —CH$_2$CH$_2$CH$_3$, —CF$_3$, —F, —Cl, —OH, —OCH$_3$, —OCH$_2$CH$_3$, —OC(CH$_3$)$_3$, —OCH$_2$CH$_2$CH$_3$, —NH$_2$, —NHCH$_3$, —NHC(O)CH$_3$, —NHC(O)CF$_3$, —OCHF$_2$, and —OCF$_3$, with other R stibsitituents as above.

In certain embodiments, $R^3$ of Formula 1, 1-A or 1-B is selected from the group consisting of —CH$_3$, —CH(CH$_3$)$_2$, —CH$_2$CH$_2$CH$_3$, —CF$_3$, and —C(CH$_3$)$_3$.

In certain embodiments, $R^2$ of Formula 1, 1-A or 1-B is selected from the group consisting of —H, —CH, —CH$_2$CH$_3$, —CF$_3$, —F, —Cl, —Br, —CN, —OCH$_3$, and —OCF$_3$.

In another aspect, the present disclosure provides a method of treating, ameliorating, preventing, or substantially delaying a hepatitis B viral infection in an individual, the method comprising administering to the individual a compound or a pharmaceutical composition disclosed herein.

In another aspect, the present disclosure relates to use of a compound of Formula 1, Formula 1-A, or Formula 1-B in the manufacture of a medicament for the treatment of a hepatitis B viral infection.

Disclosed compounds may be prepared by methods known in the art. A disclosed compound may be preparing ming a method comprising providing 2,4-dichloro-6-substituted pyrimidine and a R-substituted aniline group together in an organic solvent (wherein R may be selected from $R^1$ above), and then contacting a resultant compound with Z (e.g. piperzine or 4-amino aniline group).

Thereafter, an optionally substituted sulfonyl benzene group is added. In a further aspect, a method for treating HBV infection (e.g. an acute or chronic HBV infection) in a patient in need thereof is provided. The method includes administering to a patient a pharmaceutical composition comprising a therapeutically effective amount of a disclosed compound.

For use in accordance with this aspect, the appropriate dosage is expected to vary depending on, for example, the particular compound employed, the mode of administration, and the nature and severity of the infection to be treated as well as the specific infection to be treated and is within the purview of the treating physician. Usually, an indicated administration dose may be in the range between about 0.1 to about 15 mg/kg body weight. In some cases, the administration dose of the compound may be less than 10 mg/kg body weight. In other cases, the administration dose may be less than 5 mg/kg body weight. In yet other cases, the administration dose may be in the range between about 0.1 to about 1 mg/kg body weight. The dose may be conveniently administered once daily, or in divided doses up to, for example, four times a day or in sustained release form.

A compound or composition may be administered by any conventional route, in particularly: enterally, topically, orally, nasally, e.g. in the form of tablets or capsules, via suppositories, or parenterally, e.g. in the form of injectable solutions or suspensions, for intravenous, intra-muscular, sub-cutaneous, or intra-peritoneal injection. Suitable formulations and pharmaceutical compositions will include those formulated in a conventional manner using one or more physiologically acceptable carriers or excipients, and any of those known and commercially available and currently employed in the clinical setting. Thus, the compounds may be formulated for oral, buccal, topical, parenteral, rectal or transdermal administration or in a form suitable for administration by inhalation or insufflation (either orally or nasally).

For oral administration, pharmaceutical compositions may take the form of, for example, tablets or capsules prepared by conventional means with pharmaceutically acceptable excipients such as binding agents (e.g. pregelatinized maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulfate). Tablets may be coated by methods well known in the art. Liquid preparations for oral administration may take the form of for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated Vegetable oils); and preservatives (e.g. methyl or propyl-p-hydroxybenzoates or sorbic acid). Preparations may also contain buffer salts, flavoring, coloring and sweetening agents as appropriate.

Preparations for oral administration may also be suitably formulated to give controlled-release or sustained release of the active compound(s) over an extended period. For buccal administration the compositions may take the form of tablets or lozenges formulated in a conventional manner known to the skilled artisan.

A compound may also be formulated for parenteral administration by injection e.g. by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain additives such as suspending, stabilizing and or dispersing agents. Alternatively, the compound may be in powder form for constitution with a suitable vehicle, e.g. sterile pyrogen-free water, before use. Compounds may also be formulated for rectal administration as suppositories or retention enemas, e.g. containing conventional suppository bases such as cocoa butter or other glycerides.

In some cases, disclosed compounds may be administered as part of a combination therapy in conjunction with one or more antivirals. Exemplary antivirals include nucleoside analogs, interferon α and other assembly effectors, for instance heteroaryldihydropyrimidines (HAPs) such as methyl 4-(2-chloro-4-fluorophenyl)-6-methyl-2-(pyridin-2-yl)-1,4-dihydropyrimidine-5-carboxylate. This may involve administering to a subject a first amount of a disclosed compound in combination with a second amount of an antiviral, wherein the first and second amounts together comprise a pharmaceutically effective amount. The first amount, the second amount, or both may be the same, more, or less than effective amounts of each compound administered as monotherapies. Therapeutically effective amounts of disclosed compound and antiviral may be co-administered to the subject, i.e., administered to the subject simultaneously or separately, in any given order and by the same or different routes of administration. In some instances, it may be advantageous to initiate administration of a disclosed compound or composition first, for example one or more days or weeks prior to initiation of administration of the antiviral. Moreover, additional drugs may be given in conjunction with the above combination therapy.

EXAMPLES

Example 1

Synthesis of Common Intermediates 6 and 13

Synthesis of 6-methyl-2-(piperazin-1-yl)-N-(p-tolyl)pyrimidin-4-amine (6)—a Common Intermediate

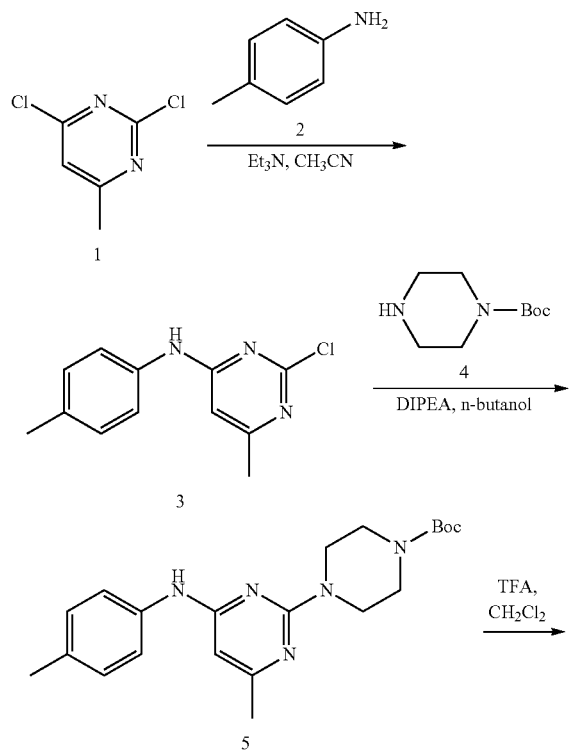

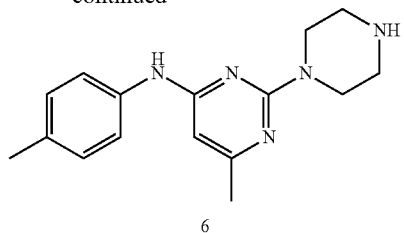

Synthesis of 2-chloro-6-methyl-N-(p-tolyl)pyrimidin-4-amime (3)

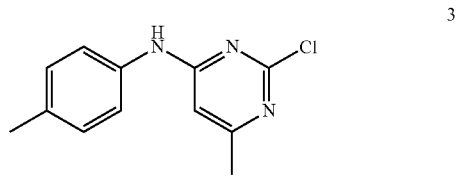 [SMILES: Cc1ccc(Nc2cc(C)nc(Cl)n2)cc1]

To a stirred solution of 2,4-dichloro-6-methylpyrimidine 1 (600 mg, 3.68 mmol) in CH₃CN (5 mL) under argon atmosphere were added p-toluidine 2 (473 mg, 4.41 mmol) and triethylamine (0.77 mL, 5.52 mmol) at RT; the mixture was warmed to 80° C. and stirred for 24 h. The reaction was monitored by TLC; after completion of the reaction, the volatiles were removed in vacuo to obtain the crude product. The crude product was purified through silica gel column chromatography using 10% ethyl acetate (EtOAc)/hexanes to afford compound 3 (300 mg, 35%) as an off-white solid. TLC: 20% EtOAc/hexanes ($R_f$ 0.4); ¹H-NMR (DMSO-$d_6$, 400 MHz): δ 9.76 (s, 1H), 7.42 (d, J=8.0 Hz, 2H), 7.16 (d, J=8.4 Hz, 2H), 6.52 (s, 1H), 2.27 (s 3H), 2.25 (s, 3H).

Synthesis of tert-butyl 4-(4-methyl-6-(p-tolylamino)pyrimidin-2-yl)piperazine-1-carboxylate (5)

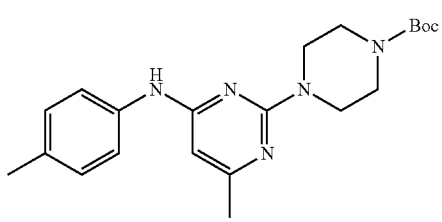

To a stirred solution of compound 3 (200 mg, 0.85 mmol) in n-butanol (3 mL) under argon atmosphere were added tert-butyl piperazine-1-carboxylate 4 (238 mg, 1.28 mmol) and N,N-diisopropylethylamine (DIPEA; 0.30 mL, 1.70 mmol) at RT; the mixture was heated to 100° C. and stirred for 16 h. The reaction was monitored by TLC; after completion of the reaction, the volatiles were removed in vacuo to obtain the crude product. The crude product was purified through silica gel column chromatography using 20% EtOAc/hexanes to afford compound 5 (220 mg, 67%) as an off-white solid. TLC: 20% EtOAc/hexanes ($R_f$ 0.5); ¹H-NMR (DMSO-$d_6$, 400 MHz): δ 9.00 (s, 1H), 7.45 (d, J=8.4 Hz, 2H), 7.10 (d, J=8.0 Hz, 2H), 5.89 (s, 1H), 3.66 (t, J=5.6 Hz, 4H), 3.31 (t, J=5.6 Hz, 4H), 2.24 (s, 3H), 2.12 (s, 3H), 1.42 (s, 9H).

Synthesis of 6-methyl-2-(piperazin-1-yl)-N-(p-tolyl)pyrimidin-4-amine (6)

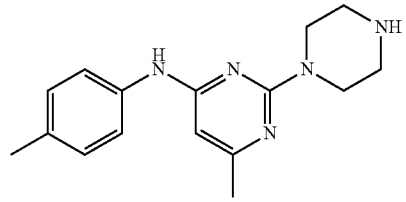

6

To a stirred solution of compound 5 (220 mg, 0.57 mmol) in CH$_2$Cl$_2$ (3 mL) under inert atmosphere was added trifluoroacetic acid (0.25 mL, 2.86 mmol) at 0° C.; the mixture was warmed to 15° C. and stirred for 30 min. The reaction was monitored by TLC; after completion of the reaction, the volatiles were removed in vacuo. The residue was neutralized with saturated NaHCO$_3$ solution (30 mL) and extracted with EtOAc (2×30 mL). The combined organic extracts were dried over sodium sulfate, filtered and concentrated in vacuo to afford compound 6 (130 mg, 80%) as an off-white solid. TLC: 5% MeOH/CH$_2$Cl$_2$ (R$_f$ 0.2); $^1$H-NMR (DMSO$_6$, 400 MHz): δ 8.98 (s, 1H), 7.45 (d, J=8.4 Hz, 2H), 7.09 (d, J=8.4 Hz, 2H), 5.87 (s, 1H), 3.67 (t, J=5.2 Hz, 4H), 2.81 (t, J=4.8 Hz, 4H), 2.24 (s, 3H), 2.12 (s, 3H).

Synthesis of N-(4-fluorophenyl)-6-isopropyl-2-(piperazin-1-yl)pyrimidin-4-amine (13)—a Common Intermediate

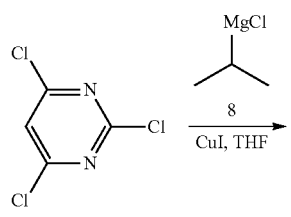

7

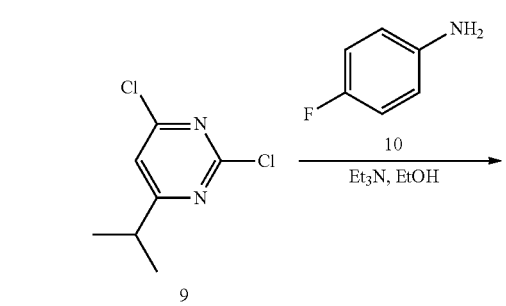

9

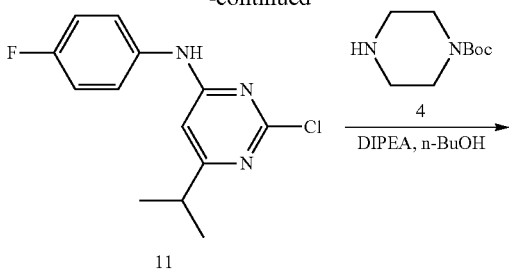

11

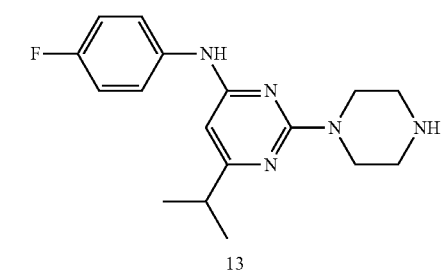

13

Synthesis of 2,4-dichloro-6-isopropylpyrimidine (9)

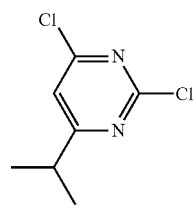

9

To a stirred solution of 2,4,6-trichloropyrimidine 7 (10 g, 54.49 mmol) in anhydrous tetrahydrofuran (THF; 200 mL) were added isopropyl magnesium chloride 8 (2 M sol. in THF, 54.5 mL, 109.0 mmol) and copper iodide (520 mg, 2.72 mmol) at −20° C. under argon atmosphere; the mixture was stirred at 0° C. for 2 h. The reaction was monitored by TLC; after completion of the reaction, the reaction mixture was quenched with aqueous saturated ammonium chloride solution (150 mL) and extracted with EtOAc (2×150 mL). The combined organic extracts were dried over sodium sulfate, filtered and concentrated in vacuo to obtain the crude product. The crude product was purified through silica gel column chromatography using 2% EtOAc/hexanes to afford compound 9 (6 g, 58%) as a colorless liquid. TLC: 7% EtOAc/hexanes (R$_f$ 0.8); $^1$H-NMR (CDCl$_3$, 400 MHz): δ 7.16 (s, 1H), 3.04-2.97 (m, 1H), 1.31 (d, J=6.8 Hz, 6H).

Synthesis of 2-chloro-N-(4-fluorophenyl)-6-isopropylpyrimidin-4-amine (11)

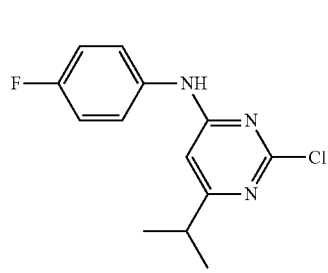

To a stirred solution of compound 9 (4.5 g, 23.56 mmol) in ethanol (50 mL) were added 4-fluoroaniline 10 (2.61 g, 23.56 mmol) and triethylamine (5.1 mL, 35.34 mmol) at RT under argon atmosphere; heated to 70° C. and stirred for 24 h. The reaction was monitored by TLC; after completion of the reaction, the volatiles were removed in vacuo to obtain the crude product. The crude product was purified through silica gel column chromatography using 4% EtOAc/hexanes to afford compound 11 (3.5 g, 56%) as an off-white solid. TLC: 10% EtOAc/hexanes ($R_f$ 0.2); $^1$H-NMR (CDCl$_3$, 400 MHz): δ 7.30-7.28 (m, 2H), 7.11 (t, J=8.0 Hz, 2H), 6.96 (br s, 1H), 6.30 (s, 1H), 2.84-2.77 (m, 1H), 1.21 (d, J=6.8 Hz, 6H).

Synthesis of tert-butyl 4-(4-((4-fluorophenyl)amino)-6-isopropylpyrimidin-2-yl)piperazine-1-carboxylate (12)

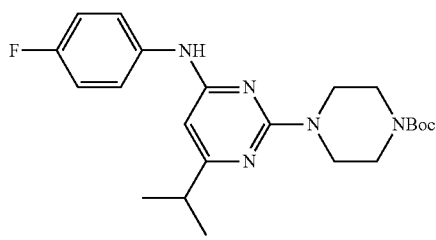

To a stirred solution of compound 11 (3.5 g, 13.21 mmol) in n-butanol (60 mL) were added tert-butyl piperazine-1-carboxylate 4 (3.66 g, 19.81 mmol) and N,N-diisopropylethylamine (3.65 mL, 19.81 mmol) in sealed tube at RT under argon atmosphere; the mixture was heated to 120° C. and stirred for 36 h. The reaction was monitored by TLC; after completion of the reaction, the volatiles were removed, in vacuo to obtain the crude product. The crude product was purified through silica gel column chromatography using 10% EtOAc/hexanes to afford compound 12 (4 g, 73%) as a white solid. TLC: 10% EtOAc/hexanes ($R_f$ 0.8); $^1$H-NMR (CDCl$_3$, 400 MHz): δ 7.30-7.28 (m, 2H), 7.03 (t, J=8.4 Hz, 2H), 6.32 (br s, 1H), 5.79 (s, 1H), 3.77 (t, J=5.2 Hz, 4H), 3.49-3.46 (m, 4H), 2.72-2.61 (m, 1H), 1.48 (s, 9H), 1.18 (d, J=6.8 Hz, 6H).

Synthesis of N—(4-fluorophenyl)-6-isopropyl-2-(piperazin-1-yl)pyrimidin-4-amine (13)

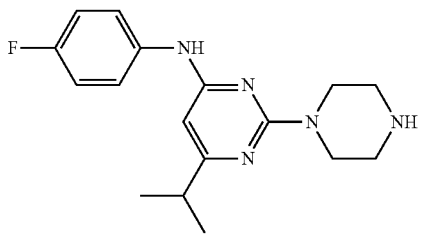

To a stirred solution of compound 12 (500 mg, 1.2 mmol) in CH$_2$Cl$_2$ (10 mL) was added 4 N HCl in 1,4-dioxane (4 mL) at 0° C. under argon atmosphere; the mixture was warmed to RT and stirred for 2 h. The reaction was monitored by TLC; after completion of the reaction, the volatiles were removed in vacuo. The residue was neutralized with 10% NaHCO$_3$ solution (20 mL) and extracted with EtOAc (2×30 mL). The combined organic extracts were dried over sodium sulfate, filtered, and concentrated in vocuo to afford compound 13 (340 mg, 90%) as an off-white solid. TLC: 10% CH$_3$OH/CH$_2$Cl$_2$ ($R_f$ 0.2); $^1$H-NMR (DMSO-d$_6$, 400 MHz): δ 9.09 (s, 1H), 7.62-7.58 (m, 2H), 7.11 (t, J=8.8 Hz, 2H), 5.86 (s, 1H), 3.60 (t, 4.8 Hz, 4H), 2.71 (t, J=4.8 Hz, 4H), 2.67-2.58 (m, 1H), 1.18 (d, J=6.8 Hz, 6H).

Example 2

Synthesis of Target Compounds 1-22

Intermediates 6 and 13 were converted to final products either by using commercially available sulfonyl chlorides or by using prepared sulfonyl chlorides employing typical procedure A and the results are captured in Table 1 below.

Typical procedure A: To a stirred solution of compound 6 (40 mg, 0.14 mmol) in CH$_2$Cl$_2$ (5 mL) under argon atmosphere were added pyridine (0.06 ml, 0.70 mmol), and sulfonyl chloride (29.5 mg, 0.15 mmol) at 0° C.; warmed to RT and stirred for 4 h. The reaction was monitored by TLC; after completion the reaction, the reaction mixture was diluted with CH$_2$Cl$_2$ (30 mL), washed with water (15 mL), 1 N HCl (10 mL), 10% NaHCO$_3$ solution (15 mL), brine (15 mL), dried over sodium sulfate, filtered and concentrated in vacuo to obtain the crude product. The precipitated material was either directly dried in vacuo or triturated or purified by column chromatography to afford the desired target compounds.

TABLE 1

| Target Cmpd. No. | Structure | Procedure, Intermediate | Rx. Yield | Mass Spec. Found | Mass Spec. Calculated | ¹H-NMR |
|---|---|---|---|---|---|---|
| 1 | 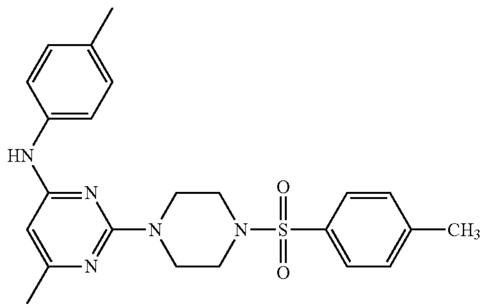 [SMILES: Cc1ccc(Nc2cc(C)nc(N3CCN(S(=O)(=O)c4ccc(C)cc4)CC3)n2)cc1] | A, 6 | 41% | 438.6 (M⁺ + 1); | 437.19 for $C_{23}H_{27}N_5O_2S$ | ¹H-NMR (DMSO-$d_6$, 400 MHz): δ 9.00 (s, 1H), 7.62 (d, J = 8.0 Hz, 2H), 7.43-7.38 (m, 4H), 7.08 (d, J = 8.0 Hz, 2H), 5.86 (s, 1H), 3.77 (t, J = 4.8 Hz, 4H), 2.89 (t, J = 4.8 Hz, 4H), 2.38 (s, 3H), 2.24 (s, 3H), 2.08 (s, 3H) |
| 2 | 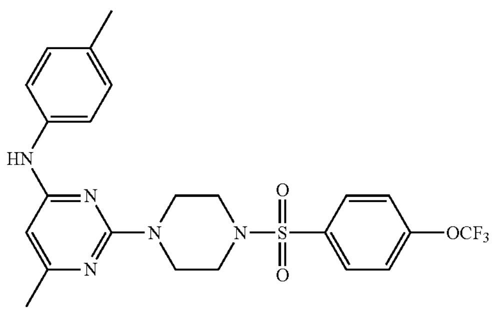 [SMILES: Cc1ccc(Nc2cc(C)nc(N3CCN(S(=O)(=O)c4ccc(OC(F)(F)F)cc4)CC3)n2)cc1] | A, 6 | 21% | 508.6 (M⁺ + 1); | 507.16 for $C_{23}H_{24}F_3N_5O_3S$ | ¹H-NMR (DMSO-$d_6$, 400 MHz): δ 9.00 (s, 1H), 7.89 (d, J = 6.8 Hz, 2H), 7.61 (d, J = 8.0 Hz, 2H), 7.40 (d, J = 8.4 Hz, 2H), 7.08 (d, J = 8.0 Hz, 2H), 5.87 (s, 1H), 3.78 (t, J = 5.2 Hz, 4H), 2.97 (t, J = 4.8 Hz, 4H), 2.24 (s, 3H), 2.09 (s, 3H) |
| 3 | 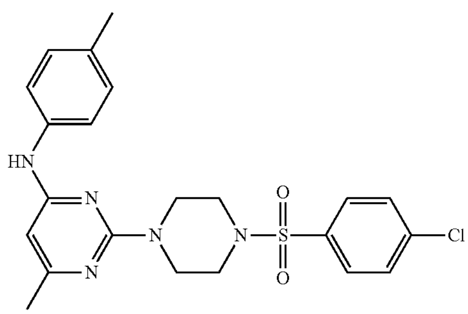 [SMILES: Cc1ccc(Nc2cc(C)nc(N3CCN(S(=O)(=O)c4ccc(Cl)cc4)CC3)n2)cc1] | A, 6 | 39% | 458.7 (M⁺ + 1) | 457.13 for $C_{22}H_{24}ClN_5O_2S$ | ¹H-NMR (DMSO-$d_6$, 400 MHz): δ 9.00 (s, 1H), 7.75 (d, J = 6.8 Hz, 2H), 7.69 (d, J = 6.8 Hz, 2H), 7.39 (d, J = 8.4 Hz, 2H), 7.08 (d, J = 8.4 Hz, 2H), 5.87 (s, 1H), 3.78 (t, J = 4.4 Hz, 4H), 2.95 (t, J = 4.8 Hz, 4H), 2.24 (s, 3H), 2.09 (s, 3H); |
| 4 | 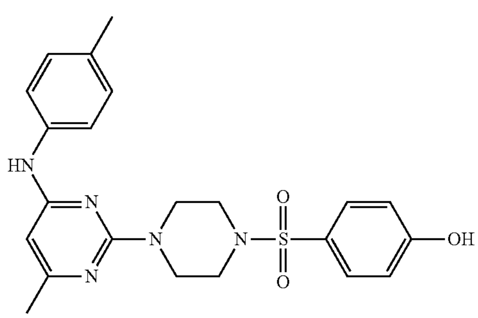 [SMILES: CCOc1ccc(S(=O)(=O)N2CCN(c3nc(C)cc(Nc4ccc(C)cc4)n3)CC2)cc1] | A, 6 | 33% | 490.4 (M⁺ + 1); | 439.17 for $C_{22}H_{25}N_5O_3S$ | ¹H-NMR (DMSO-$d_6$, 400 MHz): δ 10.51 (s, 1H), 9.00 (s, 1H), 7.56 (d, J = 8.8 Hz, 2H), 7.40 (d, J = 8.4 Hz, 2H), 7.08 (d, J = 8.4 Hz, 2H), 6.93 (d, J = 8.8 Hz, 2H), 5.86 (s, 1H), 3.76 (t, J = 4.8 Hz, 4H), 2.86 (t, J = 4.8 Hz, 4H), 2.24 (s, 3H), 2.09 (s, 3H); |

TABLE 1-continued

| Target Cmpd. No. | Structure | Procedure, Intermediate | Rx. Yield | Mass Spec. Found | Mass Spec. Calculated | $^1$H-NMR |
|---|---|---|---|---|---|---|
| 5 | *[structure: 4-methylanilino pyrimidine linked to piperazine-sulfonyl-4-ethylphenyl]* | A, 6 | 24% | 452.7 (M$^+$ + 1); | 451.20 for $C_{24}H_{29}N_5O_2S$ | $^1$H-NMR (DMSO-$d_6$, 400 MHz): δ 9.00 (s, 1H), 7.64 (d, J = 8.4 Hz, 2H), 7.46 (d, J = 8.4 Hz, 2H), 7.39 (d, J = 8.4 Hz, 2H), 7.08 (d, J = 8.4 Hz, 2H), 5.86 (s, 1H), 3.77 (t, J = 4.8 Hz, 4H), 2.89 (t, J = 4.8 Hz, 4H), 2.71-2.65 (m, 2H), 2.21 (s, 3H), 2.08 (s, 3H), 1.18 (t, J = 7.6 Hz, 3H); |
| 6 | *[structure: 4-methylanilino pyrimidine linked to piperazine-sulfonyl-4-isopropylphenyl]* | A, 6 | 66% | 466.7 (M$^+$ + 1); | 465.22 for $C_{25}H_{31}N_5O_2S$ | $^1$H-NMR (DMSO-$d_6$, 400 MHz): δ 9.01 (s, 1H), 7.66 (d, J = 8.4 Hz, 2H), 7.49 (d, J = 8.4 Hz, 2H), 7.39 (d, J = 8.4 Hz, 2H), 7.08 (d, J = 8.0 Hz, 2H), 5.86 (s, 1H), 3.77 (t, J = 4.8 Hz, 4H), 3.01-2.94 (m, 1H), 2.90 (t, J = 4.8 Hz, 4H), 2.24 (s, 3H), 2.08 (s, 3H), 1.20 (d, J = 6.8 Hz, 6H); |
| 7 | *[structure: 4-methylanilino pyrimidine linked to piperazine-sulfonyl-3-methylphenyl]* | A, 6 | 46% | 438.6 (M$^+$ + 1); | 437.19 for $C_{23}H_{27}N_5O_2S$ | $^1$H-NMR (DMSO-$d_6$, 400 MHz): δ 9.01 (s, 1H), 7.55-7.50 (m, 4H), 7.39 (d, J = 8.4 Hz, 2H), 7.08 (d, J = 8.4 Hz, 2H), 5.86 (s, 1H), 3.77 (t, J = 4.8 Hz, 4H), 2.91 (t, J = 4.8 Hz, 4H), 2.39 (s, 3H), 2.24 (s, 3H), 2.08 (s, 3H); |
| 8 | *[structure: 4-methylanilino pyrimidine linked to piperazine-sulfonyl-4-ethoxyphenyl]* | A, 6 | 59% | 468.6 (M$^+$ + 1); | 467.20 for $C_{24}H_{29}N_5O_3S$ | $^1$H-NMR (DMSO-$d_6$, 400 MHz): δ 9.00 (s, 1H), 7.65 (d, J = 8.8 Hz, 2H), 7.39 (d, J = 8.4 Hz, 2H), 7.09 (d, J = 8.8 Hz, 4H), 5.86 (s, 1H), 4.10 (q, 2H), 3.77 (t, J = 4.8 Hz, 4H), 2.87 (t, J = 4.8 Hz, 4H), 2.24 (s, 3H), 2.08 (s, 3H), 1.32 (t, J = 7.2 Hz, 3H); |

TABLE 1-continued

| Target Cmpd. No. | Structure | Procedure, Intermediate | Rx. Yield | Mass Spec. Found | Mass Spec. Calculated | $^1$H-NMR |
|---|---|---|---|---|---|---|
| 9 | 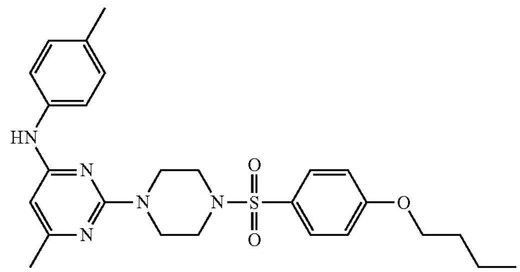 [SMILES: CCCCOc1ccc(S(=O)(=O)N2CCN(c3nc(C)cc(Nc4ccc(C)cc4)n3)CC2)cc1] | A, 6 | 43% | 496.7 (M$^+$ + 1); | 495.23 for C$_{26}$H$_{33}$N$_5$O$_3$S | $^1$H-NMR (DMSO-d$_6$, 400 MHz): δ 9.01 (s, 1H), 7.65 (d, J = 8.8 Hz, 2H), 7.39 (d, J = 8.4 Hz, 2H), 7.12-7.07 (m, 4H), 5.86 (s, 1H), 4.03 (t, J = 6.8 Hz, 2H), 3.77 (t, J = 4.8 Hz, 4H), 2.87 (t, J = 4.8 Hz, 4H), 2.24 (s, 3H), 2.08 (s, 3H), 1.72-1.65 (m, 2H), 1.44-1.38 (m, 2H), 0.91 (t, J = 7.6 Hz, 3H); |
| 10 | 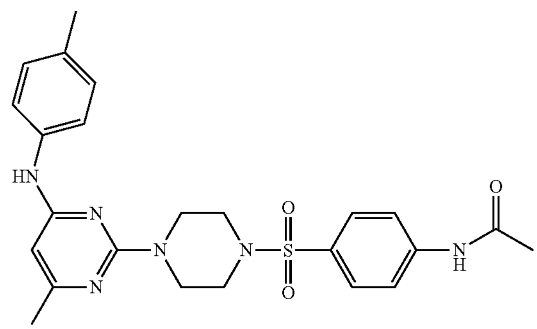 [SMILES: CC(=O)Nc1ccc(S(=O)(=O)N2CCN(c3nc(C)cc(Nc4ccc(C)cc4)n3)CC2)cc1] | A, 6 | 92% | 481.2022 | 476.2008 for C$_{24}$H$_{29}$N$_6$O$_3$S (M + H)$^+$ | $^1$H NMR (400 MHz, CDCl$_3$) δ 7.71-7.61 (m, 4H), 7.58 (s, 1H), 7.12 (d, J = 1.5 Hz, 4H), 6.34 (s, 1H), 5.80 (s, 1H), 3.87 (t, J = 4.9 Hz, 4H), 3.00 (t, J = 5.0 Hz, 4H), 2.31 (s, 3H), 2.19 (s, 3H), 2.13 (s, 3H) |
| 11 | 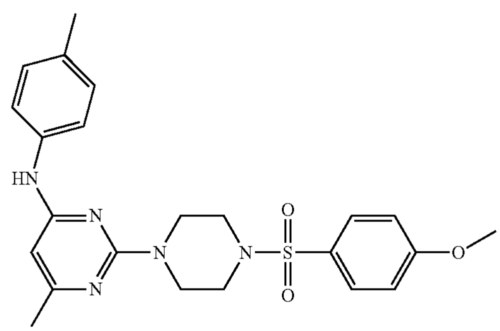 [SMILES: COc1ccc(S(=O)(=O)N2CCN(c3nc(C)cc(Nc4ccc(C)cc4)n3)CC2)cc1] | A, 6 | 59% | 454.1926 | 454.1913 for C$_{23}$H$_{28}$N$_5$O$_3$S (M + H)$^+$ | $^1$H NMR (400 MHz, CDCl$_3$) δ 7.69-7.55 (m, 2H), 7.08 (s, 4H), 6.96-6.86 (m, 2H), 6.23 (s, 1H), 5.75 (s, 1H), 3.83 (t, J = 5.1 Hz, 4H), 3.79 (s, 3H), 2.95 (t, J = 5.0 Hz, 4H), 2.26 (s, 3H), 2.14-2.02 (m, 3H). |
| 12 | 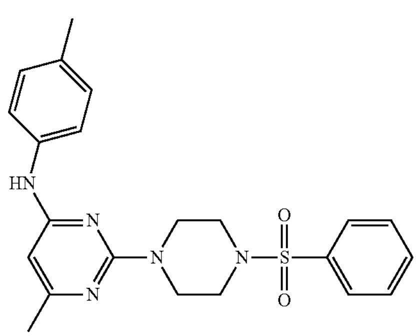 [SMILES: Cc1ccc(Nc2cc(C)nc(N3CCN(S(=O)(=O)c4ccccc4)CC3)n2)cc1] | A, 6 | 73% | 424.1810 | 424.1807 for C$_{22}$H$_{26}$N$_5$O$_2$S (M + H)$^+$ | $^1$H NMR (400 MHz, CDCl$_3$) δ 7.74 (d, J = 7.6 Hz, 2H), 7.60-7.44 (m, 3H), 7.13 (s, 4H), 6.29 (s, 1H), 5.81 (s, 1H), 3.89 (s, 4H), 3.03 (t, J = 5.1 Hz, 4H), 2.32 (s, 3H), 2.14 (br s, 3H). |

TABLE 1-continued

| Target Cmpd. No. | Structure | Procedure, Intermediate | Rx. Yield | Mass Spec. Found | Mass Spec. Calculated | ¹H-NMR |
|---|---|---|---|---|---|---|
| 13 | 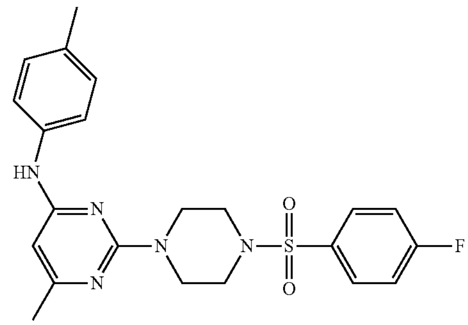 [SMILES: Cc1ccc(Nc2cc(C)nc(N3CCN(S(=O)(=O)c4ccc(F)cc4)CC3)n2)cc1] | A, 6 | 64% | 442.1731 | 442.1713 for $C_{22}H_{25}N_5O_4FS$ $(M + H)^+$ | ¹H NMR (400 MHz, CDCl₃) δ 7.81-7.70 (m, 2H), 7.22-7.07 (m, 6H), 6.29 (s, 1H), 5.81 (s, 1H), 3.89 (t, J = 5.1 Hz, 4H), 3.02 (t, J = 5.0 Hz, 4H), 2.32 (s, 3H), 2.15 (s, 3H). |
| 14 | 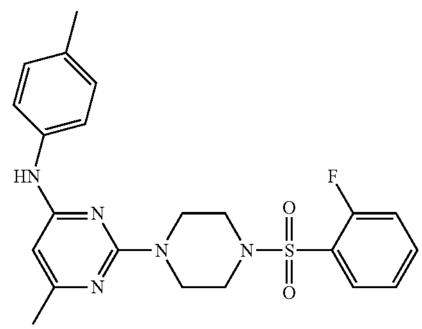 [SMILES: Cc1ccc(Nc2cc(C)nc(N3CCN(S(=O)(=O)c4ccccc4F)CC3)n2)cc1] | A, 6 | 55% | 442.2 $(M + H)^+$ | 442.1713 for $C_{22}H_{25}N_5O_2FS$ $(M + H)^+$ | ¹H NMR (500 MHz, CDCl₃) δ 7.85 (t, 1H), 7.59-7.54 (m, 1H), 7.28 (dd, J = 7.7, 0.9 Hz, 1H), 7.22-7.12 (m, 5H), 6.32 (s, 1H), 5.84 (s, 1H), 3.91 (t, 4H), 3.23 (t, 4H), 2.34 (s, 3H), 2.17 (s, 3H). |
| 15 | 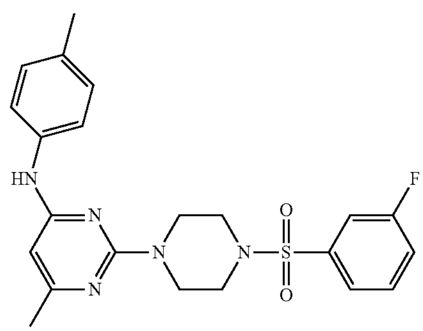 [SMILES: Cc1ccc(Nc2cc(C)nc(N3CCN(S(=O)(=O)c4cccc(F)c4)CC3)n2)cc1] | A, 6 | 67% | 442.2 $(M + H)^+$ | 442.1713 for $C_{22}H_{25}N_5O_2FS$ $(M + H)^+$ | ¹H NMR (500 MHz, CDCl₃) δ 7.68-7.36 (m, 5H), 7.29-7.26 (m, 1H), 7.26-7.24 (m, 2H), 6.50 (s, 1H), 5.94 (s, 1H), 4.02 (t, 4H), 3.18 (t, 4H), 2.45 (s, 3H), 2.27 (s, 3H). |
| 16 | 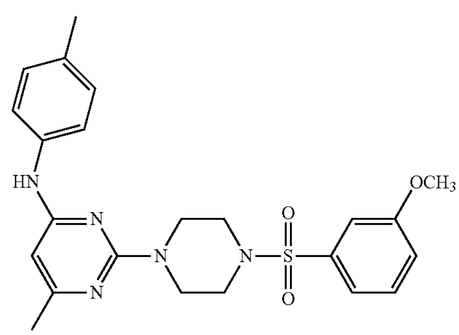 [SMILES: COc1cccc(S(=O)(=O)N2CCN(c3nc(C)cc(Nc4ccc(C)cc4)n3)CC2)c1] | A, 6 | 60% | 454.2 $(M + H)^+$ | 454.1913 for $C_{23}H_{28}N_5O_3S$ $(M + H)^+$ | ¹H NMR (500 MHz, CDCl₃) δ 7.53 (t, J = 8.0 Hz, 1H), 7.45 (d, J = 7.7 Hz, 3H), 7.38 (d, J = 1.4 Hz, 4H), 7.29-7.27 (m, J = 6.1 Hz, 1H), 7.26-7.20 (m, 4H), 6.43 (s, 1H), 5.94 (s, 1H), 4.02 (t, 4H), 3.96 (s, 3H), 3.18 (t, J = 4.8 Hz, 4H), 2.45 (s, 3H), 2.27 (s, 3H). |

TABLE 1-continued

| Target Cmpd. No. | Structure | Procedure, Intermediate | Rx. Yield | Mass Spec. Found | Mass Spec. Calculated | ¹H-NMR |
|---|---|---|---|---|---|---|
| 17 | 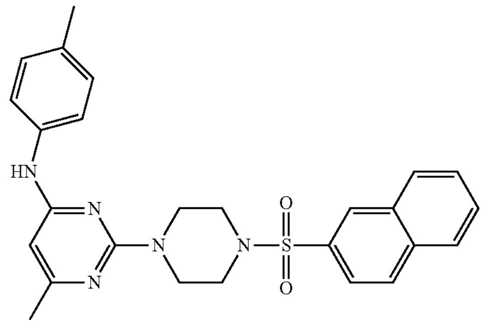 [SMILES: Cc1ccc(Nc2cc(C)nc(N3CCN(S(=O)(=O)c4ccc5ccccc5c4)CC3)n2)cc1] | A, 6 | 55% | 474.2 (M + H)⁺ | 474.1964 for $C_{26}H_{28}N_5O_2S$ (M + H)⁺ | ¹H NMR (500 MHz, CDCl₃) δ 8.47 (s, 1H), 8.10 (t, 3H), 8.04 (d, J = 8.0 Hz, 1H), 7.89) (dd, J = 8.7, 1.8 Hz, 1H), 7.80-7.73 (m, 3H), 7.40 (s, 2H), 6.43 (s, 1H), 5.93 (s, 1H), 4.05 (t, 4H), 3.25 (t, 4H), 2.46 (s, 3H), 2.26 (s, 3H). |
| 18 | 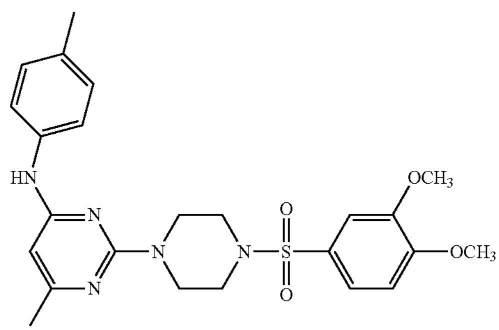 [SMILES: COc1ccc(S(=O)(=O)N2CCN(c3nc(C)cc(Nc4ccc(C)cc4)n3)CC2)cc1OC] | A, 6 | 50% | 484.2 (M + H)⁺ | 484.2019 for $C_{24}H_{30}N_5O_4S$ (M + H)⁺ | ¹H NMR (400 MHz, CDCl₃) δ 7.49 (dd, J = 8.4, 2.1 Hz, 1H), 7.38 (s, 1H), 7.32 (d, J = 2.0 Hz, 1H), 7.29-7.26 (m, 2H), 7.24 (s, 1H), 7.05 (d, J = 8.5 Hz, 2H), 6.43 (s, 1H), 5.94 (s, 1H), 4.05-4.01 (m, J = 7.9, 3.9 Hz, 10H), 3.16 (t, 4H), 2.45 (s, 3H), 2.28 (s, 3H). |
| 19 | 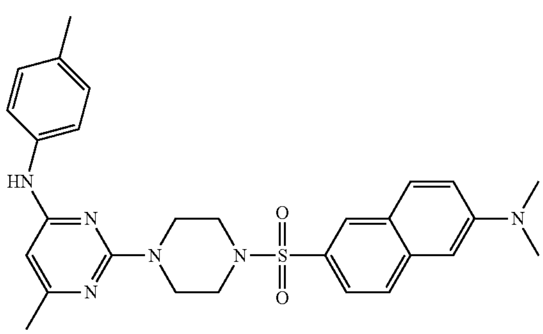 [SMILES: Cc1ccc(Nc2cc(C)nc(N3CCN(S(=O)(=O)c4ccc5cc(N(C)C)ccc5c4)CC3)n2)cc1] | A, 6 | 61% | 517.3 (M + H)⁺ | 517.2386 for $C_{24}H_{33}N_6O_2S$ (M + H)⁺ | ¹H NMR (400 MHz, CDCl₃) δ 8.13 (d, J = 1.3 Hz, 1H), 7.78 (d, J = 9.2 Hz, 1H), 7.67 (d, J = 8.7 Hz, 1H), 7.59 (dd, J = 8.7, 1.8 Hz, 1H), 7.20 (dd, J = 9.1, 2.5 Hz, 1H), 7.13 (s, 3H), 6.86 (d, J = 2.4 Hz, 1H), 6.28 (s, 1H), 5.79 (s, 1H), 3.90 (t, 4H), 3.11-3.04 (m, 10H), 2.32 (s, 3H), 2.13 (s, 3H). |

TABLE 1-continued

| Target Cmpd. No. | Structure | Procedure, Intermediate | Rx. Yield | Mass Spec. Found | Mass Spec. Calculated | $^1$H-NMR |
|---|---|---|---|---|---|---|
| 20 | 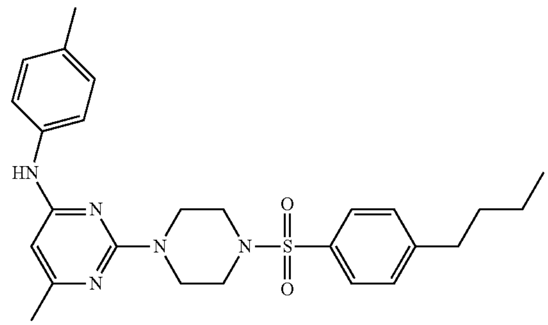 [SMILES: CCCCc1ccc(S(=O)(=O)N2CCN(c3nc(C)cc(Nc4ccc(C)cc4)n3)CC2)cc1] | A, 6 | 40% | 480.1 (M + H)$^+$ | 480.2433 for $C_{26}H_{34}N_5O_2S$ (M + H)$^+$ | $^1$H NMR (400 MHz, CDCl$_3$) δ 7.65 (d, J = 7.8 Hz, 2H), 7.31 (d, J = 7.8 Hz, 2H), 7.14 (s, 4H), 6.29 (s, 1H), 5.82 (s, 1H), 3.90 (s, 4H), 3.04 (t, 4H), 2.66 (t, J = 7.6 Hz, 2H), 2.33 (s, 3H), 2.15 (s, 3H), 1.64-1.59 (m, 2H), 1.35 (dd, J = 14.7, 7.4 Hz, 2H), 0.93 (t, J = 7.3 Hz, 3H). |
| 21 | 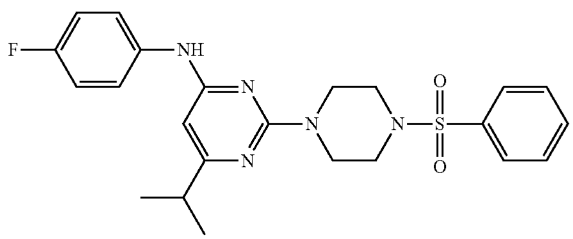 [SMILES: CC(C)c1cc(Nc2ccc(F)cc2)nc(N2CCN(S(=O)(=O)c3ccccc3)CC2)n1] | A, 13 | 31% | 456.5 (M$^+$ + 1) | 455.18 for $C_{23}H_{26}FN_5O_2S$ | $^1$H-NMR (DMSO-d$_6$, 400 MHz): δ 9.16 (s, 1H), 7.76-7.69 (m, 3H), 7.63 (t, J = 7.2 Hz, 2H), 7.56-7.52 (m, 2H), 7.11 (t, J = 8.8 Hz, 2H), 5.87 (s, 1H), 3.79-3.77 (m, 4H), 2.94 (t, J = 4.8 Hz, 4H), 2.66-2.55 (m, 1H), 1.11 (d, J = 6.8 Hz, 6H). |
| 22 | 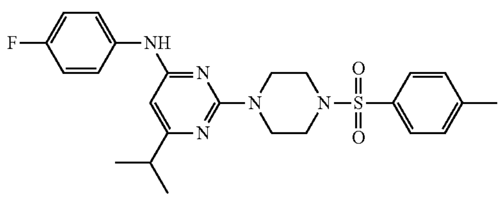 [SMILES: Cc1ccc(S(=O)(=O)N2CCN(c3nc(Nc4ccc(F)cc4)cc(C(C)C)n3)CC2)cc1] | A, 13 | 41% | 470.1 (M$^+$ + 1) | 469.19 for $C_{24}H_{28}FN_5O_2S$ | $^1$H-NMR (DMSO-d$_6$, 400 MHz): δ 9.16 (s, 1H), 7.63 (d, J = 8.0 Hz, 2H), 7.56-7.52 (m, 2H), 7.43 (d, J = 8.0 Hz, 2H), 7.11 (t, J = 8.8 Hz, 2H), 5.87 (s, 1H), 3.78 (t, J = 4.8 Hz, 4H), 2.90 (t, J = 4.8 Hz, 4H), 2.62-2.53 (m, 1H), 2.38 (s, 3H), 1.11 (d, J = 6.8 Hz, 6H). |

Example 3

Synthesis of Target Compounds 23 & 24

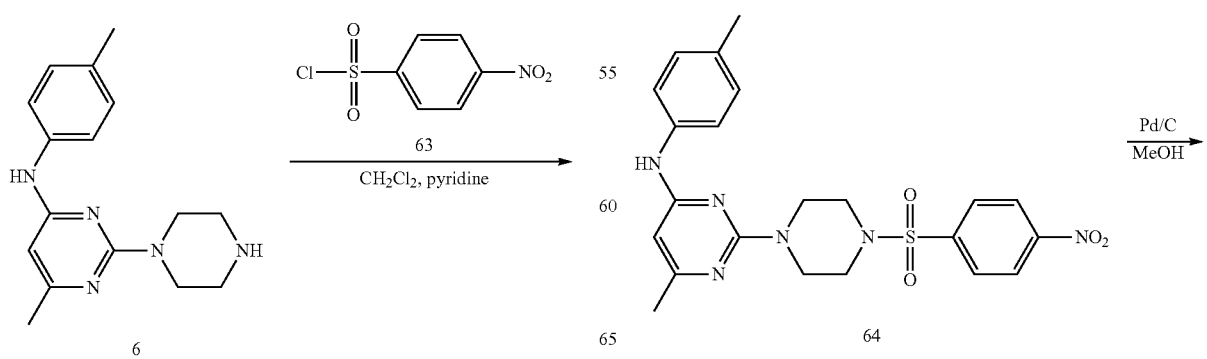

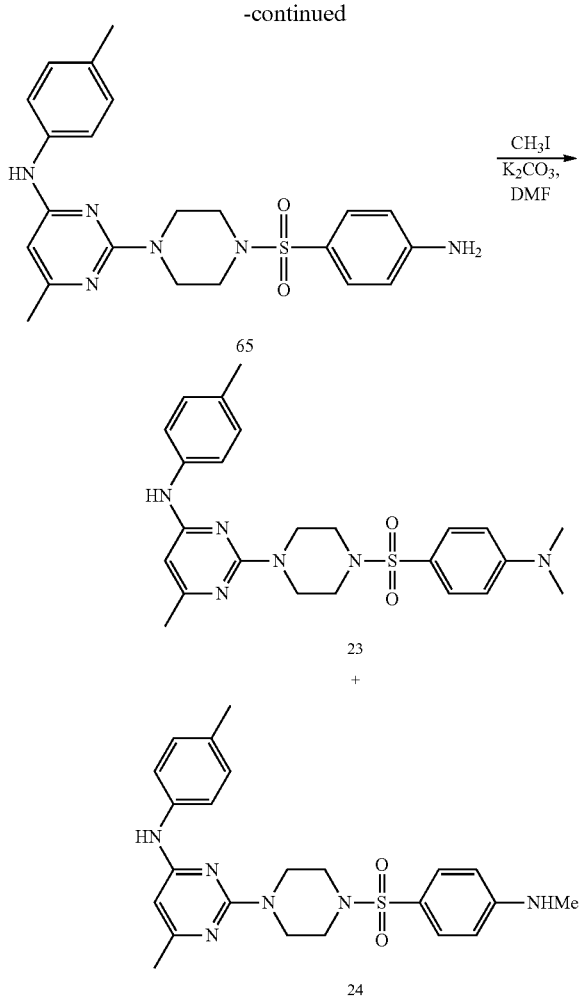

Synthesis of 6-methyl-2-(4-((4-nitrophenyl)sulfonyl piperazin-1-yl)-N-(p-tolyl)pyrimidin-4-amine (64): To a stirred solution of compound 6 (100 mg, 0.35 mmol) in CH$_2$Cl$_2$ (5 mL) under argon atmosphere were added pyridine (0.15 mL, 1.76 mmol) and 4-nitrobenzenesulfonyl chloride 63 (78 mg, 0.35 mmol) at 0° C.; warmed to RT and stirred for 4 h. The reaction was monitored by TLC; after completion of the reaction, the reaction mixture was diluted with CH$_2$Cl$_2$ (30 mL), washed with 1 N HCl (15 mL), 10% NaHCO$_3$ solution (20 mL), water (20 mL), dried over sodium sulfate, filtered and concentrated in vacuo to obtain the crude product. The crude product was washed with diethyl ether (2×5 mL) and n-pentane (2×5 mL) and dried in vacuo to afford compound 64 (110 mg, 67%) as a white solid. TLC: 5% MeOH/CH$_2$Cl$_2$ (R$_f$ 0.8); $^1$H-NMR (DMSO-d$_6$, 400 MHz): δ 9.00 (s, 1H), 8.41 (d, J=8.8 Hz, 2H), 8.01 (d, J=8.8 Hz, 2H), 7.38 (d, J=8.4 Hz, 2H), 7.09 (d, J=8.4 Hz, 2H), 5.86 (s, 1H), 3.79 (s, J=5.2 Hz, 4H), 3.02 (t, J=4.8 Hz, 4H), 2.24 (s, 3H), 2.08 (s, 3H).

Synthesis of 6-methyl -2-(4-((4-nitrophenyl)sulfonyl piperazin-1-yl)-N-(p-tolyl) pyrimidin-4-amine (65): To a stirred solution of compound 64 (100 mg, 0.21 mmol) in MeOH (5 mL) under argon atmosphere was added 10% Pd/C (30 mg) at RT; the mixture was stirred under hydrogen atmosphere (balloon pressure) for 4 h. The reaction was monitored by TLC; after completion of the reaction, the reaction mixture was filtered through celite, washed with CH$_2$Cl$_2$, (2×20 mL) and the filtrate was concentrated in vacuo to obtain the crude compound 65 (73 mg, 78%) as an off-white solid. TLC: 5% MeOH/CH$_2$Cl$_2$ (R$_f$ 0.5); $^1$H-NMR (DMSO-d$_6$, 400 MHz): δ 8.99 (s, 1H), 7.40 (t, 8.4 Hz, 2H), 7.35 (d, J=8.8 Hz, 2H), 7.08 (d, J=8.0 Hz, 2H), 6.62 (d, J=8.4 Hz, 2H), 6.05 (br s, 2H), 5.86 (s, 1H), 3.75 (t, J=5.2 Hz, 4H), 2.82 (t, J=5.2 Hz, 4H), 2.24 (s, 3H), 2.09 (s, 3H).

Synthesis of 2-(4-((4-dimethylamino) phenyl) sulfonyl) piperazin-1-yl)-6-methyl-N-(p-tolyl)pyrimidin-4-amine (target compound 23) & 6-methyl-2-(4-((4-(methylamino) phenyl)sulfonyl)piperazin-1-yl)-N-(p-tolyl)pyrimidin-4-amine (target compound 24): To a stirred solution of compound 65 (140 mg, 0.31 mmol) in N,N-dimethylformamide (DMF; 5 mL) under argon atmosphere were added potassium carbonate (110 mg, 0.79 mmol), methyl iodide (0.05 mL, 0.79 mmol) at 0° C.; warmed to 50° C. and stirred for 16 h. The reaction was monitored by TLC; after completion of the reaction, the reaction mixture was diluted with ice cold water (10 mL) and the precipitated solid was filtered, washed with ether (2×5 mL) to obtain the crude product, which was purified by preparative HPLC to afford target compounds 23 (30 mg, 20%) & 24 (25 mg, 17%) as off-white solids.

Analytical data of target compound 23: TLC: 5% MeOH/CH$_2$Cl$_2$ (R$_f$ 0.6); $^1$H-NMR (DMSO-d$_6$, 400 MHz): δ 9.00 (s, 1H), 7.48 (d, J=9.2 Hz, 2H), 7.39 (d, J=8.4 Hz, 2H), 7.08 (d, J=8.0 Hz, 2H), 6.77 (d, J=8.8 Hz, 2H), 5.85 (s, 1H), 3.76 (t, J=5.2 Hz, 4H), 2.98 (s, 6H), 2.82 (t, J=4.8 Hz, 4H), 2.24 (s, 3H), 2.08 (s, 3H); LC-MS: 99.37%; 467.0 (M$^+$+1); (column; X-select CSH C-18, (50×3.0 mm, 3.5 μm); RT 3.06 min. 0.05% TFA (Aq): ACN; 0.8 mL/min); UPLC (purity): 99.15%; (column: Acquity BEH C-18 (50×2.1 mm, 1.7μ); RT2.14 min. ACN: 0.025% TFA (Aq); 0.5 mL/min) (IP13090223).

Analytical data of target compound 24: TLC: 5% MeOH/CH$_2$Cl$_2$ (R$_f$ 0.5); $^1$H-NMR (DMSO-d$_6$, 400 MHz): δ 8.99 (s, 1H), 7.40 (d, J=8.8 Hz, 4H), 7.06 (d, J=8.0 Hz, 2H), 6.65-6.63 (m, 1H), 6.61 (d, J=8.8 Hz, 2H), 5.86 (s, 1H), 3.76 (t, J=4.8 Hz, 4H), 2.82 (t, J=4.8 Hz, 4H), 2.70 (d, J=5.2 Hz, 3H), 2.24 (s, 3H), 2.08 (s, 3H); LC-MS: 93.74%; 453.0 (M$^+$+1); (column; X-select CSH C-18, (50×3.0 mm, 3.5 μm); RT 2.92 min. 0.05% TFA (Aq): ACN; 0.8 mL/min); UPLC (purity): 92.23%; (column: Acquity BEH C-18 (50×2.1 mm, 1.7μ); RT 2.04 min. ACN: 0.025% TFA (Aq); 0.5 mL/min) (IP13090222).

Example 4

Synthesis of Target Compounds 25 & 26

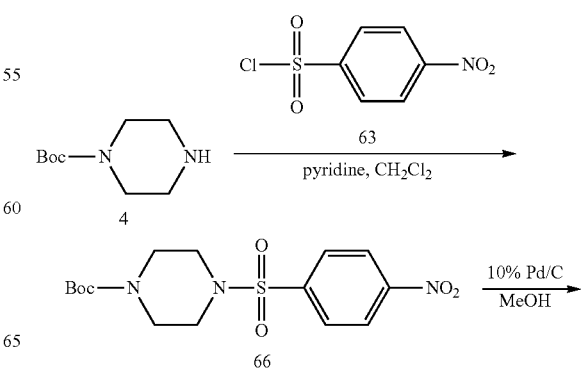

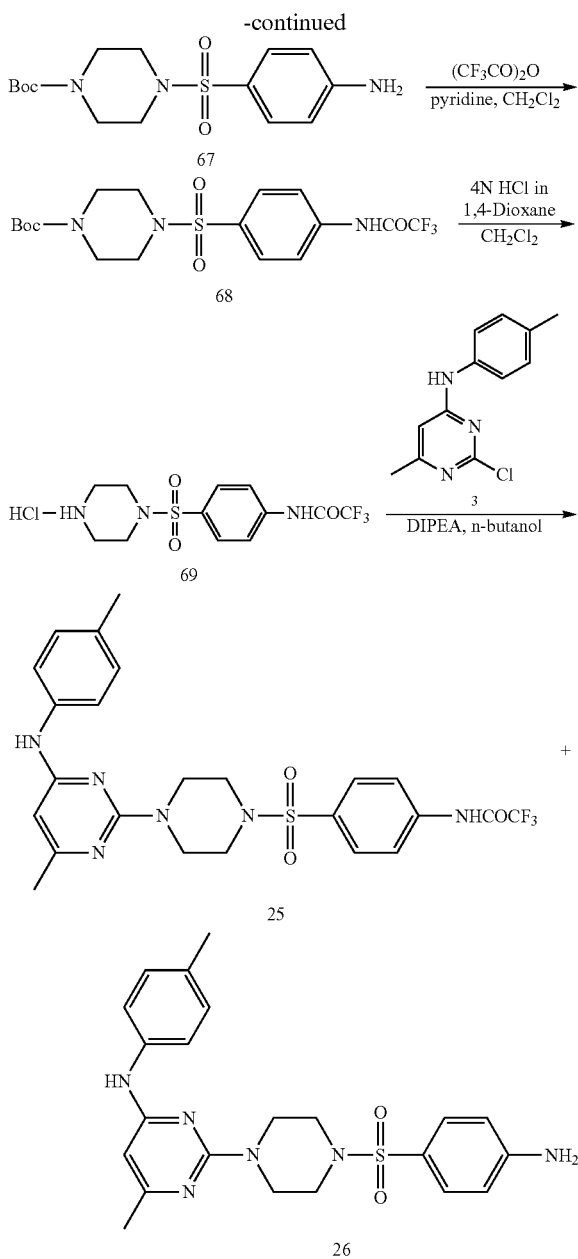

Synthesis of tert-butyl 4-((4-nitrophenyl)sulfonyl)piperazine-1-carboxylate (66): To a stirred solution of tert-butyl piperazine-1-carboxylate 4 (500 mg, 2.68 mmol) in CH$_2$Cl$_2$ (10 mL) wider argon atmosphere were added pyridine (1.1 mL, 13.4 mmol), 4-nitrobenzenesulfonyl chloride 63 (594 mg, 2.68 mmol) at 0° C.; warmed to RT and stirred for 4 h. The reaction was monitored by TLC; after completion of the reaction, the reaction mixture was diluted with EtOAc (30 mL), washed with water (20 mL), 1 N HCl (15 mL), 10% NaHCO$_3$ solution (20 mL), brine (20 mL), dried over sodium sulfate, filtered and concentrated in vacuo to obtain the crude product. The crude product was washed with diethyl ether (2×10 mL) and n-pentane (2×10 mL) and dried in vacuo to afford compound 66 (760 mg, 76%) as a white solid. TLC: 30% EtOAc/hexanes (R$_f$ 0.5); $^1$H-NMR (CDCl$_3$, 500 MHz): δ 8.39 (d, J=9.0 Hz, 2H), 7.94 (d, J=9.0 Hz, 2H), 3.53 (t, J=5.0 Hz, 4H), 3.04 (t, J=5.0 Hz, 4H), 1.40 (s, 9H).

Synthesis of tert-butyl 4-((4-aminophenyl) sulfonyl) piperazine-1-carboxylate (67): To a stirred solution of compound 66 (750 mg, 2.02 mmol) in MeOH (10 mL) under argon atmosphere was added 10% Pd/C (200 mg) at RT and stirred under hydrogen atmosphere (balloon pressure) for 6 h. The reaction was monitored by TLC; after completion of the reaction, the reaction mixture was filtered through celite, washed with CH$_2$Cl$_2$ (2×30 mL), and the filtrate was concentrated in vacuo to obtain the crude product. The crude product was washed with C$_2$Cl$_2$ (2×10 mL) to afford compound 67 (610 mg, 89%) as white solid, TLC: 30% EtOAc/hexanes (R$_f$ 0.3); $^1$H-NMR (CDCl$_3$, 400 MHz): δ 7.54 (d, 8.4 Hz, 2H), 6.78 (d, J=8.4 Hz, 2H), 3.49 (t, J=5.6 Hz, 4H), 2.93 (t, J=5.2 Hz, 4H), 1.41 (s, 9H).

Synthesis of tert-butyl-4-((4-(2,2,2-trifluoroacetamido) phenyl)sulfonyl)piperazine-1-carboxylate (68): To a stirred solution of compound 67 (100 mg, 0.29 mmol) in CH$_2$Cl$_2$ (3 mL) under argon atmosphere were added pyridine (0.04 mL, 0.58 mmol) and trifluoroacetic anhydride (0.04 mL, 0.29 mmol) at 0° C.; and stirred for 30 min. The reaction was monitored by TLC; after completion the reaction, the reaction mixture was diluted with water (20 mL) and extracted with CH$_2$Cl$_2$ (2×20 mL). The combined organic extracts were dried over sodium sulfite, filtered and concentrated in vacuo to obtain the crude product. The crude product was purified through silica gel column chromatography using 30% EtOAc/hexanes to afford compound 68 (105 mg, 82%) as white solid. TLC: 40% EtOAc/hexanes (R$_f$ 0.8); $^1$H-NMR (DMSO-d$_6$, 400 MHz): δ 11.64 (s, 1H), 7.95 (d, J=8.0 Hz, 2H), 7.78 (d, J=9.2 Hz, 2H), 3.38 (t, J=5.2 Hz, 4H), 2.85 (t, J=5.2 Hz, 4H), 1.33 (s, 9H).

Synthesis of 2,2,2-trifluoro-N-(4-(piperazin-1-ylsulfonyl)phenyl)acetamide hydrochloride (69): To a stirred solution of compound 68 (100 mg, 0.22 mmol) in CH$_2$Cl$_2$ (3 mL) was added 4 N HCl in 1,4-dioxane (2 mL) under argon atmosphere at 0° C. was stirred for 3 h. The reaction was monitored by TLC; after completion of the reaction, the volatiles were removed in vacuo to obtain the crude product. The crude product was triturated with diethyl ether (2×5 mL) and dried in vacuo to afford compound 69 (45 mg, HCl salt) as an off-white solid. TLC: 5% MeOH/CH$_2$Cl$_2$ (R$_f$ 0.2); $^1$H-NMR (DMSO-d$_6$, 500 MHz): δ 11.78 (br s, 1H), 9.05 (br s, 1H), 8.50 (d, J=6.8 Hz, 2H), 7.85 (d, J=7.2 Hz, 2H), 3.17-3.16 (m, 4H), 3.13-3.12 (m, 4H).

Synthesis of 2,2,2-trifluoro-N-(4-((4-(4-methyl-6-(p-tolylamino)pyrimidin-2-yl)piperazin-1-yl) sulfonyl)phenyl)acetamide (25) & 2,2,2-trifluoro-N-(4-((4-(4-methyl-6-(p-tolylamino)pyrimidin-2-yl) piperazin-1-yl)sulfonyl)phenyl) acetamide (26): To a stirred solution of compound 69 (70 mg, 0.29 mmol) in n-butanol (3 mL) under argon atmosphere were added compound 3 (100 mg, 0.29 mmol), diisopropylethylamine (0.13 mL, 0.74 mmol) at RT; warmed to 100° C. and stirred for 12 h. The reaction was monitored by TLC; after completion of the reaction, the volatiles were removed in vacuo to obtain crude. The crude product was purified through silica gel column chromatography using 30% EtOAc/hexanes to afford 25 (20 mg, 12%) & 26 (30 mg, 20%) as an off-white solid. Analytical data of 25: TLC: 40% EtOAc/hexanes (R$_f$ 0.6); $^1$H-NMR (DMSO-d$_6$, 400 MHz): δ 11.60 (s, 1H), 9.00 (s, 1H), 7.93 (d, J=9.2 Hz, 2H), 7.79 (d, J=8.8 Hz, 2H), 7.39 (d, J=8.4 Hz, 2H), 7.08 (d, J=8.4 Hz, 2H), 5.86 (s, 1H), 3.77 (t, J=5.2 Hz, 4H), 2.92 (t, J=4.8 Hz, 4H), 2.24 (s, 3H), 2.08 (s, 3H); LC-MS: 98.84%; 534.9 (M$^+$+1); (column: X-select CSH C-18, (50×3.0 mm, 3.5 μm); RT 3.13 min. 0.05% TFA (Aq): ACN; 8.0 mL/min); UPLC (purity): 97.15%; (column: Acquity BEH C-18 (50× 2.1 mm, 1.7μ); RT 2.13 min. ACN: 0.025% TFA (Aq); 0.5 mL/min) (IP13090981).

Analytical data of 26: TLC: 40% EtOAc/hexanes (R$_f$ 0.5); $^1$H-NMR (DMSO-d$_6$, 400 MHz): δ 8.99 (s, 1H), 7.40 (d, J=8.4 Hz, 2H), 7.35 (d, J=8.8 Hz, 2H), 7.08 (d, J=8.0 Hz, 2H), 6.62 (d, J=8.8 Hz, 2H), 6.05 (br s, 2H), 5.86 (s, 1H), 3.75 (t, J=4.8 Hz, 4H), 2.82 (t, J=4.8 Hz, 4H), 2.24 (s, 3H), 2.09 (s, 3H); LC-MS: 98.05%; 438.9 (M$^+$+1); (column: X-select CSH C-18, (50×3.0 mm, 3.5 μm); RT 2.81 min. 0.05% TFA (Aq): ACN; 0.8 mL/min); UPLC (purity): 95.75%; (column: Acquity BEH C-18 (50×2.1 mm, 1.7μ); RT 1.93 min. ACN: 0.025% TFA (Aq); 0.5 mL/min) (IP13100012).
Example 5
Synthesis of Target Compound 27
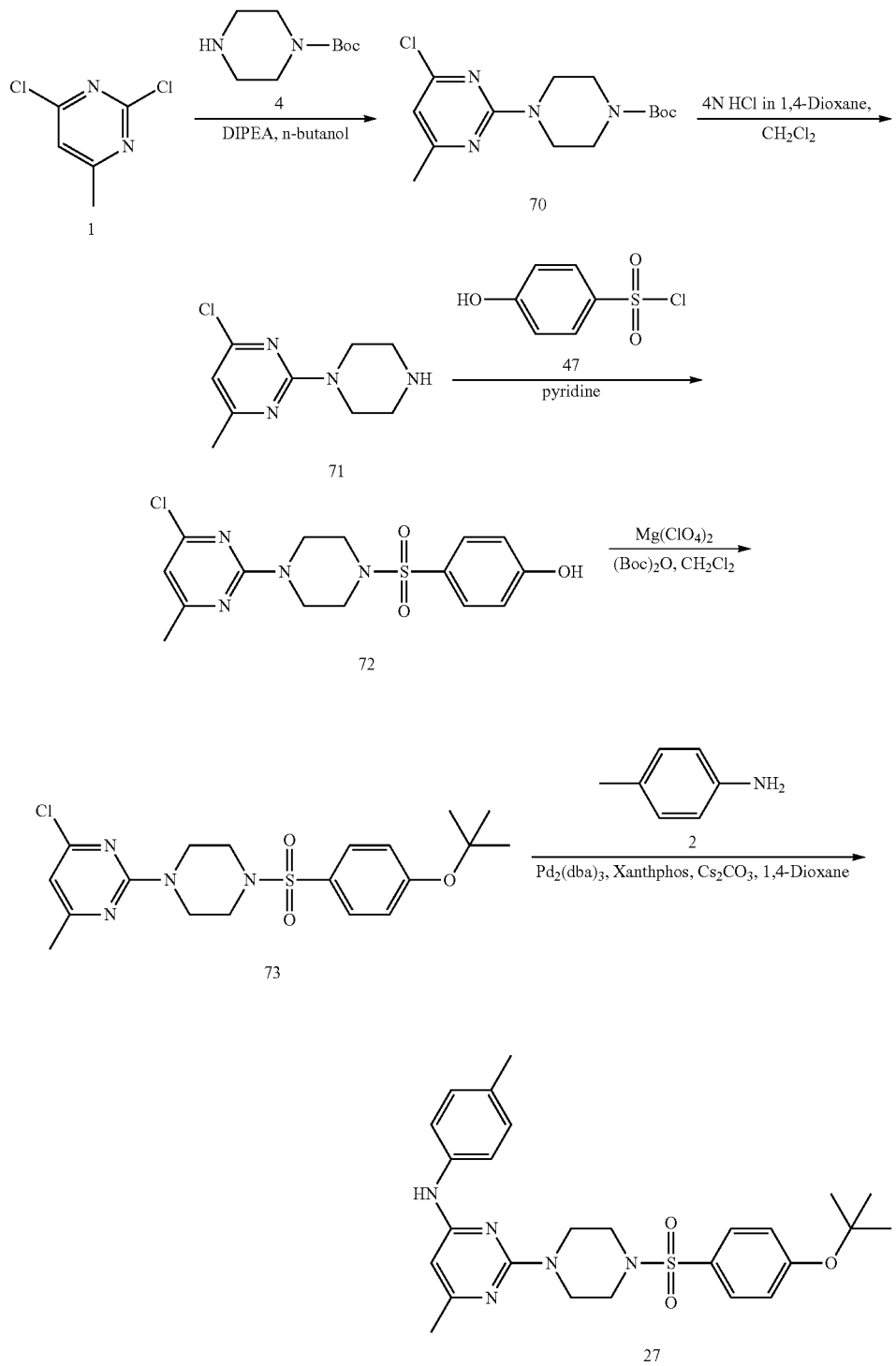

Synthesis of tert-butyl 4(4-chloro-6-methylpyrimidin-2-yl) piperazine-1-carboxylate (70): To a stirred solution of 2,4-dichloro-6-methylpyrimidine 1 (2 g, 12.26 mmol) in n-butanol (10 mL) under argon atmosphere were added tert-butyl piperazine-1-carboxylate 4 (2.74 g, 14.72 mmol), diisopropylethylamine (4.2 mL, 24.53 mmol) in a sealed tube at RT; warmed to 100° C. and stirred for 16 h. The reaction was monitored by TLC; after completion of the reaction, the reaction mixture was diluted with water (50 mL) and extracted with EtOAc (3×50 mL). The combined organic extracts dried over sodium sulfate, filtered and concentrated in vacuo to obtain crude. The crude product was purified through silica gel column chromatography using 15% EtOAc/hexanes to afford compound 70 (500 mg, 13%) as an off-white solid. TLC: 10% EtOAc/hexanes ($R_f$, 0.6); $^1$H-NMR (DMSO-$d_6$, 500 MHz): δ 6.66 (s, 1H), 3.69 (t, J=5.0 Hz, 4H), 3.38 (t, J=5.0 Hz, 4H), 2.28 (s, 3H), 1.41 (s, 9H).

Synthesis of 4-chloro-6-methyl-2-(piperazin-1-yl)pyrimidine (71): To a stirred solution of compound 70 (500 mg, 1.59 mmol) in $CH_2Cl_2$ (3 mL) under inert atmosphere was added 4 N HCl in 1,4-dioxane (5 mL) at 0° C. and stirred for 6 h. The reaction was monitored by TLC; after completion of the reaction, the volatiles were removed in vacuo. The residue was neutralized with saturated $NaHCO_3$ solution (30 mL) and extracted with EtOAc (2×30 mL). The combined organic extracts were dried over sodium sulfate, filtered and concentrated in vacuo to obtain compound 71 (270 mg, 79%) as white solid. TLC: 30% EtOAc/hexanes ($R_f$ 0.2); $^1$H-NMR (DMSO-$d_6$, 400 MHz): δ 6.58 (s 1H), 3.62 (t, J=5.2 Hz, 4H), 2.70 (t, J=5.2 Hz, 4H), 2.27 (s, 3H).

Synthesis of 4-((4-(4-chloro-6-methylpyrimidin-2-yl)piperazin-1-yl)sulfonyl)phenol (72): To a stirred solution of compound 71 (250 mg, 1.17 mmol) in $CH_2Cl_2$ (10 mL) under argon atmosphere were added pyridine (0.47 mL, 5.86 mmol), 4-hydroxybenzenesulfonyl chloride 47 (452 mg, 2.34 mmol) at 0° C.; the mixture was warmed to RT and stirred for 16 h. The reaction was monitored by TLC; after completion of the reaction, the reaction mixture was diluted with water (30 mL) and extracted with $CH_2Cl_2$ (2×70 mL). The combined organic extracts were dried over sodium sulfate, filtered and concentrated in vacuo to obtain the crude product. The crude product was purified through silica gel column chromatography using 20% EtOAc/hexanes to afford compound 72 (160 mg, 37%) as an off-white solid. TLC: 40% EtOAc/hexanes ($R_f$, 0.8); $^1$H-NMR (DMSO-$d_6$, 400 MHz): δ 10.53 (s, 1H), 7.55 (d, J=6.8 Hz, 2H), 6.93 (d, J=6.8 Hz, 2H), 6.65 (s, 1H), 3.79 (t, J=4.8 Hz, 4H), 2.88 (t, J=4.8 Hz, 4H), 2.24 (s, 3H).

Synthesis of 2-(4-((4-(tert-butoxy) phenyl) sulfonyl) piperazin-1-yl)-4-chloro-6-methylpyrimidine (73): To a stirred solution of compound 72 (150 mg, 0.40 mmol) in $CH_2Cl_2$ (10 mL) under argon atmosphere were added magnesium perchlorate (36 mg, 0.16 mmol), Boc-anhydride (0.35 mg, 1.62 mmol) at 0° C.; the mixture was warmed to 45° C. and stirred for 48 h. The reaction was monitored by TLC; after completion of the reaction, the reaction mixture was diluted with water (20 mL) and extracted with $CH_2Cl_2$ (2×30 mL); the combined organic extracts were dried over sodium sulfate, filtered and concentrated in ractio to obtain the crude product. The crude product was purified through silica gel column chromatography using 20% EtOAc/hexanes to afford compound 73 (40 mg, 23%) as an off-white solid. TLC: 30% EtOAc/hexanes ($R_f$, 0.6); $^1$H-NMR (DMSO $d_6$, 400 MHz): δ 7.63 (d, J=8.8 Hz, 2H), 7.17 (d, J=8.8 Hz, 2H), 6.65 (s, 1H), 3.80 (t, J=5.2 Hz, 4H), 2.93 (t, J=5.2 Hz, 4H), 2.24 (s, 3H), 1.37 (s, 9H).

Synthesis of 2-(4-((4-(tert-butoxy)phenyl)sulfonyl)piperazin-1-yl)-6-methyl-N-(p-tolyl)pyrimidin-4-amine (target compound 27): To a stirred solution of compound 73 (40 mg, 0.09 mmol) in 1,4-dioxane (4 mL) under inert atmosphere were added p-toluidine 2 (13 mg, 0.12 mmol), cesium carbonate (46 mg, 0.14 mmol) at RT, purged under argon for 15 min. To this were added $Pd_2(dba)_3$ (4.5 mg, 0.004 mmol), Xantphos (3.8 mg, 0.006 mmol) in a sealed tube; heated to 120° C. and stirred for 16 h. The reaction was monitored by TLC; after completion of the reaction, the volatiles were removed in vacuo to obtain the crude product. The crude product was purified through silica gel column chromatography using 25% EtOAc/hexanes to afford 27 (15 mg, 32%) as an off-white solid. TLC: 30% EtOAc/hexanes ($R_f$, 0.5); $^1$H-NMR (DMSO-$d_6$, 400 MHz): δ 9.00 (s, 1H), 7.64 (d, J=8.8 Hz, 2H), 7.40 (d, J=8.4 Hz, 2H), 7.17 (d, J=8.8 Hz, 2H), 7.08 (d, J=8.4 Hz, 2H), 5.86 (s, 1H), 3.77 (t, J=5.2 Hz, 4H), 2.90 (t, J=5.2 Hz, 4H), 2.24 (s, 3H), 2.09 (s, 3H), 1.36 (s, 9H); LC-MS: 96.84%; 496.4 ($M^+$+1); (column: X-select CSH C-18, (50×3.0 mm, 3.5 μm); RT 3.89 min. 0.05% TFA (Aq): ACN; 0.8 mL/min); UPLC (purity): 96.72%; (column: Acquity UPLC BEH C-18 (2.1×50 mm, 1.7μ); RT 2.37 min. ACN: 0.025% TFA (Aq); 0.5 mL/min) (IP13110106).

Example 6

Synthesis of Target Compound 28

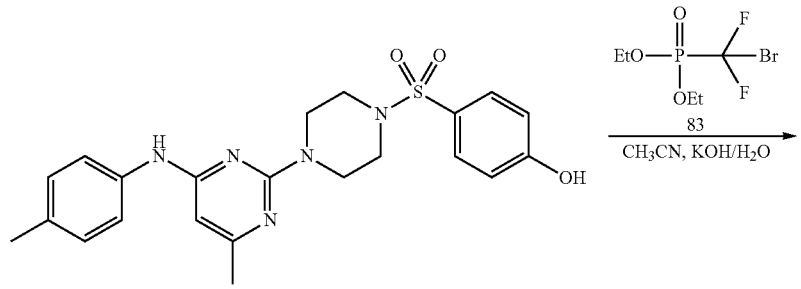

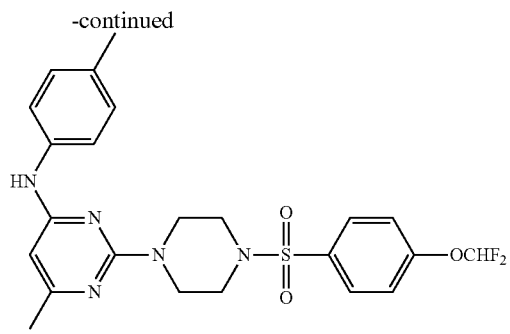

Synthesis of 4-((4-(4-methyl-6-(p-tolylamino)pyrimidin-2-yl)piperazin-1-yl)sulfony)phenol (28): To a stirred solution of target compound 4 (50 mg, 0.11 mmol) in CH$_3$CH (5 mL) were added potassium hydroxide (352 mg, 6.26 mmol) in H$_2$O (5 mL), diethyl (bromodifluoromethyl) phosphonate 83 (0.1 mL, 0.56 mmol) at 0° C.; warmed to 10° C. and stirred for 2 h. The reaction was monitored by TLC; after completion the reaction, the reaction mixture was diluted with water (20 mL) and extracted with EtOAc (2×30 mL). The combined organic extracts were washed with water (50 mL) dried over sodium sulfate, filtered and concentrated in vacuo to obtain the crude product. The crude product was purified through silica gel column chromatography using 20% EtOAc/hexanes to afford 28 (20 mg, 36%) as an off-white solid. TLC: 40% EtOAc/hexanes (R$_f$ 0.8); $^1$H-NMR (DMSO-d$_6$, 400 MHz): δ 9.00 (s, 1H), 7.81 (d, J=8.8 Hz, 2H), 7.56-7.20 (m, 5H), 7.08 (d, J=8.4 Hz, 2H), 5.86 (s, 1H), 3.78 (t, J=4.8 Hz, 4H), 2.93 (t, J=4.8 Hz, 4H), 2.24 (s, 3H), 2.08 (s, 3H); LC-MS: 97.11%; 490.4 (M$^+$+1); (column: X-select CSH C-18, (50×3.0 mm, 3.5 μm); RT 3.67 min. 0.05% TFA (Aq): ACN; 0.8 mL/min); UPLC (purity): 98.09%; (column: Acquity BEH C-18 (50×2.1 mm, 1.7μ); RT 2.18 min. ACN: 0.025% TFA (Aq); 0.5 mL/min) (IP13090051).

Example 7

Synthesis of Target Compound 29

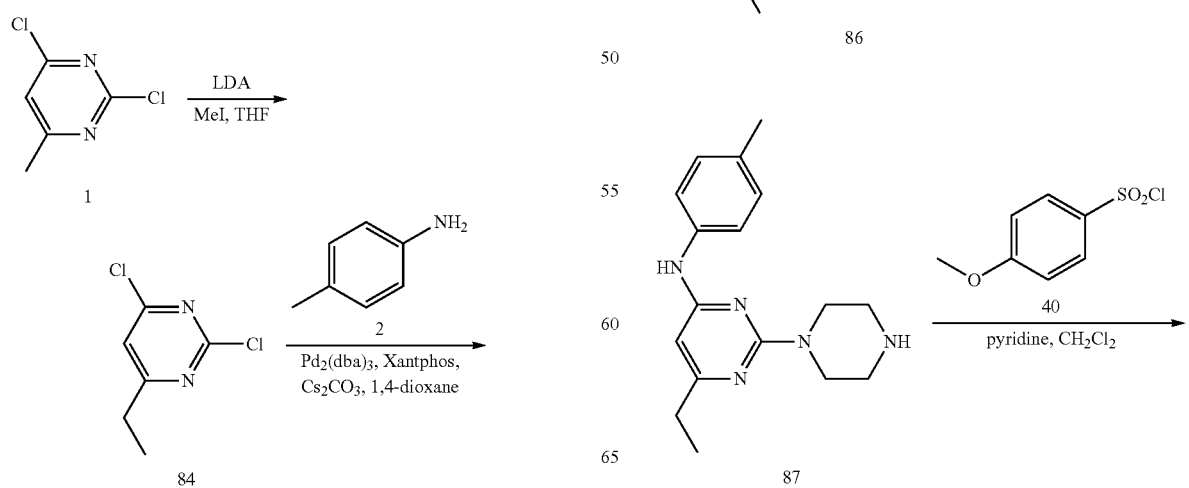

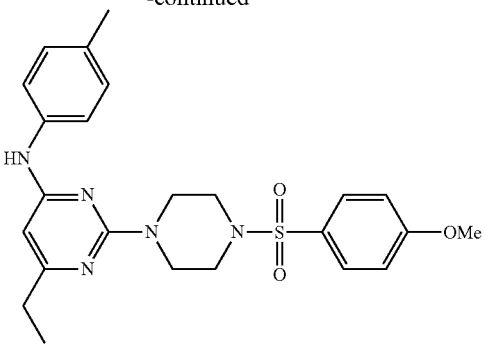

29

Synthesis of 2,4-dichloro-6-ethylpyrimidine (84): To a stirred solution of 2,4-dichloro-6-methylpyrimidine 1 (600 mg, 3.68 mmol) in THF (10 mL) under argon atmosphere was added lithium diisopropylamide (LDA; 2 M sol in THF, 2.2 mL, 4.40 mmol) at −78° C. and the stirred for 30 min. To this was added methyl iodide (0.27 mL, 4.40 mmol) at −78° C. and the reaction stirred for 3 h. The reaction was monitored by TLC; after completion of the reaction, the reaction mixture was quenched with saturated ammonium chloride solution (20 mL) and extracted with EtOAc (2×30 mL). The combined organic extracts were dried over sodium sulfate, filtered and concentrated in menu to obtain the crude product. The crude product was purified through silica gel column chromatography using 5% EtOAc/hexanes to afford compound 84 (120 mg, 19%) as a low melting pale yellow solid. TLC: 10% EtOAc/hexanes ($R_f$ 0.8); $^1$H-NMR (CDCl$_3$, 400 MHz): δ 7.17 (s, 1H), 2.80 (q, 2H), 1.32 (t, J=7.6 Hz, 3H).

Synthesis of 2-chloro-6-ethyl-N-(p-tolyl)pyrimidin-4-amine (85): To a stired solution of compound 84 (100 mg, 0.56 mmol) in 1,4-dioxane (5 mL) under argon atmosphere was added p-toluidine 2 (47.4 mg, 0.43 mmol) at RT and the mixture degassed under argon for 10 min. To this were added Pr$_2$(dba)$_3$ (20.6 mg, 0.02 mmol), Xantphos (19.5 mg, 0.03 mmol) and cesium carbonate (202 mg, 0.62 mmol) at RT; the reaction was heated to 110° C. and stirred for 2 h. The reaction was monitored by TLC; after completion of the reaction, the reaction mixture was diluted with water (20 mL) and extracted with EtOAc (2×30 mL). The combined organic extracts were dried over sodium sulfate, filtered and concentrated in racuo to obtain the crude product. The crude product was purified through silica gel column chromatography using 10% EtOAc/hexanes to aftbrd compound 85 (30 mg, 21%) as a sticky solid. TLC: 15% EtOAc/hexanes ($R_f$ 0.3); $^1$H-NMR (CDCl$_3$, 400 MHz): δ 7.21 (d, J=8.4 Hz, 2H), 7.15 (d, J=8.4 Hz, 2H), 6.82 (br s, 1H), 6.38 (s, 1H), 2.58 (q, 2H), 2.37 (s, 3H), 1.21 (t, J=7.6 Hz, 3H).

Synthesis of tert-butyl 4-(4-ethyl-6-(p-tolylamino)pyrimidm-2-yl)piperazine-1-carboxylate (86): To a stirred solution of compound 85 (30 mg, 0.12 mmol) in n-butanol (2 mL) under argon atmosphere were added tert-butyl piperazine-1-carboxylate 4 (33.7 mg, 0.18 mmol) and N,N-diisopropylethylamine (0.04 mL, 0.24 mmol) in sealed tube at RT; the mixture was heated to 80° C. and stirred for 5 h. The reaction was monitored by TLC; after completion of the reaction, the volatiles were removed in vacuo to obtain the crude product. The crude product was purified through silica gel column chromatography using 15% EtOAc/hexanes to afford compound 86 (65 mg, 68%) as a low melting colorless solid. TLC: 20% EtOAc/hexanes ($R_f$ 0.6); $^1$H-NMR (DMSO-d$_6$, 400 MHz): δ 9.02 (s, 1H), 7.46 (d, j=8.4 Hz, 2H), 7.10 (d, J=8.4 Hz, 2H), 5.90 (s, 1H), 3.67 (t, J=4.8 Hz, 4H), 3.37 (t, J=5.2 Hz, 4H), 2.40 (q, 2H), 2.27 (s, 3H), 1.46 (s, 9H), 1.14 (t, J=7.6 Hz, 3H).

Synthesis of 6-ethyl-2-(Piperazin-1-yl)-N-(p-tolyppyrimidin-4-amine (87): To a stirred solution of compound 86 (65 mg, 0.16 mmol) in CH$_2$Cl$_2$ (2 mL) under argon atmosphere was added 4 N HCl in 1,4-dioxane (0.25 mL, 0.82 mmol) at 0° C.; warmed to RT and stirred for 2 h. The reaction was monitored by TLC; after completion of the reaction, the reaction mixture was diluted with water (15 mL) and extracted with CH$_2$Cl$_2$ (2×20 mL). The aqueous layer was basified with 5% aqueous NaHCO$_3$ solution (10 mL) and extracted with CH$_2$Cl$_2$ (2×30 mL). The combined organic extracts were dried over sodium sulfate, filtered, and concentrated in vacuo to obtain crude compound 87 (35 mg, 72%) as an off-white solid. TLC: 10% CH$_3$OH/CH$_2$Cl$_2$ ($R_f$ 0.3); $^1$H-NMR (DMSO-d$_6$, 500 MHz): δ 8.98 (s, 1H), 7.47 (d, J=8.0 Hz, 2H), 7.09 (d, J=8.5 Hz, 2H), 5.86 (s, 1H), 3.63-3.62 (m, 4H), 2.74-2.73 (m, 4H), 2.41-2.37 (m, 3H), 2.24 (s, 3H), 1.13 (t, J=8.0 Hz, 3H).

Synthesis of 6-ethyl-2-(4-((4-methoxyphenyl)sulfonyl)piperazin-1-yl)-N-(p-tolyl)pyrimidin-4-amine (29): To a stirred solution of compound 87 (35 mg, 0.11 mmol) in CH$_2$Cl$_2$ (2 mL) under argon atmosphere were added pyridine (0.047 mL, 0.58 mmol) and 4-methoxybenzenesulfonyl chloride 40 (26.7 mg, 0.12 mmol) at 0° C.; the mixture was warmed to RT and stirred for 16 h. The reaction was monitored by TLC; after completion of the reaction, the reaction mixture was diluted with CH$_2$Cl$_2$ (20 mL) and washed with 2 N HCl (2×10 mL). The organic layer was dried over sodium sulfate, filtered and concentrated in vacuo to obtain the crude product, which was precipitated with 20% EtOAc/hexanes to afford 29 (25 mg, 45%) as an off-white solid. TLC: 5% CH$_3$OH/CH$_2$Cl$_2$ ($R_f$ 0.7); $^1$H-NMR (DMSO-d$_6$, 400 MHz): δ 9.02 (s, 1H), 7.67 (d, J=8.8 Hz, 2H), 7.40 (d, J=8.4 Hz, 2H), 7.13 (d, J=8.8 Hz, 2H), 7.08 (d, J=8.4 Hz, 2H), 5.87 (s, 1H), 3.82 (s, 3H), 3.78 (t, J=4.8 Hz, 4H), 2.88 (t, J=4.8 Hz, 4H), 2.36 (q, 2.24 (s, 3H), 1.09 (t, J=7.6 Hz, 3H), LC-MS: 95.60%; 468.6 (M$^+$+1); (column: X-select CSH C-18 (50×3.0 mm, 3.5 μm); RT 3.70 min. 0.05% TFA (Aq): ACN; 0.8 mL/min); UPLC (purity): 98.98%; (column: Acquity BEH C-18 (50×2.1 mm, 1.7μ); RT 2.13 min. ACN: 0.025% TFA (Aq); 0.5 mL/min) (IP13070762).

Example 8

Synthesis of Target Compound 30

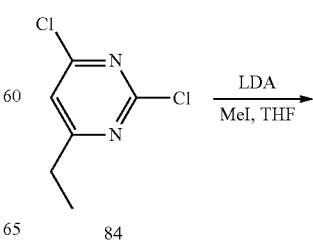

84

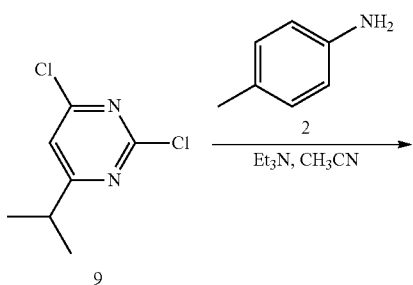
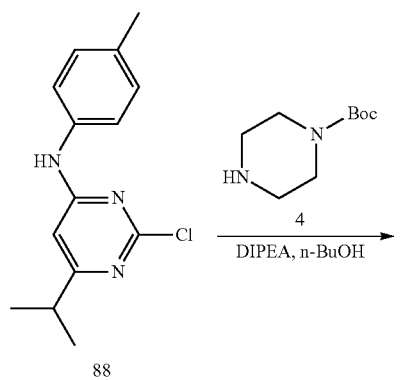
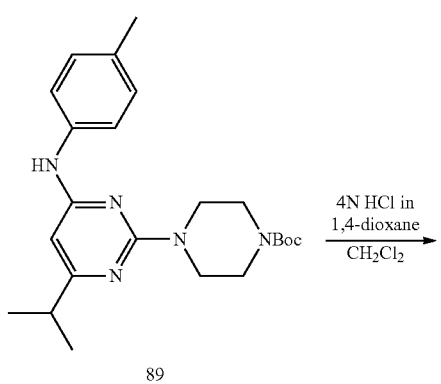
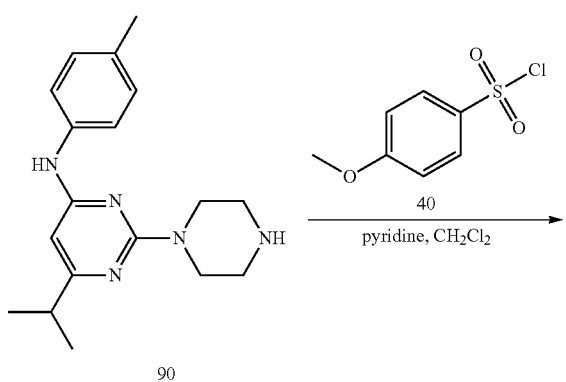
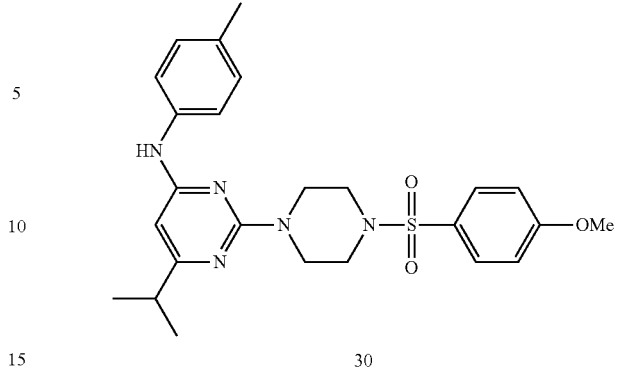

Synthesis of 2,4-dichloro-6-isopropylpyrimidine (9): To a stirred solution of 2,4-dichloro-6-ethylpyrimidine 84 (950 mg, 5.36 mmol) in THF (50 mL) under argon atmosphere was added LDA (2 M sol. in THF, 5.37 mL, 10.73 mmol) at −70° C. and stirred for 30 min. To this was added methyl iodide (0.66 mL, 10.73 mmol) at −70° C. and stirred for 2 h. The reaction was monitored by TLC; after completion of the reaction, the reaction mixture was quenched with aqueous saturated ammonium chloride solution (20 mL) and extracted with EtOAc (2×50 mL). The combined organic extracts were dried over sodium sulfite, filtered and concentrated in vacuo to obtain the crude product. The crude product was purified through silica gel column chromatography using 2% EtOAc/hexanes to afford compound 9 (500 mg, 50%) as a white solid, TLC: 10% EtOAc/hexanes ($R_f$ 0.5); $^1$H-NMR (CDCl$_3$, 400 MHz): δ 7.16 (s, 1H), 3.04-2.97 (m, 1H), 1.31 (d, J=6.8 Hz, 6H).

Note: Compound 9 may also be prepared from trichhropyrimidine and isopropyl magnesium chloride as described above.

Synthesis of 2-chloro-6-isopropyl-N-(p-tolyl)pyrimidin-4-amine (88): To a stirred solution of compound 9 (500 mg, 2.61 mmol) in acetonitrile (8 mL) under argon atmosphere were added p-toluidine 2 (285 mg, 2.61 mmol) and triethylamine (0.73 mL, 5.23 mmol) in sealed tube at RT; the mixture was heated to 60° C. and stirred for 24 h. The reaction was monitored by TLC; after completion of the reaction, the volatiles were removed in vacuo, the residue was diluted with water (30 mL), and then extracted with EtOAc (2×40 mL). The combined organic extracts were dried over sodium sulfate, filtered and concentrated in vacuo to obtain the crude product. The crude product was purified through silica gel column chromatography using 7% EtOAc/hexanes to afford compound 88 (130 mg, 19%) as white solid. TLC: 20% EtOAc/hexanes ($R_f$ 0.3); $^1$H-NMR (DMSO$_4$$_6$, 500 MHz): δ 9.80 (s, 1H), 7.42 (d, J=7.5 Hz, 2H), 7.16 (d, J=8.0 Hz, 2H), 6.53 (s, 1H), 2.78-2.76 (m, 1H), 2.27 (s, 3H), 1.16 (d, J=7.0 Hz, 6H).

Synthesis of tert-butyl 4-(4-isopropyl-6-(p-tolylamino)pyrimidin-2-yl)piperazine-1-carboxylate (89): To a stirred solution of compound 88 (160 mg, 0.61 mmol) in n-butanol (5 mL) under argon atmosphere wore added tert-butyl piperazine-1-carboxylate 4 (342 mg, 1.83 mmol) and N,N-diisopropylethylamine (0.21 mL, 1.22 mmol) in sealed tube at RT; the mixture was heated to 100° C. and stirred for 24 h. The reaction was monitored by TLC; after the reaction was complete, the volatiles were removed in vacuo, the residue was diluted with water (20 mL), and extracted with EtOAc (2×30 mL). The combined organic extracts were dried over sodium sulfate, filtered and concentrated in vacuo to obtain the crude product. The crude product was purified through silica gel column chromatography using 30% EtOAc/hexanes to afford compound 89 (155 mg, 61%) as white solid. TLC: 15% EtOAc/hexanes (R$_f$ 0.3); $^1$H-NMR (DMSO-d$_6$, 500 MHz): δ 9.05 (s, 1H), 7.47 (d, J=8.5 Hz, 2H), 7.10 (d, J=8.0 Hz, 2H), 5.91 (s, 1H), 3.68-3.66 (m, 4H), 3.43-3.37 (m, 4H), 2.63-2.60 (m, 1H), 2.24 (s, 3H), 1.42 (s, 9H), 1.14 (d, J=7.5 Hz, 6H).

Synthesis of 6-isopropyl-(piperazin-1-yl)-N-(p-tolyl)pyrimidin-4-amine (90): To a stirred solution of compound 89 (155 mg, 0.37 mmol) in CH$_3$Cl$_2$ (5 mL) under argon atmosphere was added 4 N HCl in 1,4-dioxane (0.47 mL, 1.87 mmol) at 0° C.; the mixture was warmed to RT and stirred for 4 h. The reaction was monitored by TLC; after the reaction was complete, the reaction mixture was diluted with water (15 mL), the pH was adjusted to ~8 with aqueous saturated NaHCO$_3$ solution (20 mL), and extracted with EtOAc (2×30 mL). The combined organic extracts were dried over sodium sulfate, filtered and concentrated in vacuo to obtain the crude compound 90 (100 mg, 85%) as white solid. TLC: 50% EtOAc/hexanes (R$_f$ 0.2); $^1$H-NMR (DMSO-d$_6$, 500 MHz): δ 8.99 (s, 1H), 7.48 (d, J=8.0 Hz, 2H), 7.08 (d, J=8.0 Hz, 2H), 5.86 (s, 1H), 3.61-3.59 (m, 4H), 2.71-2.70 (m, 4H), 2.64-2.58 (m, 1H), 2.23 (s, 3H), 1.13 (d, J=7.5 Hz, 6H).

Synthesis of 6-isopropyl-2-(4-((4-methoxyphenyl) sulfonyl) piperazin-1-yl)-N-(p-tolyl)pyrimidin-4-amine (30): To a stirred solution of compound 90 (100 mg, 0.32 mmol) in CH$_2$Cl$_2$ (5 mL) under argon atmosphere were added 4-methoxybenzenesulfonyl chloride 40 (73 mg, 0.35 mmol) and pyridine (0.13 mL, 1.6 mmol) at 0° C.; the mixture was warmed to RT and stirred for 16 h. The reaction was monitored by TLC; after completion of the reaction, the reaction mixture was diluted with CH$_2$Cl$_2$ (30 mL), washed with 1N HCl (10 mL) and aqueous saturated NaHCO$_3$ solution (10 mL). The organic layer was separated, dried over sodium sulfate, filtered and concentrated in vacuo to obtain the crude product, which was triturated with 2% CH$_2$Cl$_2$/n-pentane to afford 30 (50 mg, 32%) as a white solid. TLC: 5% CH$_3$OH/CH$_2$Cl$_2$ (R$_f$ 0.8); $^1$H-NMR (DMSO-d$_6$, 400 MHz): δ 9.03 (s, 1H), 7.68 (d, J=8.8 Hz, 2H), 7.41 (d, J=8.0 Hz, 2H), 7.13 (d, J=8.8 Hz, 2H), 7.08 (d, J=8.4 Hz, 2H), 5.87 (s, 1H), 3.82 (s, 3H), 3.78 (t, J=4.4 Hz, 4H), 2.89 (t, J=4.8 Hz, 4H), 2.56-2.52 (m, 1H), 2.24 (s, 3H), 1.10 (d, J=6.8 Hz, 6H); LC-MS: 97.21%; 482.4 (M$^+$+1); (column: X-select CSH C-18 (50×3.0 mm, 3.5 µm); RT 3.70 min. 0.05% TFA (Aq): ACN; 0.8 mL/min); UPLC (purity): 98.80%; (column: Acquity BEH C-18 (50×2.1 mm, 1.7µ); RT 2.19 min. ACN: 0.025% TFA (Aq); 0.5 mL/min) (IP13080332).

Example 9

Synthesis of Target Compound 31

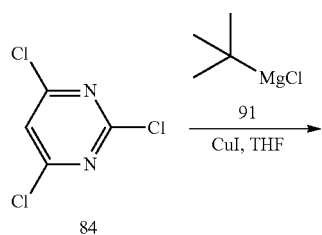

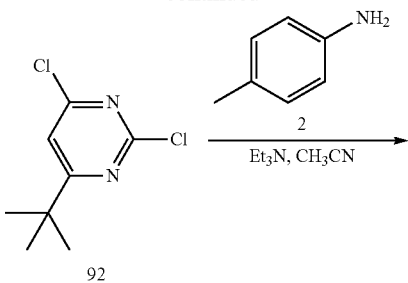

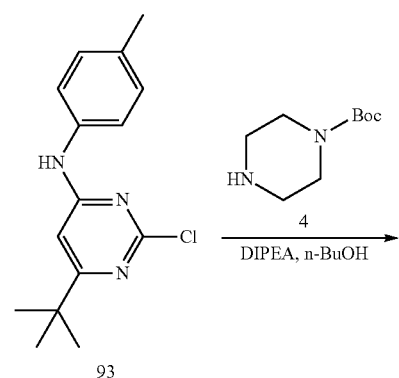

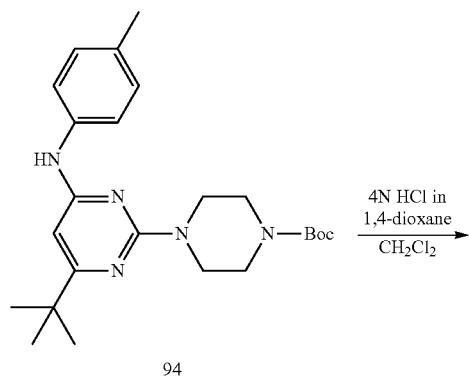

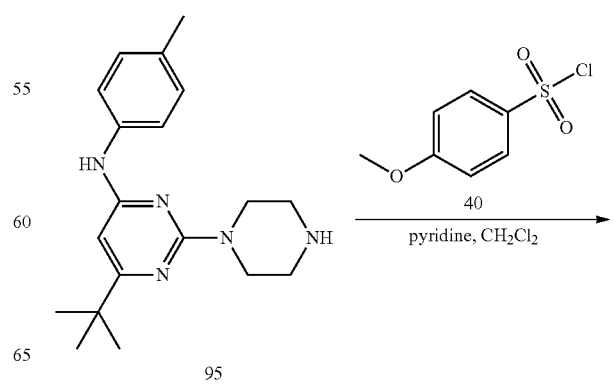

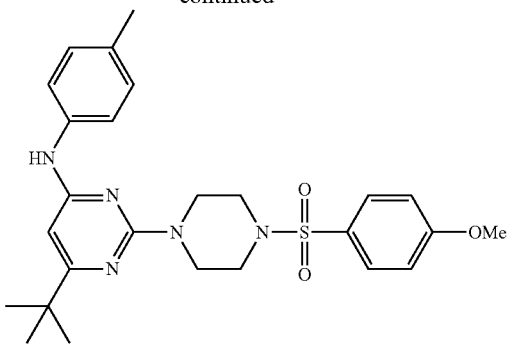

31

Synthesis of 4-(tert-butyl)-2,6-dichloropyrimidine (92): To a stirred solution of 2,4,6-trichlorpyrimidine 7 (1.5 g, 8.19 mmol) in THF (50 mL) under argon atmosphere were added tert-butyl magnesium chloride 91 (2 M sol. in diethyl ether, 6.12 mL, 12.29 mmol) and copper iodide (78 mg, 0.41 mmol) at −10° C.; the mixture was stirred at 0° C. for 1 hour. The reaction was monitored by TLC; after completion of the reaction, the reaction mixture was quenched with aqueous saturated ammonium chloride solution (50 mL) and extracted with EtOAc (2×60 mL). The combined organic extracts were dried over sodium sulfate, filtered and concentrated in vacuo to obtain the crude product. The crude product was purified through silica gel column chromatography using 2% EtOAc/hexanes to afford compound 92 (900 mg, 56%) as colorless semi solid. TLC: 10% EtOAc/hexanes ($R_f$ 0.5); $^1$H-NMR (CDCl$_3$, 500 MHz): δ 7.40 (s, 1H), 1.32 (s, 9H).

Synthesis of 6-(tert-butyl)-2-chloro-N-(p-tolyl)pyrimidin-4-amine (93): To a stirred solution of compound 92 (500 mg, 2.43 mmol) in acetonitrile (8 mL) under argon atmosphere were added p-toluidine 2 (265 mg, 2.43 mmol) and triethylamine (0.68 mL, 4.87 mmol) in a sealed tube at RT; the mixture was heated to 60° C. and stirred for 24 h. The reaction was monitored by TLC; after completion of the reaction, the volatiles were removed in vacuo, the residue was diluted with water (20 mL), and extracted with EtOAc (2×40 mL). The combined organic extracts were dried over sodium sulfate, filtered and concentrated in vacuo to obtain the crude product. The crude product was purified through silica gel column chromatography using 7% EtOAc/hexanes to afford compound 93 (70 mg, 10%) as a white solid. TLC: 20% EtOAc/hexanes ($R_f$ 0.2); $^1$H-NMR (DMSO-d$_6$, 400 MHz): δ 9.80 (s, 1H), 7.44 (d, J=8.0 Hz, 2H), 7.16 (d, J=8.0 Hz, 2H), 6.64 (s, 1H), 2.27 (s, 3H), 1.22 (s, 9H).

Synthesis of tert-butyl 4-(4-(tert-butyl)-6-(p-tolylamino)pyrimidin-2-yl) piperazine-1-carboxylate (94): To a stirred solution of compound 93 (70 mg, 0.25 mmol) in n-butanol (5 mL) under argon atmosphere were added tert-butyl piperazine-1-carboxylate 4 (142 mg, 0.76 mmol) and N,N-diisopropylethylamine (0.08 mL, 0.51 mmol) in a sealed tube at RT; the mixture was heated to 100° C. and stirred for 24 h. The reaction was monitored by TLC; after completion of the reaction, the volatiles were removed in vano the residue was diluted with water (20 mL) and extracted with EtOAc (2×30 mL). The combined organic extracts were dried over sodium sulfate, filtered and concentrated in vacuo to obtain the crude product. The crude product was purified through silica gel column chromatography using 30% EtOAc/hexanes to afford compound 94 (75 mg, 69%) as a white solid. TLC: 15% EtOAc/hexanes ($R_f$ 0.3); $^1$H-NMR (DMSO-d$_6$, 500 MHz): δ 9.07 (s, 1H), 7.49 (d, J=8.0 Hz, 2H), 7.10 (d, J=8.5 Hz, 2H), 6.03 (s, 1H), 3.68-3.66 (m, 4H), 3.40-3.35 (m, 4H), 2.24 (s, 3H), 1.42 (s, 9H), 1.20 (s, 9H).

Synthesis of 6-(tert-butyl)-2-(piperazin-1-yl)-N-(p-tolyl) pyrimidin-4-amine (95): To a stirred solution of compound 94 (75 mg, 0.18 mmol) in CH$_2$Cl$_2$ (5 mL) under argon atmosphere was added 4 N HCl in 1,4-dioxane (0.28 mL, 0.88 mmol) at 0° C.; the mixture was warmed to RT and stirred for 4 h. The reaction was monitored by TLC; after completion of the reaction, the reaction mixture was diluted with water (15 mL), the pH was adjusted to ~8 with aqueous saturated NaHCO$_3$ solution (10 mL), and extracted with EtOAc (2×30 mL). The combined organic extracts were dried over sodium sulfate, filtered and concentrated in vacuo to obtain the crude compound 95 (50 mg, 87%) as white solid. TLC: 50% EtOAc/hexanes ($R_f$ 0.2); $^1$H-NMR (DMSO-d$_6$, 400 MHz): δ 8.99 (s, 1H), 7.48 (d, J=8.8 Hz, 2H), 7.07 (d, J=8.0 Hz, 2H), 5.98 (s, 1H), 3.61 (t, J=4.8 Hz, 4H), 2.72 (t, J=4.8 Hz, 4H), 2.23 (s, 3H), 1.19 (s, 9H).

Synthesis of 6-(tert-butyl)-2-(4-((4-methoxyphenyl) sulfonyl) piperazin-1-yl)-N-(p-tolyl)pyrimidin-4-amine (31): To a stirred solution of compound 95 (50 mg, 0.15 mmol) in CH$_2$Cl$_2$ (5 mL) under argon atmosphere were added 4-methoxybenzenesulfonyl chloride 40 (35 mg, 0.17 mmol) and pyridine (0.06 mL, 0.76 mmol) at 0° C.; the mixture was warmed to RT and stirred for 16 h. The reaction was monitored by TLC; after completion of the reaction, the reaction mixture was diluted with CH$_2$Cl$_2$ (30 mL) and washed with 1 N HCl (10 mL), followed by aqueous saturated NaHCO$_3$ solution (10 mL). The organic layer was dried over sodium sulfate, filtered and concentrated in vacuo to obtain the crude product, which was triturated with 2% CH$_2$Cl$_2$/n-pentane to afford 31 (30 mg, 40%) as a white solid, TLC: 5% CH$_3$OH/CH$_2$Cl$_2$ ($R_f$ 0.9); $^1$H-NMR (DMSO-d$_6$, 400 MHz): δ 9.05 (br s, 1H), 7.68 (d, J=9.2 Hz, 2H), 7.42 (d, J=8.4 Hz, 2H), 7.13 (d, J=9.2 Hz, 2H), 7.08 (d, J=8.4 Hz, 2H), 6.00 (s, 1H), 3.82 (s, 3H), 3.80 (t, J=4.4 Hz, 4H), 2.90 (t, J=4.8 Hz, 4H), 2.24 (s, 3H), 1.16 (s, 9H); LC-MS: 97.25%; 496.4 (M$^+$+1); (column: X-select CSH C-18 (50×3.0 mm, 3.5 μm); RT 3.95 min. 0.05% TFA (Aq): ACN; 0.8 mL/min); HPLC (purity): 99.15%; (column: Eclipse-XDR-C-18 (150×4.6 mm, 5 μm); RT 13.55 min. ACN: 5 mM NH$_4$OAc (Aq); 1.0 mL/min) (IP13080340).

Example 10

Synthesis of Target Compound 32

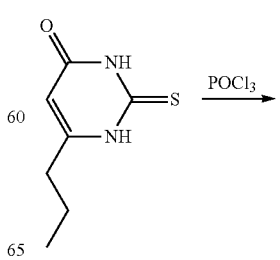

96

-continued

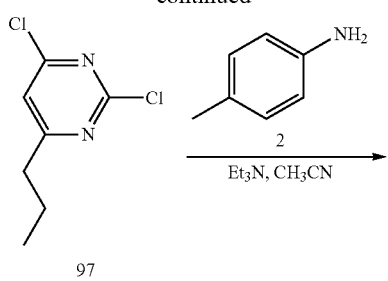

97

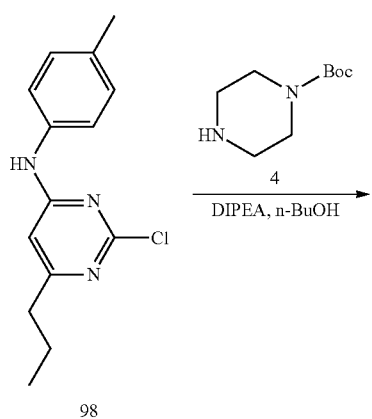

98

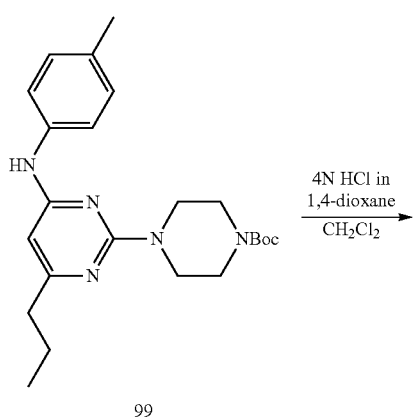

99

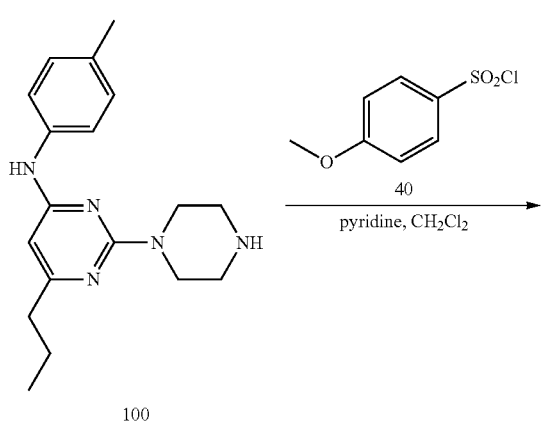

100

-continued

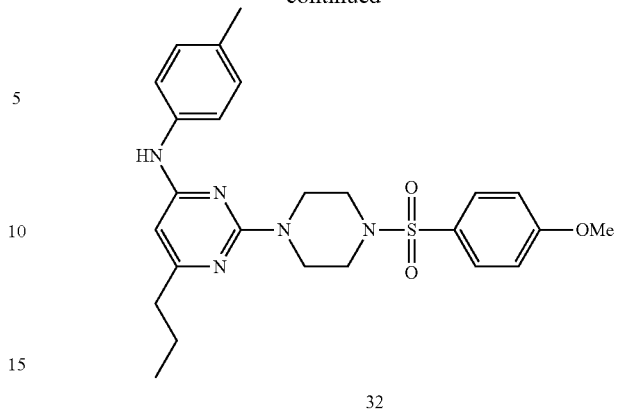

32

Synthesis of 2,4-dichloro-6-propylpyrimidine (97): A stirred solution of 6-propyl-2-thioxo-2,3-dihydropyrimidin-4(1H)-one 96 (1 g, 5.81 mmol) in phosphoryl trichloride (5 mL) under argon atmosphere was heated to 110° C. and stirred for 16 h. The reaction was monitored by TLC; after completion of the reaction, the reaction mixture was diluted with ice water (20 mL), neutralized with aqueous saturated NaHCO$_3$ solution (20 mL) and extracted with CH$_2$Cl$_2$ (2×30 mL). The combined organic extracts were dried over sodium sulfate, filtered and concentrated in vacuo to obtain the crude product. The crude product was purified through silica gel column chromatography using 2% EtOAc/hexanes to afford compound 97 (300 mg, 27%) as a colorless liquid. TLC: 10% EtOAc/hexanes (R$_f$ 0.8); $^1$H-NMR (CDCl$_3$, 400 MHz): δ 7.15 (s, 1H), 2.72 (t, J=7.6 Hz, 2H), 1.81-1.72 (m, 2H), 0.99 (t, J=7.6 Hz, 3H).

Synthesis of 2-chloro-6-propyl-N-(p-tolyl) pyrimidin-4-amine (98): To a stirred solution of compound 97 (300 mg, 1.57 mmol) in CH$_3$CN (5 mL) under argon atmosphere were added p-toluidine 2 (205 mg, 1.88 mmol) and triethylamine (0.45 mL, 3.14 mmol) at RT; the mixture was heated to 70° C. and stirred for 36 h. The reaction was monitored by TLC; after completion of the reaction, the volatiles were removed in vacuo to obtain the crude product. The crude product was purified through silica gel colimn chromatography using 4% EtOAc/hexanes to afford compound 98 (120 mg, 30%) as a sticky syrup. TLC: 10% EtOAc/hexanes (R$_f$ 0.4); $^1$H NMR (DMSO-d$_6$, 400 MHz): δ 9.77 (s, 1H), 7.41 (d, J=8.4 Hz, 2H), 7.16 (d, 8.4 Hz, 2H), 6.51 (s, 1H), 2.50-2.47 (m, 2H), 2.27 (s, 3H), 1.64-1.59 (m, 2H), 0.89 (t, J=7.6 Hz, 3H).

Synthesis of tert-butyl 4-(4-propyl-6-(p-tolylamino)pyrimidin-2-yl)piperazine-1-carboxylate (99): To a stirred solution of compound 98 (100 mg, 0.38 mmol) in n-butanol (5 mL) under argon atmosphere were added tert-butyl piperazine-1-carboxylate 4 (107 mg, 0.57 mmol) and N,N-diisopropylethylamine (0.14 mL, 0.76 mmol) at RT; the mixture was heated to 100° C. and stirred for 20 h. The reaction was monitored by TLC; after completion of the reaction, the volatiles were removed in vacuo to obtain the crude product. The crude product was purified through silica gel column chromatography using 10% EtOAc/hexanes to afford compound 99 (100 mg, 64%) as a white solid. TLC: 10% EtOAc/hexanes (R$_f$ 0.8); $^1$H-NMR (DMSO-d$_6$, 400 MHz): δ 9.02 (s, 1H), 7.46 (d, J=8.4 Hz, 2H), 7.10 (d, J=8.0 Hz, 2H), 5.88 (s, 1H), 3.66 (t, J=5.2 Hz, 4H), 3.37 (t, J=5.2 Hz, 4H), 2.36 (t, J=7.6 Hz, 2H), 2.24 (s, 3H), 1.66-1.56 (m, 2H), 1.42 (s, 9H), 0.90 (t, J=7.6 Hz, 3H).

Synthesis of 2-(piperazin-1-yl)-6-propyl-N-(p-tolyl)pyrimidin-4-amine (100): To a stirred solution of compound 99

(100 mg, 0.24 mmol) in CH$_2$Cl$_2$ (2 mL) under argon atmosphere was added 4 N HCl in 1,4-dioxane (0.30 mL, 1.20 mmol) at 0° C.; the mixture was warmed to RT and stirred for 2 h. The reaction was monitored by TLC; after completion of the reaction, the reaction mixture was diluted with water (15 mL) and extracted with CH$_2$Cl$_2$ (2×20 mL). The aqueous layer was basified with 10% aqueous NaHCO$_3$ solution (10 mL) and extracted with CH$_2$Cl$_2$ (2×30 mL). The combined organic extracts were dried over sodium sulfate, filtered and concentrated in vacuo to obtain the crude product. The crude product was purified, through silica gel column chromatography using 5% EtOAc/hexanes to afford compound 100 (50 mg, 66%) as a white solid. TLC: 10% CH$_3$OH/CH$_2$Cl$_2$ (R$_f$ 0.3); $^1$H-NMR (DMSO-d$_6$, 500 MHz): δ 8.94 (s, 1H), 7.47 (d, J=8.0 Hz, 2H), 7.09 (d, J=8.5 Hz, 2H), 5.84 (s, 1H), 3.61-3.59 (m, 4H), 2.72-2.70 (m, 4H), 2.37-2.33 (m, 3H), 2.24 (s, 3H), 1.63-1.59 (m, 2H), 0.91 (t, J=7.0 Hz, 3H).

Synthesis of 2-(4-((4-methoxyphenyl) sulfonyl) piperazin-1-yl)-6-propyl-N-(p-tolyl)pyrimidin-4-amine (32): To a stirred solution of compound 100 (50 mg, 0.16 mmol) in CH$_2$Cl$_2$ (4 mL) under argon atmosphere were added pyridine (0.067 mL, 0.80 mmol) and 4-methoxybenzenesulfonyl chloride 40 (36.5 mg, 0.17 mmol) at 0° C.; the mixture was warmed to RT and stirred for 3 h. The reaction was monitored by TLC; after completion of the reaction, the reaction mixture was diluted with CH$_2$Cl$_2$ (15 mL) and washed with 1 N HCl (2×15 mL) and 10% aqueous NaHCO$_3$ (20 mL). The organic layer was dried over sodium sulfate, filtered and concentrated in vacuo to obtain the crude product, which was precipitated with 5% EtOAc/hexanes to afford 32 (30 mg, 39%) as a white solid. TLC: 5% CH$_3$OH/Ch$_2$Cl$_2$ (R$_f$ 0.7); $^1$H-NMR (DMSO-d$_6$, 400 MHz): δ 9.03 (br s, 1H), 7.67 (d, J=8.8 Hz, 2H), 7.40 (d, J=8.4 Hz, 2H), 7.14-7.08 (m, 4H), 5.86 (s, 1H), 3.82 (s, 3H), 3.78 (t, J=5.2 Hz, 4H), 2.89-2.87 (m, 4H), 2.32 (t, J=7.2 Hz, 2H), 2.24 (s, 3H), 1.61-1.52 (m, 2H), 0.86 (t, J=7.6 Hz, 3H); LC-MS: 98.96%; 482.6 (M$^+$+1); (column: X-select CRT C-18, (50×3.0 mm, 3.5 μm); RT 3.76 min. 0.05% TFA (Aq): ACN; 0.8 mL/min); UPLC (purity): 98.43%; (column: Acquity BEH C-18 (50× 2.1 mm, 1.7μ); RT 2.24 min. ACN: 0.025% TFA (Aq); 0.5 mL/min) (IP13080047).

Example 11

Synthesis of Target Compound 33

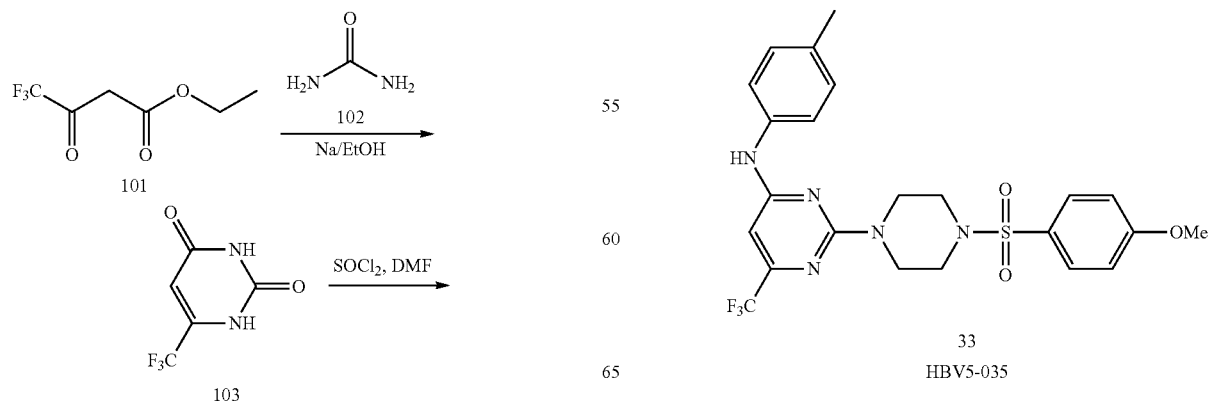

Synthesis of 6-(trifluoromethyl)pyrimidine-2,4(1H,3H)-dione (103): To a stirred solution of ethyl 4,4,4-trifluoro-3-oxobutanoate 101 (3 g, 16.30 mmol) in ethanol (30 mL) under argon atmosphere were added urea 102 (978 mg, 16.30 mmol) and freshly prepared sodium ethoxide (750 mg of Na in 30 mL of EtOH) at RT; the mixture was heated to 90° C. and stirred for 24 h. The reaction was monitored by TLC; after completion of the reaction, the volatiles were removed in vacuo, diluted with water (25 mL), acidified with 1 N HCl (10 mL) and extracted with EtOAc (2×40 mL). The combined organic extracts were dried over sodium sulfate, filtered and concentrated in vacuo to afford compound 103 (650 mg, 22%) as a white solid. TLC: 5% $CH_3OH/CH_2Cl_2$ ($R_f$, 0.3); $^1$H-NMR (DMSO-$d_6$, 500 MHz); δ 12.07 (s, 1H), 11.54 (s, 1H), 6.07 (s, 1H).

Synthesis of 2,4-dichloro-6-(trifluoromethyl)yyrimidine (104): To a stirred solution of compound 103 (150 mg, 0.83 mmol) in DMF (5 mL) under argon atmosphere was added sulfurous dichloride (0.75 mL) in sealed tube at 0° C.; the mixture was heated to 75° C. and stirred for 4 h. The reaction was monitored by TLC; after completion of the reaction, the reaction mixture was diluted with ice water (20 mL), neutralized with 10% aqueous $NaHCO_3$ solution (20 mL) and extracted with hexanes (2×30 mL). The combined organic extracts were dried over sodium sulfate, filtered and concentrated in vacuo at 35° C. to afford compound 104 (100 mg) as colorless liquid. TLC: 10% EtOAc/hexanes ($R_f$, 0.9); $^1$H-NMR (CDCl$_3$, 500 MHz): δ 7.65 (s, 1H).

Synthesis of 2-chloro-N-(p-tolyl)-6-(trifluormethyl)pyrimidin-4-amine (105): To a stirred solution of compound 104 (400 mg, 1.86 mmol) in $CH_3CN$ (6 mL) under argon atmosphere were added p-toluidine 2 (202 mg, 1.86 mmol) and triethylamine (0.40 mL, 2.79 mmol) in a sealed tube at RT; the mixture was heated to 70° C. and stirred for 24 h. The reaction was monitored by TLC; after completion of the reaction, the volatiles were removed in mew to obtain the crude product. The crude product was purified through silica gel column chromatography using 7% EtOAc/hexanes to afford compound 105 (120 mg, 22%) as a yellow solid. TLC: 15% EtOAc/hexanes ($R_f$, 0.5); $^1$H-NMR (DMSO-$d_6$, 400 MHz): δ 10.47 (br s, 1H), 7.50-7.48 (m, 2H), 7.22 (d, J=8.4 Hz, 2H), 7.06 (br s, 1H), 2.30 (s, 3H).

Synthesis of tert-butyl 4-(4-(p-tolylamino)-6-(trifluoromethyl) pyrimidin-2-yl)piperazine-1-carboxylate (106): To a stirred solution of compound 105 (120 mg, 0.41 mmol) in n-butanol (7 mL) under argon atmosphere were added tert-butyl piperazine-1-carboxylate 4 (116 mg, 0.62 mmol) and N,N-diisopropylethylamine (0.15 mL, 0.83 mmol) at RT; the mixture was heated to 100° C. and stirred for 24 h. The reaction was monitored by TLC; after completion of the reaction, the volatiles were removed in vacuo to obtain the crude product. The crude product was purified through silica gel column chromatography using 10% EtOAc/hexanes to atford compound 106 (140 mg, 77%) as a white solid. TLC: 5% EtOAc/Toluene ($R_f$, 0.8); $^1$H-NMR (DMSO-$d_6$, 400 MHz): δ 9.66 (s, 1H), 7.49 (d, J=8.0 Hz, 2H), 7.17 (d, J=8.0 Hz, 2H), 6.36 (s, 1H), 3.69 (t, J=5.6 Hz, 4H), 3.40 (t, J=6.0 Hz, 4H), 2.27 (s, 3H), 1.42 (s, 9H).

Synthesis of 2-(piperazin-1-yl)-N-(p-tolyl)-6-(trifluoromethyl)pyrimidin-4-amine (107): To a stirred solution of compound 106 (140 mg, 0.32 mmol) in $CH_2Cl_2$ (3 mL) under argon atmosphere was added 4 N HCl in 1,4-dioxane (0.40 mL, 1.60 mmol) at 0° C.; the mixture was warmed to RT and stirred for 2 h. The reaction was monitored by TLC; after completion of the reaction, the reaction mixture as diluted with ice water (20 mL), neutralized with 10% aqueous $NaHCO_3$ solution (15 mL) and extracted with $CH_2Cl_2$ (2×30 mL). The combined organic extracts were dried over sodium sulfate, filtered and concentrated in vacuo to obtain the crude product, which was precipitated with 10% EtOAc/hexanes to afford compound 107 (55 mg, 51%) as an off-white solid. TLC: 10% $CH_3OH/CH_2Cl_2$ ($R_f$, 0.3); $^1$H-NMR (DMSO-$d_6$, 400 MHz); δ 9.61 (s, 1H), 7.48 (d, J=8.0 Hz, 2H); 7.15 (d, J=8.0 Hz, 2H), 6.33 (s, 1H), 3.66 (t, J=4.8 Hz, 4H), 2.77 (t, J=5.2 Hz, 4H), 2.26 (s, 3H).

Synthesis of 2-(4-((4-metboxyphenyl) sulfonyl) piperazin-1-yl)-N-(p-tolyl)-6-(trifluoromethyl)pyrimidin-4-amine (33): To a stirred solution of compound 107 (50 mg, 0.14 mmol) in $CH_2Cl_2$ (3 mL) under argon atmosphere were added pyridine (0.06 mL, 0.74 mmol) and 4-methoxybenzenesullonyl chloride 40 (33.7 mg, 0.16 mmol) at 0° C.; the mixture was warmed to RT and stirred for 4 h. The reaction was monitored by TLC; after completion of the reaction, the reaction mixture was diluted with $CH_2Cl_2$ (15 mL), washed with 10% aqueous $NaHCO_3$ solution (10 mL) and 1 N HCl (2×15 mL). The organic layer was dried over sodium sulfate, filtered and concentrated in wow to obtain the crude product, which was triturated with 5% EtOAc/n-pentane (2×5 mL) to afford 33 (35 mg, 47%) as an off-white solid. TLC: 50% EtOAc/hexanes ($R_f$, 0.8); $^1$H-NMR (DMSO-$d_6$, 400 MHz): δ 9.65 (s, 1H), 7.68 (d, J=8.8 Hz, 2H), 7.43 (d, J=8.4 Hz, 2H); 7.16-7.12 (m, 4H), 6.33 (s, 1H); 3.82 (s, 3H), 3.80 (t, J=4.8 Hz, 4H); 2.92 (t, J=4.8 Hz, 4H), 2.26 (s, 3H); LC-MS: 96.91%; 508.5 (M$^+$+1); (column: X-select CSH C-18 (50× 3.0 mm, 3.5 μm); RT 4.37 min. 5 mM NH$_4$OAc: ACN; 0.8 mL/min): UPLC (purity): 96.23%; (column: Acquity BEH C-18 (50×2.1 mm, 1.7μ); RT 3.05 min. ACN: 0.025% TFA (Aq); 0.5 mL/min) (IP13080500).

Example 12

Synthesis of 2-(4-((4-methoxyphenyl)sulfonyl)piperazin-1-yl)-4-methyl-6-(methylsulfonyl)pyrimidine (170)—a Common Intermediate

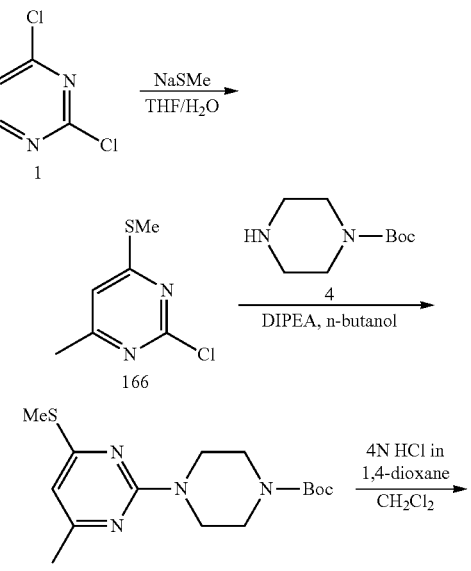

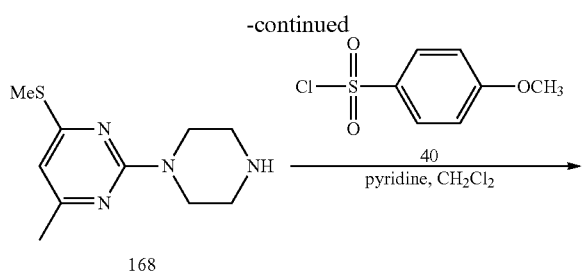

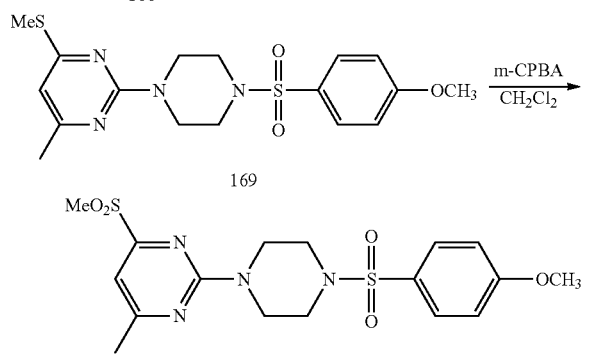

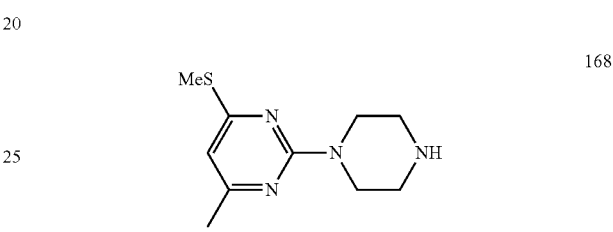

Synthesis of 2-chloro-4-methyl-6-(methylthio)pyrimidine (166)

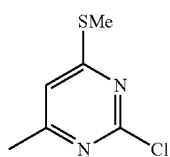

To a stirred solution of 2,4-dichloro-6-methylpyrimidine 1 (200 mg, 1.22 mmol) under argon atmosphere in THF (10 mL) was added sodium methanethiolate (103 mg, 1.47 mmol in 4 mL of water) at −10° C. and stirred for 2 h. The reaction was monitored by TLC; after completion of the reaction, the reaction mixture was diluted with water (20 mL) and extracted with EtOAc (2×30 mL). The combined organic extracts were dried over sodium sulfate, filtered and concentrated in vacuo to obtain the crude product. The crude product was purified through silica gel column chromatography using 3% EtOAc/hexanes to afford compound 166 (130 mg, 61%) as a white solid. TLC: 5% EtOAc/Toluene ($R_f$ 0.8) $^1$H-NMR (DMSO-$d_6$, 400 MHz): δ 7.38 (s, 1H), 2.53 (s, 3H), 2.37 (s, 3H).

Synthesis of tert-butyl 4-(4-methyl-6-(methylthio) pyrimidin-2-yl)piperazine-1-carboxylate (167)

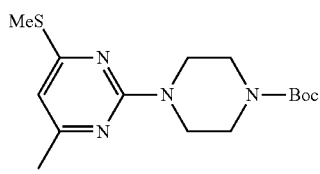

To a stirred solution of compound 166 (100 mg, 0.5 mmol) in n-butanol (5 mL) under argon atmosphere were added tert-butyl piperazine-1-carboxylate 4 (160 mg, 0.86 mmol), diisopropylethylamine (0.16 mL, 0.86 mmol) at RT; the mixture was heated to 100° C. and stirred for 24 h in a sealed tube. The reaction was monitored by TLC; after completion of the reaction, the volatiles were removed in vacuo to obtain the crude product. The crude product was purified through silica gel column chromatography using 10% EtOAc/hexanes to afford compound 167 (120 mg, 65%) as a sticky white solid. TLC: 15% EtOAc/hexanes ($R_f$ 0.7); $^1$H-NMR (DMSO-$d_6$, 400 MHz): δ 6.48 (s, 1H), 3.70 (t, J=4.8 Hz, 4H), 3.78 (t, J=4.8 Hz, 4H), 2.45 (s, 3H), 2.20 (s, 3H), 1.42 (s, 9H).

Synthesis of 4-methyl-6-(methylthio)-2-(piperazin-1-yl)pyrimidine (168)

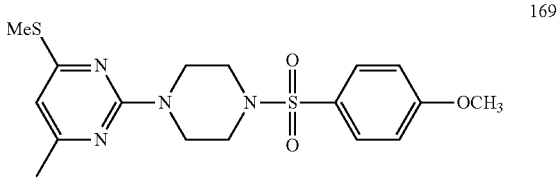 [SMILES: COc1ccc(S(=O)(=O)N2CCN(c3nc(C)cc(SC)n3)CC2)cc1]

To a stirred solution of compound 167 (2 g, 6.17 mmol) in CH$_2$Cl$_2$ (40 mL) under inert atmosphere was added 4 N HCl in 1,4-dioxane (10 mL) at 0° C.; the mixture was warmed to RT and stirred for 3 h. The reaction was monitored by TLC; after completion of the reaction, the volatiles were removed in vacuo. The residue was neutralized with saturated NaHCO$_3$ solution (30 mL) and extracted with CH$_2$Cl$_2$ (2×30 mL). The combined organic extracts were dried over sodium sulfate, filtered and concentrated in vacuo to afford crude compound 168 (1.2 g) as a white solid, TLC: 10% MeOH/CH$_2$Cl$_2$ ($R_f$ 0.2); $^1$H-NMR (DMSO-$d_6$, 400 MHz): δ 6.41 (s, 1H), 3.63 (t, J=5.2 Hz, 4H), 2.70 (t, J=5.2 Hz, 4H), 2.43 (s, 3H), 2.17 (s, 3H).

Synthesis of 2-(4-((4-methoxyphenyl)sulfonyl) 4-methyl-6-methylthio)pyrimidine (169)

To a stirred solution of 168 (1.2 g, crude) in CH$_2$Cl$_2$ (30 mL) under argon atmosphere were added pyridine (2.18 mL, 26.75 mmol), 4-methoxybenzenesulfonyl chloride 35 (1.21 g, 5.87 mmol) at 0° C.; the mixture was warmed to RT and stirred for 4 h. The reaction was monitored by TLC; after completion of the reaction, the reaction mixture was diluted with water (20 mL) and extracted with CH$_2$Cl$_2$ (2×30 mL). The combined organic extracts were washed with 1 N HCl (2×50 mL), 10% NaHCO$_3$ solution (2×50 mL), brine (30 mL), dried over sodium sulfate, filtered and concentrated in lactio to obtain the crude product. The crude product was triturated with pentane (2×5 mL) to afford compound 169 (1.2 g, 57%) as white solid. TLC: 50% EtOAc/hexanes (R_f, 0.8); ¹H-NMR (DMSO-d₆, 400 MHz): δ 7.67 (d, J=8.8 Hz, 2H), 7.13 (d, J=9.2 Hz, 2H), 6.46 (s, 1H), 3.83 (s, 3H), 3.81 (t, J=5.2 Hz, 4H), 2.89 (t, J=4.8 Hz, 4H), 2.41 (s, 3H), 2.16 (s, 3H).

Synthesis of 2-(4-((4-metboxyphenyl) sulfonyl)piperazin-1-yl)-4-methyl-6-methylsulfonyl)pyrimidine (170)

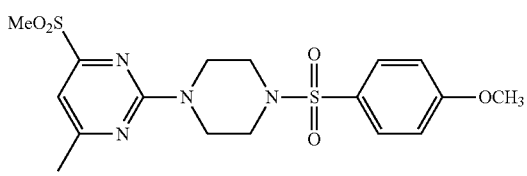

170

To a stirred solution of 169 (1.2 g, 3.04 mmol) in CH₂Cl₂ (48 mL) under argon atmosphere were added m-chloroperoxybenzoic acid (1.4 g, 8.11 mmol) at 0° C.; the mixture was warmed to RT and stirred for 24 h. The reaction was monitored by TLC; after completion of the reaction, the reaction mixture was diluted with water (50 mL) and extracted with CH₂Cl₂ (2×150 mL). The combined organic extracts were washed with 10% NaHCO₃ solution (100 mL), dried over sodium sulfate, filtered and concentrated in vacuo to obtain the crude product. The crude product was purified through silica gel column chromatography using 40% EtOAc/hexanes to afford compound 170 (1 g, 77%) as an off-white solid. TLC: 60% EtOAc/hexanes (R_f, 0.5); ¹H-NMR (DMSO-d₆, 400 MHz): δ 7.68 (d, 9.2 Hz, 2H), 7.14 (d, J=9.2 Hz, 2H), 7.03 (s, 1H), 3.88 (t, J=4.8 Hz, 4H), 3.83 (s, 3H), 3.21 (s, 3H), 2.94 (t, J=4.8 Hz, 4H), 2.39 (s, 3H).

Example 13

Synthesis of 4-chloro-2-(4-((4-methoxyphenyl)sulfonyl)piperazin-1-yl)-6-methylpyrimidine (179) and Compound 180—Common Intermediates

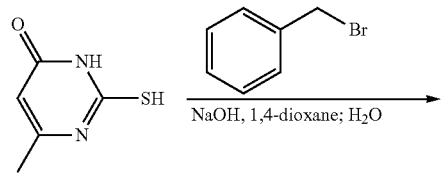

171

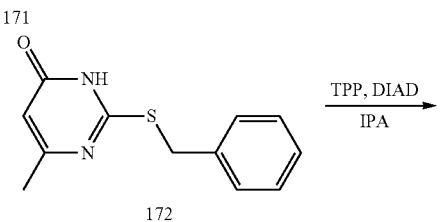

172

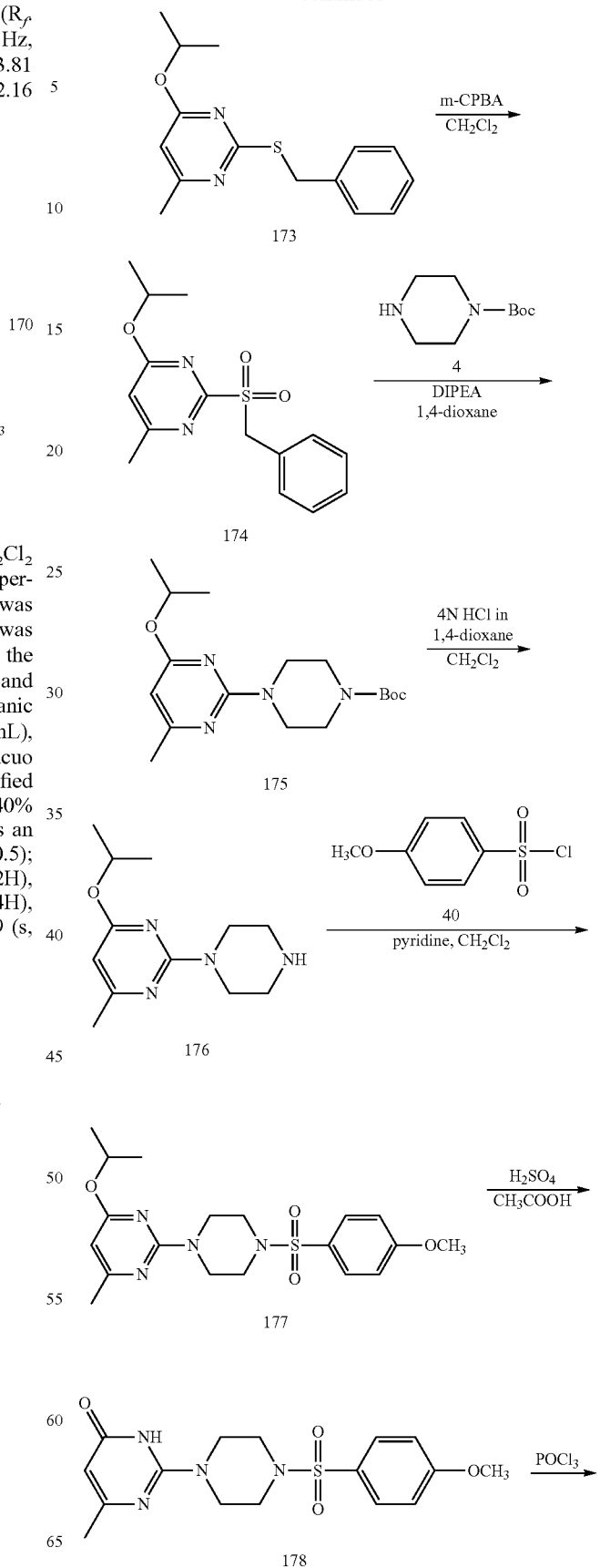

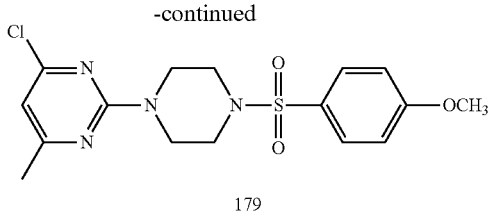

179

Synthesis of 2-(benzylthio)-6-methylpyrimidin-4 (3H)-one (172)

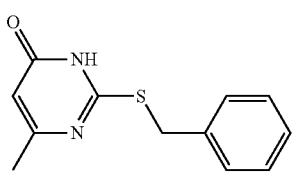

172

To a stirred solution of 2-mercapto-6-thethylpyrimidin-4 (3H)-one 171 (1 g, 7.04 mmol) in 1,4-dioxane (10 mL) was added sodium hydroxide (563 mg, 14.07 mmol in 10 mL of water) and benzyl bromide (1.3 g, 7.74 mmol) at 0° C., the mixture was heated to 50° C. and stirred for 1 h. The reaction was monitored by TLC; after completion of the reaction, the reaction mixture was diluted with ice cold water (20 mL) and the pH was neutralized with 6 N HCl. The precipitated solid was filtered, washed with EtOAc (2×5 mL) water (2×10 mL) and dried in vacuo to afford compound 172 (1 g, 62%) as a yellow syrup. TLC: 40% EtOAc/hexane ($R_f$ 0.5): $^1$H-NMR (DMSO-$d_6$, 400 MHz): δ 12.50-12.23 (m, 1H), 7.42-7.39 (m, 2H), 7.33-7.22 (m, 3H), 5.99 (br s, 1H), 4.37 (s, 2H), 2.20 (s, 3H).

Synthesis of 2-(benzylthio)-4-isopropoxy-6-methypyrimidine (173)

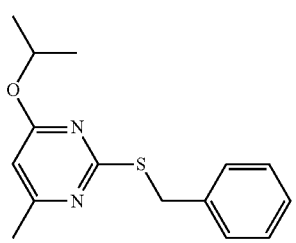

173

To a stirred solution of diisopropyk azodicarboxylate (1.3 g, 6.46 mmol) in ether (10 mL) under argon atmosphere were added triphenyl phosphine (1.6 g, 6.46 mmol) and compound 172 (500 mg, 2.15 mmol) at RT and the mixture was stirred for 15 mm. To this was added isopropyl alcohol (0.4 mL, 5.38 mmol) at RT; the reaction was stirred for 72 h. The reaction was monitored by TLC; after completion athe reaction, the volatiles were removed in vacuo to obtain the crude product. The crude product was purified through silica gel column chromatography using 5% EtOAc/hexanes to afford compound 173 (350 mg 59%) as a yellow syrup. TLC: 40% EtOAc/Aef hexanes ($R_f$ 0.7); $^1$H-NMR (DMSO-$d_6$, 400 MHz): δ 7.41 (d, J=8.4 Hz, 2H), 7.32-7.28 (m, 2H), 7.25-7.21 (m, 1H), 6.40 (s, 1H), 5.30-5.29 (m, 1H), 4.36 (s, 2H), 2.29 (s, 3H), 1.25 (d, J=6.4 Hz, 6H).

Synthesis of 2-(benzylsulfonyl)-4-isopropoxy-6-methylpyrimidine (174)

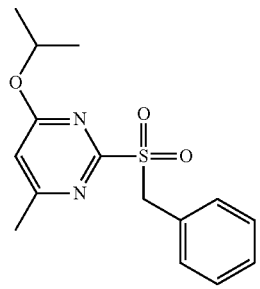

174

To a stirred solution of compound 173 (650 mg, 2.37 mmol) in $CH_2Cl_2$ (10 mL) under argon atmosphere was added m-chloroperoxybenzoic acid (818 mg, 4.74 mmol) at 0° C.; the mixture was warmed to RT and stirred for 4 h. The reaction was monitored by TLC; after completion of the reaction, the reaction mixture was diluted with water (20 mL) and extracted with $CH_2Cl_2$ (2×30 mL). The combined organic extracts were washed with 10% $NaHCO_3$ solution (30 mL) dried over sodium sulfate, filtered and concentrated in vacuo to obtain the crude product. The crude product was purified through silica gel column chromatography using 40% EtOAc/hexanes to afford compound 174 (530 mg, 73%) as white solid. TLC: 30% EtOAc/hexanes ($R_f$ 0.4); $^1$H-NMR (DMSO-$d_6$, 400 MHz): δ 7.39-7.29 (m, 5H), 7.02 (s, 1H), 5.36-5.30 (m, 1H), 4.90 (s, 2H), 2.49 (d, J=4.8 Hz, 3H), 1.31 (d, J=6.0 Hz, 6H).

Synthesis of tert-butyl 4-(4-isopropoxy-6-methylpyrimidin-2-yl)piperazine-1-carboxylate (175)

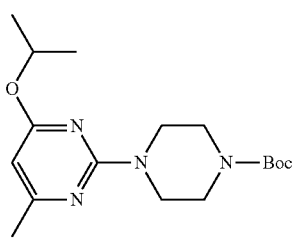

175

To a stirred solution of compound 174 (200 mg, 0.65 mmol) in 1,4-dioxane (10 mL) under argon atmosphere were added tert-butyl piperazine-1-cathoxylate 4 (364 mg, 1.96 mmol) and diisopropylethylamine (0.28 mL, 1.96 mmol) at RT; the mixture was heated to 90° C. and stirred for 48 h. The reaction was monitored by TLC; after completion of the reaction, the volatiles were removed in vacuo to obtain the crude product. The crude product was purified through silica gel column chromatography using 20% EtOAc/hexanes to afford compound 175 (150 mg, 64%) as a yellow syrup.

TLC: 40% EtOAc/hexanes (R$_f$ 0.6); $^1$H-NMR (DMSO-d$_6$, 400 MHz): δ 5.89 (s, 1H), 5.24-5.18 (m, 1H), 3.68-3.65 (m, 4H), 3.38-3.58 (m, 4H), 2.17 (s, 3H), 1.48 (s, 9H), 1.26 (d, d=6.0 Hz, 6H).

Synthesis of 4-isopropoxy-6-methyl-2-(piperazin-1-yl)pyrimidine (176)

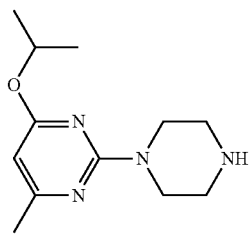

176

To a stirred solution of compound 175 (150 mg, 0.44 mmol) in CH$_2$Cl$_2$ (5 mL) under inert atmosphere was added 4 N HCl in 1,4-dioxane (0.6 mL) at 0° C.; the mixture was warmed to RT and stirred for 4 h. The reaction was monitored by TLC; after completion of the reaction, the volatiles were removed in vacuo. The pH of the residue was neutralized with saturated NaHCO$_3$ solution (30 mL) and extracted with CH$_2$Cl$_2$ (2×30 mL). The combined organic extracts were dried over sodium sulfate, filtered and concentrated in vacuo to afford compound 176 (80 mg, 80%) as a white solid. TLC: 40% EtOAc/hexanes (R$_f$ 0.2); $^1$H-NMR (DMSO-d$_6$, 400 MHz); δ 5.81 (s, 1H), 5.22-5.12 (m, 1H), 3.62-3.58 (m, 4H), 2.72-2.65 (m, 4H), 2.12 (s, 3H), 1.25 (d, J=6.0 Hz, 6H).

Synthesis of 4-isopropoxy-2-(4-(4methoxyphenyl)sulfonyl)piperazin-1-yl)-6-methylpyrimidine (177)

177

To a stirred solution of 176 (80 mg, 0.35 mmol) in CH$_2$Cl$_2$ (5 mL) under argon atmosphere were added pyridine (0.14 mL, 2.2 mmol) and 4-methoxybenzenesulfonyl chloride 35 (100 mg, 0.48 mmol) at 0° C.; the mixture was warmed to RT and stirred for 4 h. The reaction as monitored by TLC: after completion of the reaction, the reaction mixture was diluted with water (20 mL) and extracted with CH$_2$Cl$_2$ (2×30 mL). the combined organic extracts were washed with 1 N HCl (20 mL), 10% NaHCO$_3$ solution (30 mL), brine (30 mL), dried over sodium sulfate, filtered and concentrated in iveuo to afford crude compound 177 (100 mg) as an off-white solid. TLC: 5% MeOH/CH$_2$Cl$_2$ (R$_f$ 0.8); $^1$H-NMR (DMSO-d$_6$, 400 MHz): δ 7.67 (d, J=7.2 Hz, 2H), 7.13 (d, J=7.1 Hz, 2H), 5.87 (s, 1H), 5.18-5.12 (m, 1H), 3.83 (s, 3H), 3.78 (t, J=4.8 Hz, 4H), 2.88 (t, J=4.8 Hz, 4H), 2.13 (s, 3H), 1.22 (d, J=6.0 Hz, 6H).

Synthesis of 2-(4-((4-methoxyphenyl)sulfonyl)piperazin-1-yl)-6-methylpyrimidin-4 (3H)-one (178)

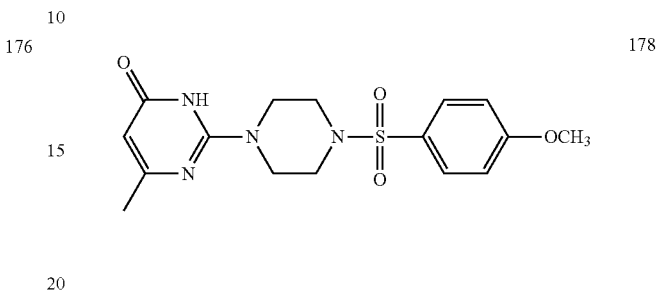

178

To a stirred solution of compound 177 (100 mg, 0.24 mmol) in acetic acid (5 mL) was added 10% aqueous H$_2$SO$_4$ (5 mL) at 0° C. and the mixture was heated to 90° C. for 2 h. The reaction was monitored by TLC; after completion of the reaction, the volatiles were removed in vaciw. The pH of the residue was neutralized with 4 N aqueous MOH solution (30 mL) and the aqueous mixture was extracted with 10% MeOH/CH$_2$Cl$_2$ (2×30 mL). The combined organic extracts were dried over sodium sulfate, filtered and concentrated in vacuo to afford compound 178 (70 mg, 78%) as an off-white solid. TLC: 5% MeOH/CH$_2$Cl$_2$ (R$_f$ 0.2); $^1$H-NMR (DMSO-d$_6$, 400 MHz); δ 7.67 (d, J=7.2 Hz, 2H), 7.14 (d, J=7.2 Hz, 2H), 5.57 (s, 1H), 3.84 (s, 3H), 3.69 (t, J=4.8 Hz, 4H), 2.86 (t, J=4.8 Hz, 4H), 2.02 (s, 3H).

Synthesis of 4-chloro-2-(4-(4-methoxyphenyl)sulfonyl)piperazin-1-yl)-6-methylpyrimidine (179)

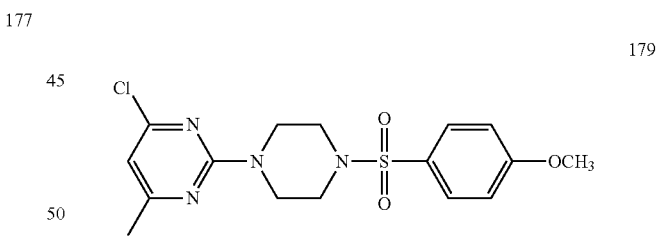

179

To compound 178 (70 mg, 0.19 mmol) was added phosphorous oxychloride (3 mL) under argon atmosphere at 0° C.; the mixture was heated at 90° C. for 3 h. The reaction was monitored by TLC; after completion of the reaction, the volatiles were removed in vacuo. The pH of the residue was neutralized with aqueous NaHCO$_3$ solution (30 mL) and the aqueous mixture extracted with EtOAc (2×30 mL). The combined organic extracts were dried over sodium sulfate, filtered and concentrated in vacuo to afford compound 179 (50 mg, 68%) as an off-white solid, TLC: 5% MeOH/CH$_2$Cl$_2$ (R$_f$ 0.7); $^1$H-NMR (DMSO-d$_6$, 400 MHz): δ 7.66 (d, J=7.2 Hz, 2H), 7.13 (d, J=6.8 Hz, 2H), 6.65 (s, 1H), 3.83 (s, 3H), 3.80 (t, J=4.8 Hz, 3H), 2.91 (t, J=4.8 Hz, 4H), 2.24 (s, 3H).

In a similar manner, compound 180 was prepared:

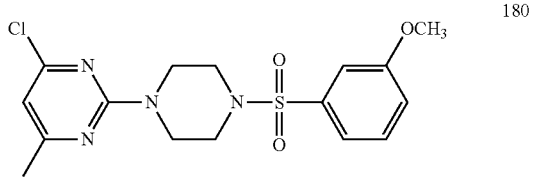 [SMILES: COc1cccc(S(=O)(=O)N2CCN(c3nc(C)cc(Cl)n3)CC2)c1]

180

Example 14

Preparation of Target Compounds 34-45

Further target compounds were prepared using compounds 170, 179, and 180 reacted with various amines employing the following typical procedures B, C, or D and the results are shown in Table 2 below.

Typical procedure B: A mixture of 170 (75 mg, 0.17 mmol) and 4-bromoaniline (1 g) was heated at 120-130° C. in a sealed tube for 4 h. The reaction was monitored by TLC, after completion of the reaction, the reaction mixture was diluted with water (20 mL) and extracted with $CH_2Cl_2$ (3×50 mL). The combined organic extracts were dried over sodium sulfate, filtered and concentrated in vacuo to obtain the crude product. The crude product was either directly dried in vocuo or triturated or purified by column chromatography or preparative HPLC to afford the desired compound.

Typical procedure C: To a stirred solution of compound 179 (70 mg, 0.18 mmol) in 1,4-dioxane (3 mL) under argon atmosphere were added 4-(trifluoromethyl)aniline (32.4 mg, 0.20 mmol) and cesium carbonate (71 mg, 0.21 mmol) at RT, and the mixture was purged with argon for 30 min. To this were added $Pd_2(dba)_3$ (4 mg, 0.004 mmol), Xantphos (5.2 mg, 0.009 mmol), and the mixture was heated to 110-120° C. and stirred for 16 h. The reaction was monitored by TLC; after completion of the reaction, the volatiles were removed in vacuo to obtain the crude product. The residue was diluted with water and extracted with EtOAc (2×20 mL). The combined, organic extracts were dried over sodium sulfate, filtered and dried in vacuo to obtain the crude product. The crude product was directly dried in vacuo, triturated or purified by column chromatography or preparative HPLC to afford the desired compound.

Typical procedure D: A mixture of compound 180 (35 mg, 0.091 mmol) and p-anisidine (11.3 mg, 0.091 mmol) was dissolved in p-dioxane (2 mL). An HCl solution (4 N in p-dioxane) was added dropwise until the solution was acidic by pH paper. The reaction was heated at 90° C. for 16 h, The reaction was monitored by TLC; after completion the reaction mixture was diluted with water (10 mL) and extracted with $CH_2Cl_2$ (3×10 mL). The combined organic extracts were dried over sodium sulfate, filtered and concentrated in vacuo to afford to obtain the crude product. The crude product was either directly dried in vacuo or triturated or purified by column chromatography or preparative HPLC to afford the desired compound.

TABLE 2

| Target Cmpd. No. | Structure | Procedure, Intermediates | Rx. Yield | Mass Spec. Found | Mass Spec. Calculated | $^1$H-NMR |
|---|---|---|---|---|---|---|
| 34 | 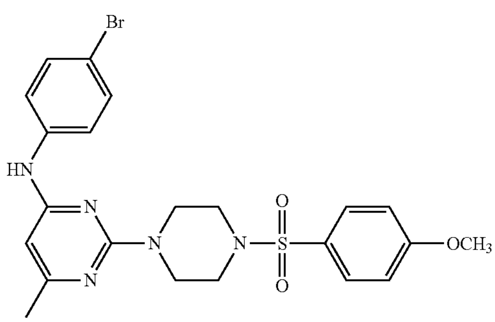 [SMILES: COc1ccc(S(=O)(=O)N2CCN(c3nc(C)cc(Nc4ccc(Br)cc4)n3)CC2)cc1] | B, 170 | 38% | 517.19 ($M^+ + 1$), 519.8 ($M^+ + 2$); | 517.08 for $C_{22}H_{24}BrN_5O_3S$ | $^1$H-NMR (DMSO-$d_6$, 500 MHz): δ 9.27 (s, 1H), 7.68 (d, J = 8.5 Hz, 2H), 7.53 (d, J = 8.5 Hz, 2H), 7.65 (d, J = 8.5 Hz, 2H), 7.14 (d, J = 9.0 Hz, 2H), 5.90 (s, 1H), 3.83 (s, 3H), 3.90-3.77 (m, 4H), 2.91-2.86 (m, 4H), 2.12 (s, 3H); |
| 35 | 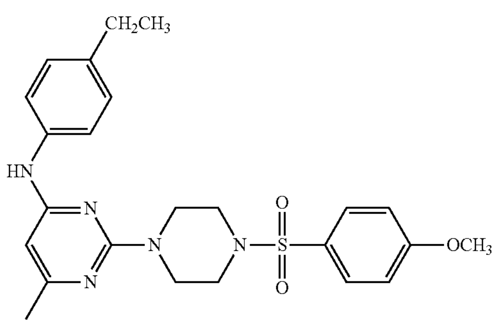 [SMILES: CCc1ccc(Nc2cc(C)nc(N3CCN(S(=O)(=O)c4ccc(OC)cc4)CC3)n2)cc1] | B, 170 | 38% | 467.9 ($M^+ + 1$); | 467.20 for $C_{24}H_{29}N_5O_3S$ | $^1$H-NMR (DMSO-$d_6$, 400 MHz): δ 9.02 (s, 1H), 7.68 (d, J = 8.8 Hz, 2H), 7.43 (d, J = 8.4 Hz, 2H), 7.14-7.11 (m, 4H), 5.87 (s, 1H), 3.82 (s, 3H), 3.78 (d, J = 4.8 Hz, 4H), 2.88 (t, J = 4.8 Hz, 4H), 2.57-2.53 (m, 2H), 2.08 (s, 3H), 1.64 (t, J = 7.6 Hz, 3H); |

TABLE 2-continued

| Target Cmpd. No. | Structure | Procedure, Intermediates | Rx. Yield | Mass Spec. Found | Mass Spec. Calculated | $^1$H-NMR |
|---|---|---|---|---|---|---|
| 36 | (4-OCF₃-phenyl)HN–[6-methylpyrimidine-2-yl]–piperazine–SO₂–(4-OCH₃-phenyl) | B, 170 | 40% | 523.9 (M⁺ + 1) | 523.15 for $C_{23}H_{24}F_3N_5O_4S$ | $^1$H-NMR (DMSO-d$_6$, 500 MHz): δ 9.33 (s, 1H), 7.69-7.66 (m, 4H), 7.28 (d, J = 8.5 Hz, 2H), 7.14 (d, J = 9.0 Hz, 2H), 5.92 (s, 1H), 3.83 (s, 3H), 3.79 (t, J = 4.5 Hz, 4H), 2.91 (t, J = 4.5 Hz, 4H), 2.12 (s, 3H); |
| 37 | (4-Cl-phenyl)HN–[6-methylpyrimidine-2-yl]–piperazine–SO₂–(4-OCH₃-phenyl) | B, 170 | 22% | 473.9 (M⁺ + 1) | 473.13 for $C_{22}H_{24}ClN_5O_3S$ | $^1$H-NMR (DMSO-d$_6$, 500 MHz): δ 9.26 (s, 1H), 7.68 (d, J = 9.0 Hz, 2H), 7.58 (d, J = 9.0 Hz, 2H), 7.32 (d, J = 8.5 Hz, 2H), 7.14 (d, J = 8.5 Hz, 2H), 5.90 (s, 1H), 3.83 (s, 3H), 3.90-3.77 (m, 4H), 2.91-2.86 (m, 4H), 2.11 (s, 3H); |
| 38 | (4-F-phenyl)HN–[6-methylpyrimidine-2-yl]–piperazine–SO₂–(4-OCH₃-phenyl) | B, 170 | 44% | 458.0 (M⁺ + 1) | 457.16 for $C_{22}H_{24}FN_5O_3S$ | $^1$H-NMR (DMSO-d$_6$, 400 MHz): δ 9.13 (s, 1H), 7.67 (d, J = 8.0 Hz, 2H), 7.55-7.51 (m, 2H), 7.14-7.09 (m, 4H), 5.86 (s, 1H), 3.82 (s, 3H), 3.77 (t, J = 4.8 Hz, 4H), 2.88 (t, J = 4.8 Hz, 4H), 2.09 (s, 3H); |
| 39 | (phenyl)HN–[6-methylpyrimidine-2-yl]–piperazine–SO₂–(4-OCH₃-phenyl) | B, 170 | 38% | 440.3 (M⁺ + 1) | 439.17 for $C_{22}H_{25}N_5O_3S$ | $^1$H-NMR (DMSO-d$_6$, 400 MHz): δ 9.11 (s, 1H), 7.67 (d, J = 6.8 Hz, 2H), 7.53 (d, J = 7.6 Hz, 2H), 7.28 (t, J = 7.6 Hz, 2H), 7.13 (d, J = 7.2 Hz, 2H), 6.95 (t, J = 7.2 Hz, 1H), 5.90 (s, 1H), 3.82 (s, 3H), 3.78 (t, J = 4.8 Hz, 4H), 2.89 (t, J = 4.8 Hz, 4H), 2.10 (s, 3H); |

TABLE 2-continued

| Target Cmpd. No. | Structure | Procedure, Intermediates | Rx. Yield | Mass Spec. Found | Mass Spec. Calculated | $^1$H-NMR |
|---|---|---|---|---|---|---|
| 40 | 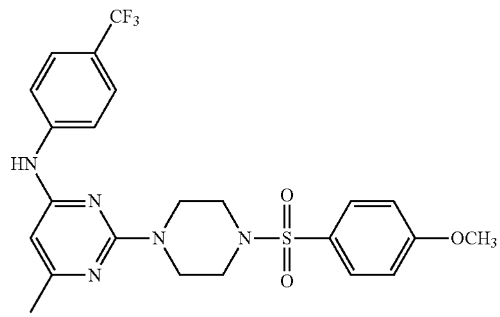 | C, 179 | 38% | 507.9 (M$^+$ + 1); | 507.16 for C$_{23}$H$_{24}$F$_3$N$_5$O$_3$S | $^1$H-NMR (DMSO-d$_6$, 400 MHz): δ 9.54 (s, 1H), 7.78 (d, J = 8.8 Hz, 2H), 7.69-7.64 (m, 4H), 7.13 (d, J = 7.2 Hz, 2H), 5.97 (s, 1H), 3.82 (s, 3H), 3.80 (t, J = 5.2 Hz, 4H), 2.91 (t, J = 4.8 Hz, 4H), 2.14 (s, 3H); |
| 41 | 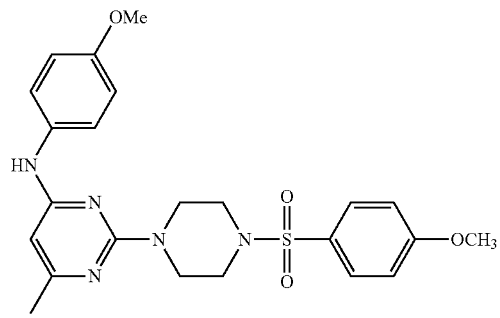 [SMILES: COc1ccc(Nc2cc(C)nc(N3CCN(S(=O)(=O)c4ccc(OC)cc4)CC3)n2)cc1] | C, 179 | 40% | 469.9 (M$^+$ + 1); | 469.18 for C$_{23}$H$_{27}$N$_5$O$_4$S | $^1$H-NMR (DMSO-d$_6$, 400 MHz): δ 8.91 (s, 1H), 7.67 (d, J = 7.2 Hz, 2H), 7.40 (d, J = 8.8 Hz, 2H), 7.13 (d, J = 7.2 Hz, 2H), 6.87 (d, J = 8.8 Hz, 2H), 5.81 (s, 1H), 3.83 (s, 3H), 3.76 (t, J = 4.8 Hz, 4H), 3.72 (s, 3H), 2.87 (t, J = 4.8 Hz, 4H), 2.07 (s, 3H); |
| 42 | 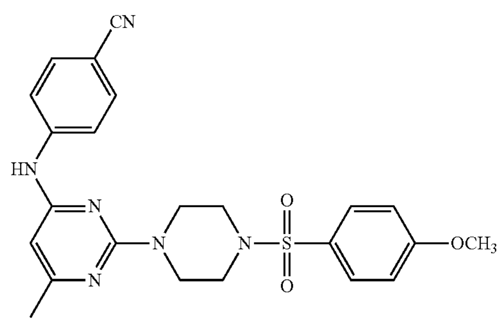 [SMILES: COc1ccc(S(=O)(=O)N2CCN(c3nc(C)cc(Nc4ccc(C#N)cc4)n3)CC2)cc1] | C, 179 | 25% | 465.3 (M$^+$ + 1); | 464.16 for C$_{23}$H$_{24}$N$_6$O$_3$S | $^1$H-NMR (DMSO-d$_6$, 400 MHz): δ 9.65 (s, 1H), 7.76-7.67 (m, 6H), 7.13 (d, J = 9.2 Hz, 2H), 5.98 (s, 1H), 3.82 (s, 3H), 3.80 (t, J = 4.8 Hz, 4H), 2.91 (t, J = 4.8 Hz, 4H), 2.14 (s, 3H); |
| 43 | 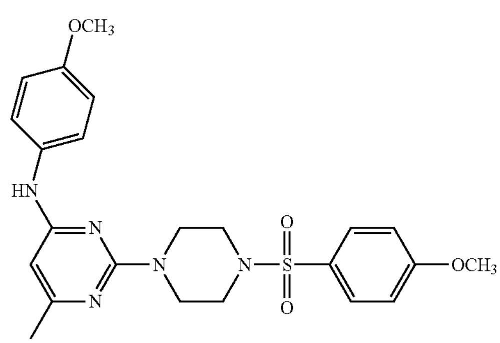 [SMILES: COc1ccc(Nc2cc(C)nc(N3CCN(S(=O)(=O)c4ccc(OC)cc4)CC3)n2)cc1] | D, 180 | 54% | 470.2 (M + 1)$^+$ | 469.18 for C$_{23}$H$_{27}$N$_5$O$_4$S | $^1$H NMR (400 MHz, CDCl$_3$) δ 7.35 (t, J = 7.9 Hz, 2H), 7.25 (s, 1H), 7.19 (d, J = 2.7 Hz, 2H), 7.10 (d, J = 8.6 Hz, 2H), 7.03 (dd, J = 8.3, 2.5 Hz, 1H), 6.81 (d, J = 8.6 Hz, 2H), 6.18 (s, 1H), 5.65 (s, 1H), 3.84 (m, 4H), 3.78 (s, 3H), 3.74 (s, 3H), 2.99 (m, 4H). |

TABLE 2-continued

| Target Cmpd. No. | Structure | Procedure, Intermediates | Rx. Yield | Mass Spec. Found | Mass Spec. Calculated | ¹H-NMR |
|---|---|---|---|---|---|---|
| 44 | (structure) | D, 180 | 59% | 458.2 (M + 1)⁺ | 457.16 for $C_{22}H_{24}FN_6O_3S$ | ¹H NMR (400 MHz, CDCl₃) δ 7.35 (t, J = 7.9 Hz, 2H), 7.25 (s, 1H), 7.17 (dd, J = 9.2, 4.5 Hz, 3H), 7.03 (dd, J = 8.2, 2.5 Hz, 1H), 6.96 (t, J = 8.6 Hz, 2H), 6.28 (s, 1H), 5.69 (s, 1H), 3.83 (t, J = 5.0 Hz, 4H), 3.77 (s, 3H), 2.99 (t, J = 5.0 Hz, 4H) |

Target compound 45 is shown below and may be prepared by known methods:

45

Example 15

Capsid Assembly Assay

A screening for assembly effector activity was conducted based on a fluorescence quenching assay developed in the Zlotnick lab (Stray et al., 2006; Zlotnick et al., 2007). A Cp mutant is specifically labeled with a fluorescent dye. In the dimeric state fluorescence is intense. However, when the Cp assembles, the dye molecules accumulate at fivefold and quasi-sixfold vertices to self quench by up to 95%. In the high throughput screen, the Cp concentration is chosen so that addition of NaCl, typically 150 mM or 300 mM is sufficient to induce about 25% assembly. Thus, assembly effectors that enhance assembly are readily detected.

As illustrated by the effect of CpAM molecules on HBV Cp assembly, as measured using the fluorescence quenching assay, the test revealed that the CpAM molecules enhanced assembly kinetics and stabilized protein-protein interactions (Table 3). Control reactions, with no drug, show 25±5% assembly in a 24 h time period.

TABLE 3

| Target Compound # | % Capsid formation at 24 h (10 μM) |
|---|---|
| 1 | 95 |
| 2 | 83 |
| 3 | 94 |
| 4 | 99 |
| 5 | 91 |
| 6 | 92 |
| 7 | 79 |
| 8 | 98 |
| 9 | 93 |
| 10 | 96 |
| 11 | 89 |
| 12 | 73 |
| 13 | 60 |
| 14 | 67 |
| 15 | 76 |
| 16 | 95 |
| 17 | 70 |
| 18 | 71 |
| 19 | 83 |
| 20 | 90 |
| 21 | 71 |
| 22 | 80 |
| 23 | 88 |
| 24 | 96 |
| 25 | 94 |
| 26 | 96 |
| 27 | 84 |
| 28 | 96 |
| 29 | 94 |
| 30 | 87 |
| 31 | 87 |
| 32 | 69 |
| 33 | 93 |
| 34 | 96 |
| 35 | 81 |
| 36 | 78 |
| 37 | 93 |
| 38 | 75 |
| 39 | 56 |
| 40 | 91 |
| 41 | 84 |
| 42 | 69 |
| 43 | 97 |
| 44 | 92 |
| 45 | 87 |

Example 16

Assay Measuring Activity of Test Compounds on Viral Production from AD38 Cells AD38 cells grown in a 175 cm flash with Growth Medium (DMEM/F12 (1:1) (cat#SH30023.01, Hyclone, 1× Pen/step (cat#: 30-002-CL, Mediatech, Inc), 10% FBS (cat#: 101, Tissue Culture Biologics), 250 µg/mL G418 (cat#: 30-234-CR, Mediatech, Inc), 1 µg/mL Tetracycline (cat#: T3325, Teknova)) were detached with 0.25% trypsin. Tetracycline-free treatment medium (15 mL DMEM/F12 (1:1) (cat#SH30023.01, Hyclone, 1× Pen/step (cat#: 30-002-CL, Mediatech, Inc), with 2% FBS, Tet-system approved (cat#: 631106, Clontech) were then added to mix and spun at 1300 rpm for 5 min. Pelleted cells were then re-suspended/washed with 50 mL of 1×PBS 2 times and 10 mL treatment medium one time. AD38 cells were then re-suspended with 10 mL of treatment medium and counted. Wells of a collagen coated 96-well NUNC microtiter plate were seeded at 50,000/well in 180 µL of treatment medium, and 20 µL of either 10% DMSO (Control) or a 10× solution of test compound in 10% DMSO in treatment media was added for as final compound concentration 1, 3, or 10 µM (1.0% final [DMSO]) and plates were incubated for 5 days at 37° C.

Subsequently viral load production was assayed by quantitative PCR of the core sequence. Briefly, 5 µL of clarified supernatant was added to a PCR reaction mixture that contained forward primers HBV-f 5'-CTGTGCCTTGGGTGGCTTT-3', Reverse primers HBV-r 5'-AAGGAAAGAAGTCAGAAGGCAAAA-3' and Fluorescent TaqMan™ Probes HBV-probe 5'-FAM/AGCTCCAAA/ZEN/TTCTTTATAAGGGTCGATGTCCATG/31ABkFQ-3' in Quanta Biosciences PerfeCTa® qPCR Toughmix®, and was subsequently on an Applied Biosystems VIIA7 in a final volume of 20 µL. The PCR mixture was incubated at 45° C. for 5 minutes, then 95° C. for 10 min, followed by 40 cycles of 10 seconds at 95° C. and 20 seconds at 60° C. Viral load was quantitated against known standards by using ViiA™ 7 Software. Viral load in the supernatant from wells with treated cells were compared against viral load in supernatant from DMSO control wells (≥3 per plate). In Table 4, concentrations of test compound causing reductions in viral load greater than at least 3 standard deviations from the DMSO controls across all plates were considered active, with (+) depicting meets criteria for significant activity, and (++) depicting exceeds criteria.

TABLE 4

| Target Compound # | Test concentration | | |
|---|---|---|---|
| | 1 µM | 3 µM | 10 µM |
| 1 |  | ++ | ++ |
| 3 | ++ | ++ | ++ |
| 5 |  | ++ | ++ |
| 6 |  | ++ | ++ |
| 7 | + | ++ | ++ |
| 8 |  | ++ | ++ |
| 10 | + | ++ | ++ |
| 11 |  | ++ | ++ |
| 15 |  | ++ | ++ |
| 16 | ++ | ++ | ++ |
| 18 |  | ++ | ++ |
| 23 | + | ++ | ++ |
| 24 |  | ++ | ++ |
| 26 |  | ++ | ++ |
| 27 |  | ++ | ++ |
| 28 | ++ | ++ | ++ |
| 29 | ++ | ++ | ++ |
| 31 |  | ++ | ++ |
| 32 | ++ | ++ | ++ |
| 33 | ++ | ++ | ++ |
| 34 | ++ | ++ | ++ |
| 35 | ++ | ++ | ++ |
| 37 | ++ | ++ | ++ |
| 40 | ++ | ++ | ++ |
| 42 |  |  | ++ |

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

EQUIVALENTS

Those skilled in the art will recognize, or be able to ascertain using no more than routine experimentation, any equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

We claim:

1. A pharmaceutical composition comprising: (i) a compound of Formula 1 having the structure:

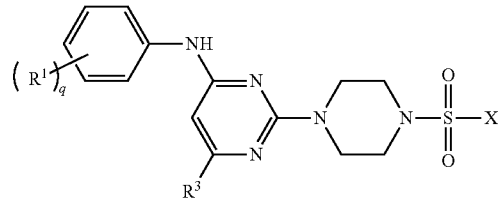

Formula 1 or a pharmaceutically acceptable salt or stereoisomer thereof, wherein:

X is selected from the group consisting of

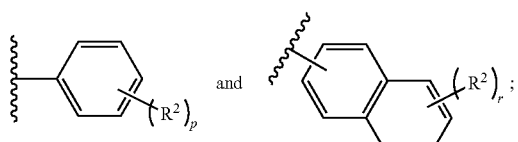

and q is 0, 1, 2, 3 or 4;
p is 0, 1, 2, 3, or 4;
r is 0, 1, 2, 3, or 4;

R[1] is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R");

w is 0, 1 or 2;

R' is independently for each occurrence selected from the group consisting of —H and —$C_1$-$C_6$alkyl;

R" is independently for each occurrence selected from the group consisting of —H and —$C_1$-$C_6$alkyl; or R' and R" are taken together with the nitrogen atom to which they are attached to form a 4-7 membered heterocyclic ring;

R[2] is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —S(O)$_w$—$C_1$-$C_6$alkyl, —N(R')S(O)$_w$—$C_1$-$C_6$alkyl, and —S(O)$_w$—N(R')(R"); and R[3] is selected from the group consisting of —H and —$C_1$-$C_6$alkyl;

wherein $C_1$-$C_6$alkyl or $C_1$-$C_6$alkoxy may be independently for each occurrence optionally substituted with one, two, or three halogens; and (ii) a pharmaceutically acceptable excipient.

2. The pharmaceutical composition according to claim 1, wherein p is 1.

3. The pharmaceutical composition according to claim 1, wherein p is 2.

4. The pharmaceutical composition according to claim 1, wherein the compound of Formula 1 is represented by Formula 1-A:

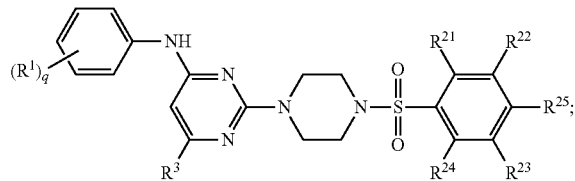

Formula 1-A or a pharmaceutically acceptable salt or stereoisomer thereof, wherein:

R[21] is independently for each occurrence selected from the group consisting of —H and halogen;

R[22] is independently for each occurrence selected from the group consisting of —H, —$C_1$-$C_6$alkyl, —$C_1$-$C_6$alkoxy, —$C_1$-$C_6$alkyl-C—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R");

R[23] is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R"); and R[24] is independently for each occurrence selected from the group consisting of —H and halogen;

R[25] is independently for each occurrence selected from the group consisting of —H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —S(O)$_w$—$C_1$-$C_6$alkyl, —N(R')S(O)$_w$—$C_1$-$C_6$alkyl, and —S(O)$_w$—N(R')(R");

wherein $C_1$-$C_6$alkyl or $C_1$-$C_6$alkoxy may be independently for each occurrence optionally substituted with one, two, or three halogens.

5. The pharmaceutical composition according to claim 4, wherein R[21] and/or R[24] is —H.

6. The pharmaceutical composition according to claim 4, wherein R[22] is selected from the group consisting of H, —$C_1$-$C_6$alkyl, —$C_1$-$C_6$alkoxy, —$C_1$-$C_6$alkyl-O—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R").

7. The pharmaceutical composition according to claim 4, wherein R[22] is independently for each occurrence selected from the group consisting of —H, —$C_1$-$C_6$alkyl, —$C_1$-$C_6$alkoxy, and halogen.

8. The pharmaceutical composition according to claim 4, wherein R[23] is selected from the group consisting of H, —$C_1$-$C_6$alkyl, —$C_1$-$C_6$alkoxy, —$C_1$-$C_6$alkyl-C—$C_1$-$C_6$alkyl, halogen, cyano, —OH, —C(O)H, —$CO_2$R', —C(O)N(R')(R"), —C(O)$C_1$-$C_6$alkyl, —N(R')(R"), —$NO_2$, —N(R')C(O)$C_1$-$C_6$alkyl, —S(O)$_w$—$C_1$-$C_6$alkyl, —N(R')S(O)$_w$—$C_1$-$C_6$alkyl, and —S(O)$_w$—N(R')(R").

9. The pharmmaceutical composition according to claim 4, wherein R[23] is independently for each occurrence selected from the group consisting of —H, —$C_1$-$C_6$alkyl, —$C_1$-$C_6$alkoxy, and halogen.

10. The pharmaceutical composition according to claim 4, wherein R[25] is selected from the group consisting of —H, —$C_1$-$C_6$alkyl, —$C_1$-$C_6$alkoxy, halogen, cyano, —$CO_2$R', —C(O)N(R')(R"), —C(O)$C_1$-$C_6$alkyl, and —N(R')(R").

11. The pharmaceutical composition according to claim 1, wherein R[1] is selected independently for each occurrence from the group consisting of —H, —$C_1$-$C_6$alkyl, —$C_1$-$C_6$alkoxy, halogen, cyano, and —OH.

12. The pharmaceutical composition according to claim 1, wherein q is 1 or 2.

13. A pharmaceutical composition according to claim 4, wherein the compound of Formula 1 is represented by Formula 1-B:

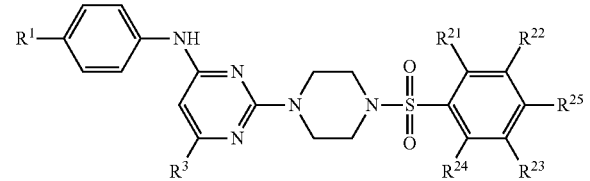

Formula 1-B or a pharmaceutically acceptable salt or stereoisomer thereof.

14. The pharmaceutical composition according to claim 1, wherein R[1] is selected from the group consisting of —H, —$CH_3$, —$CH_2CH_3$, —$CF_3$, —F, —Cl, —Br, cyano, —$OCH_3$, and —$OCF_3$.

15. The pharmaceutical composition according to claim 4, wherein $R^{23}$ is selected from the group consisting of —H, —CH$_3$, —F, and —OCH$_3$.

16. The pharmaceutical composition according to claim 4, wherein $R^{25}$ is selected from the group consisting of —H, —CH$_3$, —CH$_2$CH$_3$, —CH$_2$CH$_2$CH$_2$CH$_3$, —CF$_3$, —F, —Cl, —OH, —OCH$_3$, —OCH$_2$CH$_3$, —OC(CH$_3$)$_3$, —OCH$_2$CH$_2$CH$_2$CH$_3$, —NH$_2$, —NHCH$_3$, —NHC(O)CF—$_3$, —OCHF$_2$, and —OCF$_3$.

17. The pharmaceutical composition according to claim 1, wherein $R^3$ is selected from the group consisting of —CH$_3$, —CH(CH$_3$)$_2$, —CH$_2$CH$_2$CH$_3$, —CF$_3$, and —C(CH$_3$)$_3$.

18. The pharmaceutical composition according to claim 1, wherein $R^2$ is selected from the group consisting of —H, —CH$_3$, —CH$_2$CH$_3$, —CF$_3$, —F, —Cl, —Br, cyano, —OCH$_3$, and —OCF$_3$.

* * * * *